(12) United States Patent
Moores et al.

(10) Patent No.: US 11,459,391 B2
(45) Date of Patent: Oct. 4, 2022

(54) COMBINATION THERAPIES AND PATIENT STRATIFICATION WITH BISPECIFIC ANTI-EGFR/C-MET ANTIBODIES

(71) Applicant: Janssen Biotech, Inc., Horsham, PA (US)

(72) Inventors: Sheri Moores, Wayne, PA (US); Smruthi Vijayaraghavan, Spring House, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 75 days.

(21) Appl. No.: 16/798,662

(22) Filed: Feb. 24, 2020

(65) Prior Publication Data

US 2020/0270351 A1 Aug. 27, 2020

Related U.S. Application Data

(60) Provisional application No. 62/810,716, filed on Feb. 26, 2019, provisional application No. 62/930,190, filed on Nov. 4, 2019.

(51) Int. Cl.
*C07K 16/28* (2006.01)
*A61K 45/06* (2006.01)

(52) U.S. Cl.
CPC .......... *C07K 16/2863* (2013.01); *A61K 45/06* (2013.01); *C07K 2317/31* (2013.01); *C07K 2317/565* (2013.01)

(58) Field of Classification Search
CPC ............ C07K 16/2863; C07K 2317/31; C07K 2317/565; A61K 45/06
See application file for complete search history.

(56) References Cited

U.S. PATENT DOCUMENTS

| | | |
|---|---|---|
| 7,615,529 B2 | 11/2009 | Kong-Beltran et al. |
| 7,767,792 B2 | 8/2010 | Johns et al. |
| 7,892,770 B2 | 2/2011 | Cao et al. |
| 7,981,605 B2 | 7/2011 | Freeman et al. |
| 8,067,175 B2 | 11/2011 | Varmus et al. |
| 8,242,247 B2 | 8/2012 | Klein et al. |
| 8,323,962 B2 | 12/2012 | Dall'Acqua et al. |
| 8,501,171 B2 | 8/2013 | Bourel et al. |
| 8,536,118 B2 | 9/2013 | Kong-Beltran et al. |
| 8,562,985 B2 | 10/2013 | Michaud et al. |
| 8,652,473 B2 | 2/2014 | Johns et al. |
| 8,715,665 B2 | 5/2014 | Janne et al. |
| 8,821,869 B2 | 9/2014 | Michaud et al. |
| 8,962,808 B2 | 2/2015 | Chan et al. |
| 9,394,367 B2 | 7/2016 | Cheong et al. |
| 9,580,508 B2 | 2/2017 | Chiu et al. |
| 9,593,098 B2 | 3/2017 | Suh et al. |
| 9,593,164 B2 | 3/2017 | Chiu et al. |
| 9,683,052 B2 | 6/2017 | Blein et al. |
| 9,683,053 B2 | 6/2017 | Blein et al. |
| 10,626,189 B2 | 4/2020 | Giese et al. |
| 10,813,933 B2 | 10/2020 | Katayama et al. |
| 2005/0272083 A1 | 12/2005 | Seshagiri |
| 2007/0287170 A1 | 12/2007 | Davis et al. |
| 2009/0182127 A1 | 7/2009 | Kjaergaard et al. |
| 2010/0015133 A1 | 1/2010 | Igawa et al. |
| 2011/0123532 A1 | 5/2011 | Gurney et al. |
| 2012/0149876 A1 | 6/2012 | Von Kreudenstein et al. |
| 2013/0195849 A1 | 8/2013 | Von Kreudenstein et al. |
| 2014/0141000 A1 | 5/2014 | Chiu et al. |
| 2017/0073414 A1 | 3/2017 | Weiskopf et al. |
| 2018/0312604 A1 | 11/2018 | Throsby et al. |
| 2019/0248907 A1 | 8/2019 | Doemer et al. |
| 2019/0315873 A1 | 10/2019 | Michieli |
| 2019/0046641 A1 | 12/2019 | Patel et al. |
| 2020/0087405 A1 | 3/2020 | Sidhu et al. |
| 2020/0239595 A1 | 7/2020 | Allison et al. |
| 2020/0316071 A1 | 10/2020 | Robichaux et al. |
| 2020/0317792 A1 | 10/2020 | Griswold et al. |
| 2020/0325243 A1 | 10/2020 | Tikhomirov et al. |
| 2020/0360394 A1 | 11/2020 | Oh et al. |
| 2021/0017285 A1 | 1/2021 | Laquerre et al. |

FOREIGN PATENT DOCUMENTS

| | | |
|---|---|---|
| EP | 1868648 B1 | 4/2015 |
| EP | 1851339 B1 | 5/2016 |
| EP | 3611273 A1 | 2/2020 |
| WO | WO 1988001649 A1 | 3/1988 |
| WO | WO 1992001047 A1 | 1/1992 |
| WO | WO 1994013804 A1 | 6/1994 |
| WO | WO 1998044001 A1 | 10/1998 |
| WO | WO 2006028936 A2 | 3/2006 |
| WO | WO 2006028936 A3 | 3/2006 |
| WO | WO 2008077546 A1 | 7/2008 |
| WO | WO 2009018386 A1 | 2/2009 |
| WO | WO 2009080251 A1 | 7/2009 |

(Continued)

OTHER PUBLICATIONS

Moores et al., A Novel Bispecific Antibody Targeting EGFR and cMet is Effective against EGFR Inhibitor-Resistant Lung Tumors. Cancer Res. 76(13):3942-3953, Jul. 1, 2016.*
Grugan et al., Fc-mediated activity of EGFR x c-Met bispecific antibody JNJ-61186372 enhanced killing of lung cancer cells. MABS 9 (1):114-126, 2017.*
Vijayaraghavan et al., Amivantamab (JNJ-61186372), an Fc Enhanced EGFR/cMet Bispecific Antibody, Induces Receptor Downmodulation and Antitumor Activity by Monocyte/Macrophage Trogocytosis. Mol Cancer Ther 19:2044-2056, 2020.*
Almatroodi et al., 2016, "Characterization of M1/M2 Tumour-Associated Macrophages (TAMs) and Th1/Th2 Cytokine Profiles in Patients with NSCLC," Cancer Microenviron, 9(1):1-11 (Epub 2015).
Arenberg et al., 2000, "Macrophage infiltration in human non-small-cell lung cancer: the role of CC chemokines," Cancer Immunol. Immunother., 49(2):63-70.
Arend et al., 2000, "Biological role of interleukin 1 receptor antagonist isoforms," Ann. Rheum. Dis., 59 Suppl 1(Suppl 1):i60-64.

(Continued)

*Primary Examiner* — Ruixiang Li
(74) *Attorney, Agent, or Firm* — Jones Day

(57) ABSTRACT

The present invention relates to combination therapies and patient stratification with bispecific anti-EGFR/c-Met antibodies.

27 Claims, 49 Drawing Sheets
(8 of 49 Drawing Sheet(s) Filed in Color)

Specification includes a Sequence Listing.

(56) References Cited

FOREIGN PATENT DOCUMENTS

| | | |
|---|---|---|
| WO | WO 2009080252 A1 | 7/2009 |
| WO | WO 2009080254 A1 | 7/2009 |
| WO | WO 2009085462 A1 | 7/2009 |
| WO | WO 2011131746 A2 | 10/2011 |
| WO | WO 2011131746 A3 | 10/2011 |
| WO | WO 2015043614 A1 | 4/2015 |
| WO | WO 2015188777 A1 | 12/2015 |
| WO | WO 2016081423 A1 | 5/2016 |
| WO | WO 2018094225 A1 | 5/2018 |
| WO | WO 2018194356 A1 | 10/2018 |
| WO | WO 2020055643 A2 | 3/2020 |
| WO | WO 2020055643 A3 | 3/2020 |
| WO | WO 2020205521 A1 | 10/2020 |
| WO | WO 2020214824 A1 | 10/2020 |
| WO | WO 2020214831 A1 | 10/2020 |
| WO | WO 2020230091 A1 | 11/2020 |

OTHER PUBLICATIONS

Balkwill, 2004, "Cancer and the chemokine network," Nat. Rev. Cancer, 4(7):540-550.

Bean et al., 2007, "MET amplification occurs with or without T790M mutations in EGFR mutant lung tumors with acquired resistance to gefitinib or erlotinib," Proc. Natl. Acad. Sci. USA, 104(52):20932-20937.

Cappuzzo et al., 2005, "Epidermal growth factor receptor gene and protein and gefitinib sensitivity in non-small-cell lung cancer," J. Natl. Cancer Inst., 97(9):643-655.

Chen et al., 2009, "Clinicopathologic and molecular features of epidermal growth factor receptor T790M mutation and c-MET amplification in tyrosine kinase inhibitor-resistant Chinese non-small cell lung cancer," Pathol, Oncol. Res., 15(4):651-658.

Cho et al., 2018 "Abstract MA26.09: Lazertinib, a Third Generation EGFR-TKI, in Patients with EGFR-TKI-Resistant NSCLC: Updated Results of a Phase I/II Study," Journal of Thoracic Oncology, 13:S453.

Chothia et al., 1987, "Canonical structures for the hypervariable regions of immunoglobulins," J. Mol. Biol., 196(4):901-917.

Eisenhauer et al., 2009, "New response evaluation criteria in solid tumours: revised RECIST guideline (version 1.1)," Eur. J. Cancer, 45(2):228-247.

Engelman et al., 2007, "MET amplification leads to gefitinib resistance in lung cancer by activating ERBB3 signaling," Science, 316(5827):1039-1043.

Ferrara et al., 2006, "Modulation of therapeutic antibody effector functions by glycosylation engineering: influence of Golgi enzyme localization domain and co-expression of heterologous betal, 4-N-acetylglucosaminyltransferase III and Golgi alpha-mannosidase II," Biotechnol. Bioeng., 93(5):851-861.

Ferrara et al., 2006, "The carbohydrate at FcgammaRIIIa Asn-162. An element required for high affinity binding to non-fucosylated IgG glycoforms" J. Biol. Chem., 281(8):5032-5036 (Epub 2005).

GenBank Accession No. NP_001120972.1, "hepatocyte growth factor receptor isoform a preproprotein [*Homo sapiens*]," Mar. 17, 2022 (4 pages).

GenBank Accession No. NP_005219.2, "epidermal growth factor receptor isoform a precursor [*Homo sapiens*]," Feb. 20, 2022 (7 pages).

Graves et al., 1995, "Chemokines, a family of chemotactic cytokines," Crit. Rev. Oral Biol. Med., 6(2):109-118.

Hardbower et al., 2017, "EGFR-mediated macrophage activation promotes colitis-associated tumorigenesis," Oncogene., 36(27):3807-3819.

Honegger et al., 2001, "Yet another numbering scheme for immunoglobulin variable domains: an automatic modeling and analysis tool," J. Mol. Biol., 309(3):657-670.

Hong et al., 2017, "P3.02b-119: YH25448, a Highly Selective 3rd Generation EGFR TKI, Exhibits Superior Survival over Osimertinib in Animal Model with Brain Metastases from NSCLC," Journal of Thoracic Oncology, 12(1S):S1265-S1266).

Hynes et al., 2005, "ERBB receptors and cancer: the complexity of targeted inhibitors," Nat. Rev. Cancer, 5(5):341-354.

International Search Report and Written Opinion for International Patent Application No. PCT/IB2020/051559 (Pub No. WO 2020174370) dated Oct. 6, 2020 (16 pages).

International Search Report and Written Opinion for International Patent Application No. PCT/IB2020/054594 (Pub No. WO 2020230091) dated Sep. 4, 2020 (11 pages).

Janne et al., 2006, "Effect of epidermal growth factor receptor tyrosine kinase domain mutations on the outcome of patients with non-small cell lung cancer treated with epidermal growth factor receptor tyrosine kinase inhibitors," Clin, Cancer Res., 12(14 Pt 2):4416s-4420s.

Janson et al., 1991, "Production of IL-1 receptor antagonist by human in vitro-derived macrophages. Effects of lipopolysaccharide and granulocyte-macrophage colony-stimulating factor," J. Immunol., 147(12):4218-4223.

Jeffers et al., 1996, "Hepatocyte growth factor/scatter factor-Met signaling in tumorigenicity and invasion/metastasis," J. Mol. Med. (Berl), 74(9):505-513.

Jia et al., 2008, "Additive roles for MCP-1 and MCP-3 in CCR2-mediated recruitment of inflammatory monocytes during Listeria monocytogenes infection," J. Immunol., 180(10):6846-6853.

Kinder et al., 2015, "An Fc engineering approach that modulates antibody-dependent cytokine release without altering cell-killing functions," MAbs, 7(3):494-504.

Knappik et al., 2000, "Fully synthetic human combinatorial antibody libraries (HuCAL) based on modular consensus frameworks and CDRs randomized with trinucleotides," J. Mol. Biol., 296(1):57-86.

Kobayashi et al., 2005, "EGFR mutation and resistance of non-small-cell lung cancer to gefitinib," N. Engl. J. Med., 352(8):786-792.

Konno et al., 2012, "Fucose content of monoclonal antibodies can be controlled by culture medium osmolality for high antibody—dependent cellular cytotoxicity," Cytotechnology, 64(3):249-265 (Epub 2011).

Lefranc et al., 2003, "IMGT unique numbering for immunoglobulin and T cell receptor variable domains and Ig superfamily V-like domains," Dev. Comp. Immunol., 27(1):55-77.

Loetscher et al., 1994, "Monocyte chemotactic proteins MCP-1, MCP-2, and MCP-3 are major attractants for human CD4+ and CD8+ T lymphocytes," FASEB J., 8(13):1055-1060.

Martin et al., 1996, "Structural families in loops of homologous proteins: automatic classification, modelling and application to antibodies," J. Mol. Biol., 263(5):800-815.

Martinelli et al., 2009, "Anti-epidermal growth factor receptor monoclonal antibodies in cancer therapy," Clin. Exp. Immunol., 158(1):1-9.

Metlung et al., 2018, "Neutrophils Kill Antibody-Opsonized Cancer Cells by Trogoptosis," Cell Rep., 23(13):3946-3959.e1-e6.

Mori et al., 2004, "Engineering Chinese hamster ovary cells to maximize effector function of produced antibodies using FUT8 siRNA," Biotechnol. Bioeng., 88(7):901-908.

Nakata et al., 2012, "Recent understanding of the molecular mechanisms for the efficacy and resistance of EGF receptor-specific tyrosine kinase inhibitors in non-small cell lung cancer," Expert Opin. Ther. Targets, 16(8):771-781.

Olivier et al., 2010, "EB66 cell line, a duck embryonic stem cell-derived substrate for the industrial production of therapeutic monoclonal antibodies with enhanced ADCC activity," MAbs, 2(4):405-415.

Pao et al., 2005, "Acquired resistance of lung adenocarcinomas to gefitinib or erlotinib is associated with a second mutation in the EGFR kinase domain," PLoS Med., 2(3):e73 (11 pages).

Perez-Soler et al., 2004, "Determinants of tumor response and survival with erlotinib in patients with non-small-cell lung cancer," J. Clin. Oncol., 22(16):3238-3247.

Pham et al., 2011, "Dynamics of macrophage trogocytosis of rituximab-coated B cells," PLoS One, 6(1):e14498 (11 pages).

PubChem. CID 121269225, Aug. 6, 2016, pp. 1-19; retreived from the internet <URL:https://pubchem.ncbi.nim.nih.gov/compound/121269225>; p. 2, formula (19 pages).

(56) References Cited

OTHER PUBLICATIONS

Sequist et al., 2011, "Genotypic and histological evolution of lung cancers acquiring resistance to EGFR inhibitors," Sci. Transl. Med., 3(75):75ra26 (13 pages).

Shi et al., 2010, "De novo selection of high-affinity antibodies from synthetic fab libraries displayed on phage as pIX fusion proteins," J. Mol. Biol., 397(2):385-396.

Shields et al., 2002, "Lack of fucose on human IgG1 N-linked oligosaccharide improves binding to human Fcgamma RIII and antibody-dependent cellular toxicity," J. Biol. Chem., 277(30):26733-26740.

Shinkawa et al., 2003, "The absence of fucose but not the presence of galactose or bisecting N-acetylglucosamine of human IgG1 complex-type oligosaccharides shows the critical role of enhancing antibody-dependent cellular cytotoxicity," J. Biol, Chem., 278(5):3466-3473 (Epub 2002).

Taylor et al., 2015, "Fcγ-receptor-mediated trogocytosis impacts mAb-based therapies: historical precedence and recent developments," Blood, 125(5):762-766 (Epub 2014).

Turke et al., 2010, "Preexistence and clonal selection of MET amplification in EGFR mutant NSCLC," Cancer Cell, 17(1):77-88.

U.S. National Library of Meicine, "Study of JNJ-61186372, a Human Bispecific EGFR and cMet Antibody, in Subjects With Advanced Non-Small Cell Lung Cancer," Aug. 14, 2020, ClinicalTrials.gov Identifier: NCT02609776 (14 pages).

Uguccioni et al., 1995, "Actions of the chemotactic cytokines MCP-1, MCP-2, MCP-3, RANTES, MIP-1 alpha and MIP-1 beta on human monocytes," Eur. J. Immunol., 25(1):64-68.

Ullrich et al., 1984, "Human epidermal growth factor receptor cDNA sequence and aberrant expression of the amplified gene in A431 epidermoid carcinoma cells," Nature, 309(5967):418-425.

Velmurugan et al., 2016, "Macrophage-Mediated Trogocytosis Leads to Death of Antibody-Opsonized Tumor Cells," Mol. Cancer Ther., 15(8):1879-1889.

Wu et al., 1970, "An analysis of the sequences of the variable regions of Bence Jones proteins and myeloma light chains and their implications for antibody complementarity," J. Exp. Med., 132(2):211-250.

Yano et al., 2008, "Hepatocyte growth factor induces gefitinib resistance of lung adenocarcinoma with epidermal growth factor receptor-activating mutations," Cancer Res., 68(22):9479-9487.

Yun et al., 2008, "The T790M mutation in EGFR kinase causes drug resistance by increasing the affinity for ATP," Proc. Natl. Acad. Sci. USA, 105(6):2070-2075.

Zhou et al., 2008, "Development of a simple and rapid method for producing non-fucosylated oligomannose containing antibodies with increased effector function," Biotechnol. Bioeng., 99(3):652-665.

\* cited by examiner

- ■ H1975 - JNJ372 - no PBMC
- ■ H1975 - JNJ372 - PBMC -> IC50 = 0.0066 ug/ml
- ▲ H1975 - Iso - no PBMC
- ▲ H1975 - Iso - PBMC
- ▼ H1975 - IgG2s - no PBMC
- ▼ H1975 - IgG2s - PBMC -> IC50 = 17.63 ug/ml
- ◆ H1975 - EGFRxMet NF - no PBMC
- ◆ H1975 - EGFRxMet NF - PBMC -> IC50 = 5.403 ug/ml

US 11,459,391 B2

COMBINATION THERAPIES AND PATIENT STRATIFICATION WITH BISPECIFIC ANTI-EGFR/C-MET ANTIBODIES

CROSS-REFERENCE TO RELATED APPLICATIONS

This application claims the benefit of U.S. Provisional Application Ser. No. 62/930,190 filed Nov. 4, 2019 and U.S. Provisional Application Ser. No. 62/810,716 filed Feb. 26, 2019, the entire contents of which are incorporated herein by reference.

FIELD OF THE INVENTION

The present invention relates to combination therapies and patient stratification with bispecific anti-EGFR/c-Met antibodies

SEQUENCE LISTING

This application contains a Sequence Listing submitted via EFS-Web, the entire content of which is incorporated herein by reference. The ASCII text file, created on Feb. 13, 2020, is named JBI6051USNP1ST25.txt and is 19 kilobytes in size.

BACKGROUND OF THE INVENTION

The individual roles of both EGFR and c-Met in cancer is well established, making these targets attractive for combination therapy. Both receptors signal through the same survival and anti-apoptotic pathways (ERK and AKT); thus, inhibiting the pair in combination may limit the potential for compensatory pathway activation thereby improving overall efficacy.

Relapse or resistance to existing therapeutics is common Hence, there is a need for improved therapeutics or combination of therapeutics and patient stratification biomarkers to develop more effective treatment of a disease, such as EGFR or c-Met positive cancer

SUMMARY OF THE INVENTION

The disclosure provides a method of treating a subject having an EGFR or c-Met expressing cancer, comprising administering a therapeutically effective amount of an isolated bispecific anti-epidermal growth factor receptor (EGFR)/hepatocyte growth factor receptor (c-Met) antibody to the subject in combination with an agent that enhances macrophage activity in the subject.

The disclosure also provides a method of diagnosing and treating a subject having an EGFR or c-Met expressing cancer that is responsive to treatment with a bispecific anti-EGFR/c-Met antibody, comprising: providing a biological sample from the subject; measuring macrophage or monocyte levels from the biological sample; diagnosing the subject having the EGFR or c-Met expressing cancer that is responsive to treatment with the bispecific anti-EGFR/c-Met antibody when the macrophage or monocyte levels from the biological sample are higher than a threshold value; and administering or providing for administration the bispecific anti-EGFR/c-Met antibody to the subject diagnosed as responsive to treatment with the anti-EGFR/c-Met antibody.

The disclosure also provides a method of treating a subject suspected to have or having an EGFR or c-Met expressing cancer with a bispecific anti-EGFR/c-Met antibody, comprising: determining that the subject has macrophage or monocyte levels higher than a threshold value; and administering or providing for administration the bispecific anti-EGFR/c-Met antibody to the subject determined to have macrophage or monocyte levels higher than the threshold value.

The disclosure also provides a method of predicting response of a subject having an EGFR or c-Met expressing cancer to treatment with a bispecific anti-EGFR/c-Met antibody, comprising providing a biological sample from the subject; measuring macrophage or monocyte levels from the biological sample; predicting the subject as a responder when the macrophage or monocyte levels from the biological sample are higher than a threshold value.

The disclosure also provides a method of treating a subject having an EGFR or c-Met expressing cancer that is responsive to treatment with a bispecific anti-EGFR/c-Met antibody, comprising providing a biological sample from the subject; measuring macrophage or monocyte levels from the biological sample; treating the subject with the bispecific anti-EGFR/c-Met antibody when the macrophage or monocyte levels from the biological sample are higher than a threshold value.

The disclosure also provides a method of determining whether a subject having an EGFR or c-Met expressing cancer is responsive to treatment with a bispecific anti-EGFR/c-Met antibody and deciding whether to treat the subject, comprising: providing a biological sample from the subject; measuring macrophage or monocyte levels from the biological sample; diagnosing the subject with the EGFR or c-Met expressing cancer as responsive to treatment with the bispecific anti-EGFR/c-Met antibody when macrophage or monocyte levels from the biological sample are higher than a threshold value or diagnosing the subject with the EGFR or c-Met expressing cancer as non-responsive to treatment with the bispecific anti-EGFR/c-Met antibody when macrophage or monocyte levels from the biological sample are below the threshold value; and administering the bispecific anti-EGFR/c-Met antibody the subject diagnosed as responsive to treatment with the bispecific anti-EGFR/c-Met antibody or refraining from administering the bispecific anti-EGFR/c-Met antibody to the subject diagnosed as non-responsive to treatment with the bispecific anti-EGFR/c-Met antibody.

BRIEF DESCRIPTION OF THE DRAWINGS

The patent or patent application file contains at least one drawing executed in color. Copies of this patent or patent application publication with color drawings will be provided by the United States Patent and Trademark Office upon request and payment of the necessary fees.

DETAILED DESCRIPTION OF THE INVENTION

Definitions

Figure 1:
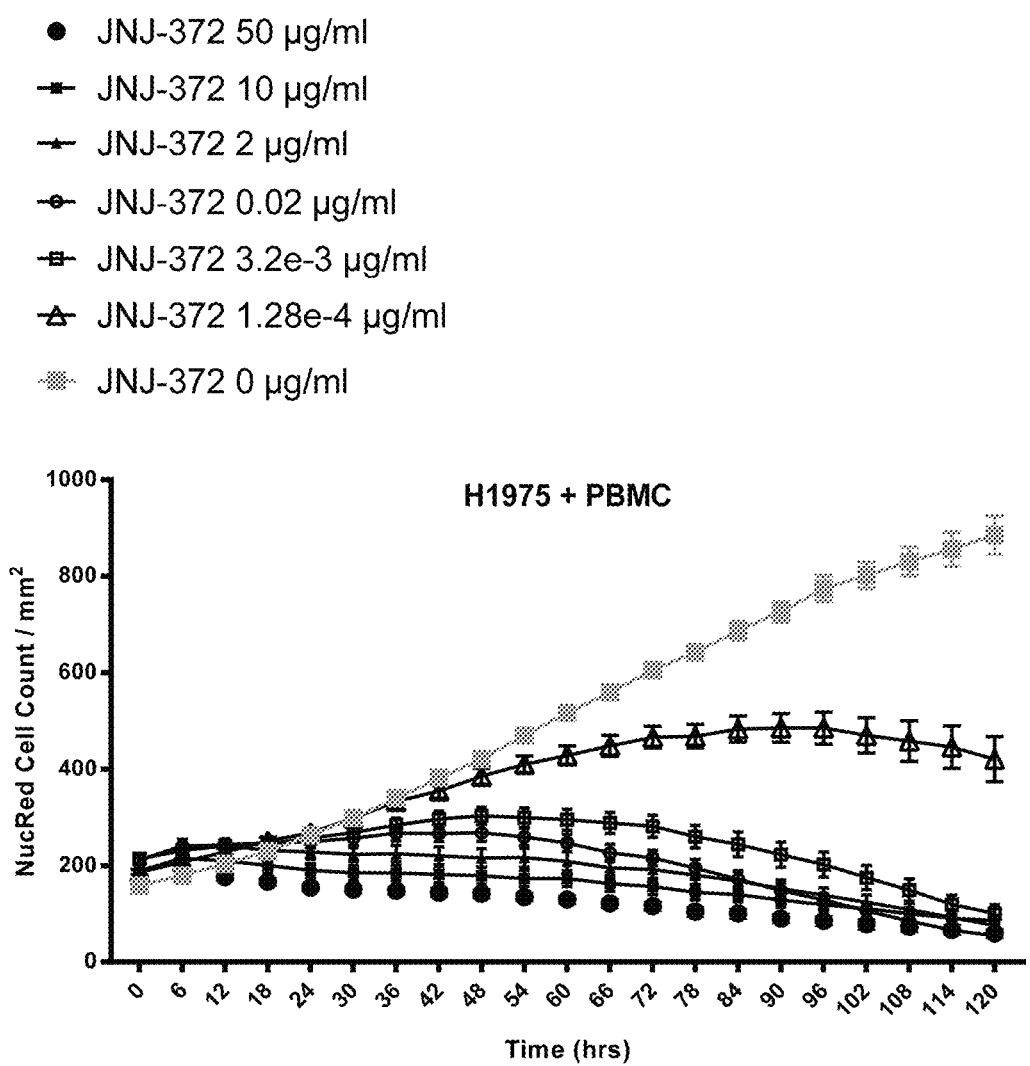
FIG. 1 shows JNJ-372 mediated inhibition of proliferation of NucLight Red labeled NCI-H1975 cells in the presence of PBMCs at indicated JNJ-372 concentrations in cultures up to 120 hours as measured using NucLight Red cell count/mm$^2$.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used in this specification and the appended claims, the singular forms "a," "an," and "the" include plural referents unless the content clearly dictates otherwise. Thus, for example, reference to "a cell" includes a combination of two or more cells, and the like.

The conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of"

"Co-administration," "administration with," "administration in combination with," "in combination with" or the like, encompass administration of the selected therapeutics or drugs to a single patient, and are intended to include treatment regimens in which the therapeutics or drugs are administered by the same or different route of administration or at the same or different time.

"Isolated" refers to a homogenous population of molecules (such as synthetic polynucleotides, polypeptides vectors or viruses) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Prevent", "preventing", "prevention", or "prophylaxis" of a disease or disorder means preventing that a disorder occurs in subject.

"Diagnosing" or "diagnosis" refers to methods to determine if a subject is suffering from a given disease or condition or may develop a given disease or condition in the future or is likely to respond to treatment for a prior diagnosed disease or condition, i.e., stratifying a patient population on likelihood to respond to treatment. Diagnosis is typically performed by a physician based on the general guidelines for the disease to be diagnosed or other criteria that indicate a subject is likely to respond to a particular treatment.

"Responsive", "responsiveness" or "likely to respond" refers to any kind of improvement or positive response, such as alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

"Newly diagnosed" refers to a subject who has been diagnosed with EGFR or c-Met expressing cancer but has not yet received treatment for multiple myeloma.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Refractory" refers to a disease that does not respond to a treatment. A refractory disease can be resistant to a treatment before or at the beginning of the treatment, or a refractory disease can become resistant during a treatment.

"Relapsed" refers to the return of a disease or the signs and symptoms of a disease after a period of improvement after prior treatment with a therapeutic.

"Subject" includes any human or nonhuman animal "Nonhuman animal" includes all vertebrates, e.g., mammals and non-mammals, such as nonhuman primates, sheep, dogs, cats, horses, cows, chickens, amphibians, reptiles, etc. The terms "subject" and "patient" are used interchangeably herein.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Cancer" refers to an abnormal growth of cells which tend to proliferate in an uncontrolled way and, in some cases, to metastasize (spread) to other areas of a patient's body.

"EGFR or c-Met expressing cancer" refers to cancer that has detectable expression of EGFR or c-Met or has EGFR or c-Met mutation or amplification. EGFR or c-Met expression, amplification and mutation status can be detected using know methods, such as sequencing, fluorescent in situ hybridization, immunohistochemistry, flow cytometry or western blotting.

"Epidermal growth factor receptor" or "EGFR" refers to the human EGFR (also known as HER1 or ErbB1 (Ullrich et al., *Nature* 309:418-425, 1984) having the amino acid sequence shown in GenBank accession number NP_005219, as well as naturally-occurring variants thereof.

"Hepatocyte growth factor receptor" or "c-Met" as used herein refers to the human c-Met having the amino acid sequence shown in GenBank Accession No: NP_001120972 and natural variants thereof.

"Bispecific anti-EGFR/c-Met antibody" or "bispecific EGFR/c-Met antibody" refers to a bispecific antibody having a first domain that specifically binds EGFR and a second domain that specifically binds c-Met. The domains specifically binding EGFR and c-Met are typically VH/VL pairs, and the bispecific anti-EGFR/c-Met antibody is monovalent in terms of binding to EGFR and c-Met.

"Specific binding" or "specifically binds" or "specifically binding" or "binds" refer to an antibody binding to an antigen or an epitope within the antigen with greater affinity than for other antigens. Typically, the antibody binds to the antigen or the epitope within the antigen with an equilibrium dissociation constant ($K_D$) of about $5 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the $K_D$ that is at least one hundred-fold less than its $K_D$ for binding to a non-specific antigen (e.g., BSA, casein). The dissociation constant may be measured using known protocols. Antibodies that bind to the antigen or the epitope within the antigen may, however, have cross-reactivity to other related antigens, for example to the same antigen from other species (homologs), such as human or monkey, for example *Macaca fascicularis* (cynomolgus, cyno) or *Pan troglodytes* (chimpanzee, chimp). While a monospecific antibody binds one antigen or one epitope, a bispecific antibody binds two distinct antigens or two distinct epitopes.

"Antibodies" is meant in a broad sense and includes immunoglobulin molecules including monoclonal antibodies including murine, human, humanized and chimeric monoclonal antibodies, antigen binding fragments, multi-specific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions" (CDR) are antibody regions that bind an antigen. CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) *J Mol Biol* 196: 901-17), IMGT (Lefranc et al. (2003) *Dev Comp Immunol* 27: 55-77) and AbM (Martin and Thornton (1996) *J Bmol Biol* 263: 800-15). The correspondence between the various delineations and variable region numbering are described (see e.g. Lefranc et al. (2003) *Dev Comp Immunol* 27: 55-77; Honegger and Pluckthun, (2001) *J Mol Biol* 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody"

"Recombinant" refers to DNA, antibodies and other proteins that are prepared, expressed, created or isolated by recombinant means when segments from different sources are joined to produce recombinant DNA, antibodies or proteins.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Multispecific" refers to an antibody that specifically binds two or more distinct antigens or two or more distinct epitopes within the same antigen. The multispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Macrophage" designates a cell of myeloid origin. Macrophages are large white blood cells, occurring principally in connective tissue and in the bloodstream or resident to a tissue or tumor microenvironment. They ingest foreign particles and infectious microorganisms by phagocytosis and have the capacity for antigen presentation. Unactivated macrophages derived from precursors undergo specific differentiation depending on the local tissue environment. They respond to environmental cues within tissues such as damaged cells, activated lymphocytes, or microbial products, to differentiate into distinct functional phenotypes. For instance, monocytes in the blood can enter the tissue during inflammation or insult and are, depending on the local microenvironment, polarized towards an M1 or M2 phenotype. The M1 macrophage phenotype is characterized by the production of high levels of pro-inflammatory cytokines, an ability to mediate resistance to pathogens, strong microbicidal properties, high production of reactive nitrogen and oxygen intermediates, promotion of Th1 responses and killing of pathogens and tumor cells. In contrast, M2 macrophages are characterized by their involvement in parasite control, tissue remodeling, immune regulation, tumor promotion and efficient phagocytic activity. M2 macrophages are further subcategorized to four different subtypes referred to as M2a, M2b, M2c and M2d. "Macrophage" includes all macrophage subtypes.

"Monocyte" refers to the $CD14^+CD34^-$ mononuclear white cell, belonging to a type of white blood cell involved in first-line defensive mechanisms and is recognized as able to differentiate into a dendritic cell or macrophage precursor. Monocyes normally move in the blood system. In response to external stimulating signals, monocytes secrete many immunoregulator cytokines, move to the site of infection in the tissue or to a site of tumor, and differentiate into macrophages. In particular, a monocyte expresses elevated levels of the CD14 surface antigen marker, and may express at least one biomarker selected from CD64, CD93, CD180, CD328, CD329 or peanut agglutinin protein (PNA).

"Enhance" or "induce" refers to potentiation of one or more function or activity of a macrophage by more than 10%, 20%, 30%, 40%, 50%, 60%, 70%, 75%, 80%, 85%, 90%, 95%, 96%, 97%, 98%, 99% or 100%, or by a statistically significant manner when compared to a control (e.g., potentiation in the presence or absence of an agent that enhances macrophage activity).

"Enhance macrophage activity" refers to a potentiation of one or more macrophage activities, inducing a phenotypic change in monocytes and/or macrophage differentiation of monocytes to macrophages, or activating non-activated macrophages.

"Macrophage activity" refers to any macrophage functionality, such as phagocytosis, antigen presentation, production of IL-12, IL-1, TNFcc or production of inflammatory chemokines such as CXCL1, CXCL2, CXCL3, CXCLS, CXCL8, CXCL9, CXCL10, CCL2, CCL3, CCL4, CCL11, CCL17, CCL22.

"Agent that enhances macrophage activity" can be a small molecule, a peptide, an oligopeptide, a polypeptide, a protein, an antibody, a synthetic binding molecule, an aptamer, an RNA molecule, a DNA molecule, an oligomer, a polymer, a lipid, or a liposome. Exemplary agents that enhance macrophage function include cytokines, chemokines, partem recognition receptor ligands, hormones, adrenergic and cholinergic agonists, fatty acids, phospholipids, immunoglobulins or portions thereof, Fc domains of immunoglobulins, lipopolysaccharides (LPS), toll-like receptor (TLR) ligands, histamines, and peroxisome proliferator-activated receptor ligands.

"Trogocytosis" refers to a process characterized by the transfer of a portion of a cell membrane from a donor cell to an acceptor cell. Typical acceptor cells include macrophages and monocytes. Additional acceptor cells include NK cells, dendritic cells, T cells, B cells and neutrophils. Trogocytosis-mediated transfer of a portion of a cell membrane may include transfer of membrane proteins, for example such as EGFR or c-Met, or antibody-antigen complexes where an antibody is bound to the cell surface molecule. Antibody-mediated trogocytosis may occur via binding fo the Fc portion of the antibody to the Fcγ receptor (FcγR) expressed on acceptor cells.

"Anti-EGFR/c-Met antibody mediated trogocytosis" refers to trogocytosis of EGFR and/or c-Met containing portions of a cell membrane from a donor cell to an acceptor cell mediated by the anti-EGFR/c-Met antibody bound to donor cell membrane EGFR and/or c-Met.

"Threshold" refers to the level of macrophages or monocytes that is about the $30^{th}$ percentile value or above of macrophages or monocytes observed in the biological sample from a population of subjects having the EGFR or c-Met positive cancer.

"Agonist" refers to a molecule that, when bound to a cellular protein, induces at least one reaction or activity that is induced by a natural ligand of the protein. The molecule is an agonist when the at least one reaction or activity is induced by at least about 20%, 30%, 40%, 45%, 50%, 55%, 60%, 65%, 70%, 75%, 80%, 85%, 90%, 95%, or 100% greater than the at least one reaction or activity induced in the absence of the agonist (e.g., negative control), or when the induction is statistically significant when compared to the induction in the absence of the agonist.

"Antagonist" or "inhibitor" refers to a molecule that, when bound to a cellular protein, suppresses at least one reaction or activity that is induced by a natural ligand of the protein. A molecule is an antagonist when the at least one reaction or activity is suppressed by at least about 20%, 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist.

"PD-(L)1 axis inhibitor" refers to a molecule that inhibits PD-1 downstream signaling. PD-(L)1 axis inhibitor may be a molecule that binds PD-1, PD-L1 or PD-L2.

"Biological sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium, lavage fluids and the like, tissue biopsies, tumor tissue biopsies, tumor tissue samples, fine needle aspirations, surgically resected tissue, organ cultures or cell cultures.

"Low fucose" or "low fucose content" as used in the application refers to antibodies with fucose content of about between 1%-15%.

"Normal fucose" or "normal fucose content" as used herein refers to antibodies with fucose content of about over 50%, typically about over 80% or over 85%.

Methods of the Disclosure

JNJ-61186372 (JNJ-372) is an IgG1 anti-EGFR/c-Met bispecific antibody described in U.S. Pat. No. 9,593,164. Earlier studies indicated that JNJ-372 inhibited tumor growth and progression by three distinct mechanisms: inhibition of ligand-induced activation via blocking ligand binding to each receptor, receptor inactivation via degradation and Fc effector-mediated killing of EGFR- and c-Met-expressing tumors by ADCC and ADCP (Moores et al., Cancer Research 76(13), 2016.; published online May 23, 2016; DOI: 10.1158/0008-5472).

The invention is based, at least in part, on the surprising finding that JNJ-372 Fc interaction not only mediates ADCC and ADCP but also potentiates JNJ-372 mediated inhibition of EGFR/c-Met signaling, and that monocytes or macrophages are sufficient and necessary for JNJ-372 mediated anti-tumor effects through trogocytosis.

By not wishing to be bound by any theory, it may be expected, based on the surprising results disclosed herein, that levels of monocytes in patient blood may positively correlate with the levels of macrophages in their tumors, which may predict better response to JNJ-372. Similarly, it may be expected that tumor tissue samples with increased levels of macrophages or increased levels of FcγRI or FcγRIIIa by IHC or immune gene signature would respond better to JNJ-372 by providing more immune cell interactions. Also, it may be expected, based on the results described herein, that treatments that enhance macrophage activity used in combination with JNJ-372 would increase overall efficacy of JNJ-372. For example, treatment with GM-CSF would drive differentiation of circulating monocytes into tumor-associated macrophages, which may increase JNJ-372 efficacy. Treatment with anti-CD47 therapy may block the negative inhibition of macrophages, thus activating them to enhance JNJ-372 activity. Similarly, inhibition of PD-(L)1 axis, inhibition of HDAC or agnoizing CD11b may shift the polarization of tumor-associated macrophages such that they are more active and thus would synergize with JNJ-372 treatment to enhance tumor killing.

The identification of this new mechanism provides basis for selecting patients for treatment who may be more responsive to JNJ-372 based on the patient's relative or absolute monocyte and/or macrophage amount in blood or tumor sample and for combination treatment methods using molecules that enhance macrophage activity in combination with JNJ-372.

The disclosure provides a method of treating a subject having an EGFR or c-Met expressing cancer, comprising administering a therapeutically effective amount of an isolated bispecific epidermal growth factor receptor (EGFR)/hepatocyte growth factor receptor (c-Met) antibody to the subject in combination with an agent that enhances macrophage activity in the subject.

The disclosure also provides a method of diagnosing and treating a subject having an EGFR or c-Met expressing cancer that is responsive to treatment with a bispecific anti-EGFR/c-Met antibody, comprising: providing a biological sample from the subject; measuring macrophage or monocyte levels from the biological sample; diagnosing the subject having the EGFR or c-Met expressing cancer that is responsive to treatment with the bispecific anti-EGFR/c-Met antibody when the macrophage or monocyte levels from the biological sample are higher than a threshold value; and administering or providing for administration the bispecific anti-EGFR/c-Met antibody to the subject diagnosed as responsive to treatment with the anti-EGFR/c-Met antibody.

The disclosure also provides a method of treating a subject suspected to have or having an EGFR or c-Met expressing cancer with a bispecific anti-EGFR/c-Met antibody, comprising: determining that the subject has macrophage or monocyte levels higher than a threshold value; and administering or providing for administration the bispecific anti-EGFR/c-Met antibody to the subject determined to have macrophage or monocyte levels higher than the threshold value.

The disclosure also provides a method of predicting response of a subject having an EGFR or c-Met expressing cancer to treatment with a bispecific anti-EGFR/c-Met antibody, comprising providing a biological sample from the subject; measuring macrophage or monocyte levels from the biological sample; predicting the subject as a responder when the macrophage or monocyte levels from the biological sample are higher than a threshold value.

The disclosure also provides a method of treating a subject having an EGFR or c-Met expressing cancer that is responsive to treatment with a bispecific anti-EGFR/c-Met antibody, comprising providing a biological sample from the subject; measuring macrophage or monocyte levels from the biological sample; treating the subject with the bispecific anti-EGFR/c-Met antibody when the macrophage or monocyte levels from the biological sample are higher than a threshold value.

The disclosure also provides a method of determining whether a subject having an EGFR or c-Met expressing cancer is responsive to treatment with a bispecific anti-EGFR/c-Met antibody and deciding whether to treat the subject, comprising: providing a biological sample from the subject; measuring macrophage or monocyte levels from the biological sample; diagnosing the subject with the EGFR or c-Met expressing cancer as responsive to treatment with the bispecific anti-EGFR/c-Met antibody when macrophage or monocyte levels from the biological sample are higher than a threshold value or diagnosing the subject with the EGFR or c-Met expressing cancer as non-responsive to treatment with the bispecific anti-EGFR/c-Met antibody when macrophage or monocyte levels from the biological sample are below the threshold value; and administering the bispecific anti-EGFR/c-Met antibody the subject diagnosed as responsive to treatment with the bispecific anti-EGFR/c-Met antibody or refraining from administering the bispecific anti-EGFR/c-Met antibody to the subject diagnosed as non-responsive to treatment with the bispecific anti-EGFR/c-Met antibody.

"Level" of macrophages or monocytes may be qualitative (e.g., presence or absence) or quantitative (e.g., absolute cell numbers, relative numbers, percent (%) from a total cell count or % positive cells in a field). In some embodiments, macrophages or monocytes are absent in the biological sample. In some embodiments, the level of macrophages or monocytes is above the mean value of macrophages or monocytes observed in a biological sample from a healthy subject. In some embodiments, the level of macrophages or monocytes is about the $30^{th}$ percentile value of macrophages or monocytes observed in the biological sample from subjects having the EGFR or c-Met positive cancer. In some embodiments, the level of macrophages or monocytes is about the $35^{th}$ percentile value of macrophages or monocytes observed in the biological sample from subjects having the EGFR or c-Met positive cancer. In some embodiments, the level of macrophages or monocytes is about the $40^{th}$ percentile value of macrophages or monocytes observed in the biological sample from subjects having the EGFR or c-Met positive cancer. In some embodiments, the level of macrophages or monocytes is about the $45^{th}$ percentile value of macrophages or monocytes observed in the biological sample from subjects having the EGFR or c-Met positive cancer. In some embodiments, the level of macrophages or monocytes is about the $50^{th}$ percentile value of macrophages or monocytes observed in the biological sample from subjects having the EGFR or c-Met positive cancer. In some embodiments, the level of macrophages or monocytes is about the $60^{th}$ percentile value of macrophages or monocytes observed in the biological sample from subjects having the EGFR or c-Met positive cancer. In some embodiments, the level of macrophages or monocytes is about the $65^{th}$ percentile value of macrophages or monocytes observed in the biological sample from subjects having the EGFR or c-Met positive cancer. In some embodiments, the level of macrophages or monocytes is about the $70^{th}$ percentile value of macrophages or monocytes observed in the biological sample from subjects having the EGFR or c-Met positive cancer. In some embodiments, the level of macrophages or monocytes is about the $75^{th}$ percentile value of macrophages or monocytes observed in the biological sample from subjects having the EGFR or c-Met positive cancer. In some embodiments, the level of macrophages or monocytes is about the $80^{th}$ percentile value of macrophages or monocytes observed in the biological sample from subjects having the EGFR or c-Met positive cancer. In some embodiments, the level of macrophages or monocytes is about the $85^{th}$ percentile value of macrophages or monocytes observed in the biological sample from subjects having the EGFR or c-Met positive cancer. In some embodiments, the level of macrophages or monocytes is about the $90^{th}$ percentile value of macrophages or monocytes observed in the biological sample from subjects having the EGFR or c-Met positive cancer. In some embodiments, the level of macrophages or monocytes is about the 95$^{th}$ percentile value of macrophages or monocytes observed in the biological sample from subjects having the EGFR or c-Met positive cancer. In some embodiments, the level of macrophages or monocytes is about the 100$^{th}$ percentile value of macrophages or monocytes observed in the biological sample from subjects having the EGFR or c-Met positive cancer.

Level of macrophages or monocytes in subjects having EGFR or c-Met expressing cancer may also be compared relative to the levels of macrophages or monocytes in the biological sample from healthy subjects. The increased level of macrophages or monocytes may for example be about 1.5-fold, about 2-fold, about 2.5-fold, about 3-fold, about 3.5-fold, about 4-fold, about 4.-fold, about 5-fold, about 5.5-fold, about 6-fold, about 6.5-fold, about 7-fold, about 7.5-fold, about 8-fold, about 8.5-fold, about 9-fold or about 10-fold higher when compared to the levels of macrophages or monocytes in the biological sample from healthy subjects.

Macrophages may be identified from for example tumor tissue biopsies obtained from subjects having the EGFR or c-Met expressing tumor using immunohistochemistry using CD68, iNOS (inducible nitric oxide synthase) and CD163 as markers for macrophages in general, M1 macrophages or M2 macrophages, respectively and evaluating percentage of area of positive staining and comparing to non-tumor tissue (see e.g., Almatoodi et al., *Cancer Micreoenvironment* 9:1-11, 2016 in which was described that % area of positive staining of CD68 was increased by 2-fold in non-tumor vs. adenocarcinoma, squamous cell or large cell carcinoma). Macrophages may be identified from for example tumor tissue biopsies obtained from subjects having the EGFR or c-Met expressing tumor using an immune gene signature.

Monocytes may be identified from blood samples from the subjects having the EGFR or c-Met expressing tumors using fluorescent cell sorting using monocyte marker CD14.

In some embodiments, the biological sample is a blood sample.

In some embodiments, the biological sample is a tumor tissue biopsy

Similarly, levels of FcγRI or FcγRIIIa may be used to predict patient response to JNJ-372 by providing more immune cell interactions.

In some embodiments, the level of FcγRI or FcγRIIIa is above the mean value of the level of FcγRI or FcγRIIIa observed in a biological sample from a healthy subject. In some embodiments, the level of FcγRI or FcγRIIIa is about the 30$^{th}$ percentile value of the level of FcγRI or FcγRIIIa observed in the biological sample from subjects having the EGFR or c-Met positive cancer. In some embodiments, the level of FcγRI or FcγRIIIa is about the 35$^{th}$ percentile value of the level of FcγRI or FcγRIIIa observed in the biological sample from subjects having the EGFR or c-Met positive cancer. In some embodiments, the level of FcγRI or FcγRIIIa is about the 40$^{th}$ percentile value of the level of FcγRI or FcγRIIIa observed in the biological sample from subjects having the EGFR or c-Met positive cancer. In some embodiments, the level of FcγRI or FcγRIIIa is about the 45$^{th}$ percentile value of the level of FcγRI or FcγRIIIa observed in the biological sample from subjects having the EGFR or c-Met positive cancer. In some embodiments, the level of FcγRI or FcγRIIIa is about the 50$^{th}$ percentile value of the level of FcγRI or FcγRIIIa observed in the biological sample from subjects having the EGFR or c-Met positive cancer. In some embodiments, the level of FcγRI or FcγRIIIa is about the 60$^{th}$ percentile value of the level of FcγRI or FcγRIIIa observed in the biological sample from subjects having the EGFR or c-Met positive cancer. In some embodiments, the level of FcγRI or FcγRIIIa is about the 65$^{th}$ percentile value of the level of FcγRI or FcγRIIIa observed in the biological sample from subjects having the EGFR or c-Met positive cancer. In some embodiments, the level of FcγRI or FcγRIIIa is about the 70$^{th}$ percentile value of the level of FcγRI or FcγRIIIa observed in the biological sample from subjects having the EGFR or c-Met positive cancer. In some embodiments, the level of FcγRI or FcγRIIIa is about the 75$^{th}$ percentile value of the level of FcγRI or FcγRIIIa observed in the biological sample from subjects having the EGFR or c-Met positive cancer. In some embodiments, the level of FcγRI or FcγRIIIa is about the 80$^{th}$ percentile value of the level of FcγRI or FcγRIIIa observed in the biological sample from subjects having the EGFR or c-Met positive cancer. In some embodiments, the level of FcγRI or FcγRIIIa is about the 85$^{th}$ percentile value of the level of FcγRI or FcγRIIIa observed in the biological sample from subjects having the EGFR or c-Met positive cancer. In some embodiments, the level of FcγRI or FcγRIIIa is about the 90$^{th}$ percentile value of the level of FcγRI or FcγRIIIa observed in the biological sample from subjects having the EGFR or c-Met positive cancer. In some embodiments, the level of FcγRI or FcγRIIIa is about the 95$^{th}$ percentile value of the level of FcγRI or FcγRIIIa observed in the biological sample from subjects having the EGFR or c-Met positive cancer. In some embodiments, the level of FcγRI or FcγRIIIa is about the 100$^{th}$ percentile value of the level of FcγRI or FcγRIIIa observed in the biological sample from subjects having the EGFR or c-Met positive cancer.

The level of FcγRI or FcγRIIIa may be measured using immunohistochemistry on tumor tissue samples (such as fresh frozen or paraffin embedded tumor tissue sections. The level of FcγRI or FcγRIIIa may be expressed as percent (%) of FcγRI or FcγRIIIa cells within a microscope field. The level of FcγRI or FcγRIIIa may also be measured at the gene expression level using RNA isolated from tumor tissue samples, either as part of an immune gene signature panel, or as individual genes.

In some embodiments, the bispecific anti-EGFR/c-Met antibody comprises a first domain that binds EGFR comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6; and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

In some embodiments, the first domain that binds EGFR comprises a heavy chain variable domain (VH) of SEQ ID NO: 13 and a light chain variable domain (VL) of SEQ ID NO: 14; and the second domain that binds c-Met comprises the VH of SEQ ID NO: 15 and the VL of SEQ ID NO: 16.

In some embodiments, the bispecific anti-EGFR/c-Met antibody is an IgG1 isotype. Some variation exists within the IgG1 constant domain (e g. well-known allotypes), with variation at positions 214, 356, 358, 422, 431, 435 o 436 (residue numbering according to the EU numbering) (see e.g. IMGT Web resources; IMGT Repertoire (IG and TR); Proteins and alleles; allotypes). The bispecific anti-EGFR/c-Met antibody may be of any IgG1 allotype, such as G1m17, G1m3, G1m1, G1m2, G1m27 or G1m28.

In some embodiments, the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

In some embodiments, the agent that enhances macrophage activity is GM-CSF, A CD47 antagonist, an anti-CD47 antibody, a HDAC inhibitor, a PD-(L)1 axis inhibitor or a CD11b agonist.

In some embodiments, the agent that enhances macrophage activity is GM-CSF.

n some embodiments, the agent that enhances macrophage activity is the anti-CD47 antagonist.

In some embodiments, the agent that enhances macrophage activity is the anti-CD47 antibody.

In some embodiments, the agent that enhances macrophage activity is the HDAC inhibitor.

In some embodiments, the agent that enhances macrophage activity is the PD-(L)1 axis inhibitor.

In some embodiments, the agent that enhances macrophage activity is the CD11b agonist.

In some embodiments, the HDAC inhibitor is a HDAC2 inhibitor.

Exemplary CD47 antagonists are CD47 ligand-Fc fusions, such as SIRPα-Fc fusions, such as TTI621 and ani-CD47 antibodies.

Exemplary anti-CD47 antibodies are Hu5F9-G4, TI-061, TTI-622, AO-176, IBI-188, ALX-148, SRF-231, CC-90002 and anti-CD47 antibodies disclosed in Int. Pat. Publ. No. WO2016/081423.

Exemplary HDAC inhibitors are vorinostad, romidepsin, chidamide, panobinostat, belinostat, pracinostat, abexinostat, entinostat, vafidemstat, GSK-2879552, ricolinostat, iadademstat, domatinostat, resminostat, AZD-9468, nanatinostat, CG-200745, mocetinostat, INCB-59872, IMG-7289, tinostamustine, RDN-929, YM-753, HG-146, NBM-BMX, TAK-418, seclidemstat, CKD-504, CKD-506, CC-90011, KA-2507 and citarinostat.

Exemplary PD-(L)1 axis inhibitors are antibodies that bind PD-1 such as nivolumab (OPDIVO®), pembrolizumab (KEYTRUDA®), sintilimab, cemiplimab (LIBTAYO®), tripolibamab, tislelizumab, spartalizumab, camrelizumab, dostralimab, genolimzumab or cetrelimab, or antibodies that bind PD-L1, such as PD-L1 antibodies are envafolimab, atezolizumab (TECENTRIQ®), durvalumab (IMFINZI®) and avelumab (BAVENCIO®).

Marketed antibodies may be purchased via authorized distributor or pharmacy. The amino acid sequences structures of the small molecules can be found from USAN and/or INN submissions by the companies of from CAS registry.

In some embodiments, the EGFR or c-Met expressing cancer is associated with a wild-type EGFR, an EGFR activating mutation, an EGFR gene amplification, increased levels of circulating HGF, a wild-type c-Met, a c-Met activating mutation, a c-Met gene amplification or a mutant KRAS.

Exemplary EGFR activating mutations that may be associated with cancer include point mutations, deletion mutations, insertion mutations, inversions or gene amplifications that lead to an increase in at least one biological activity of EGFR, such as elevated tyrosine kinase activity, formation of receptor homodimers and heterodimers, enhanced ligand binding etc. Mutations can be located in any portion of an EGFR gene or regulatory region associated with an EGFR gene and include mutations in exon 18, 19, 20 or 21 or mutations in the kinase domain. Other examples of EGFR activating mutations are known in the art (see e.g., U.S. Pat. Publ. No. US2005/0272083). Information about EGFR and other ErbB receptors including receptor homo- and hetero-dimers, receptor ligands, autophosphorylation sites, and signaling molecules involved in ErbB mediated signaling is known in the art (see e.g., Hynes and Lane, Nature Reviews Cancer 5: 341-354, 2005).

In some embodiments, the EGFR activating mutation is L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between 5768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, or one or more deletions or one or more insertions in EGFR exon 20.

Exemplary c-Met activating mutations include point mutations, deletion mutations, insertion mutations, inversions or gene amplifications that lead to an increase in at least one biological activity of a c-Met protein, such as elevated tyrosine kinase activity, formation of receptor homodimers and heterodimers, enhanced ligand binding etc. Mutations can be located in any portion of the c-Met gene or regulatory regions associated with the gene, such as mutations in the kinase domain of c-Met. Exemplary c-Met activating mutations are mutations at residue positions N375, V13, V923, R175, V136, L229, 5323, R988, S1058/T1010 and E168. Methods for detecting EGFR and c-Met mutations or gene amplifications are well known.

In some embodiments, the mutant KRAS has a G12V, G12C or G12A substitution.

In some embodiments, the subject has a newly diagnosed EGFR or c-Met expressing cancer.

In some embodiments, the subject having the newly diagnosed EGFR or c-Met expressing cancer has one or more EGFR exon 20 mutation. Exon 20 mutations (insertion of one or more amino acids are generally resistant to EGFR tyrosine kinase inhibitors (TKI) (see. e.g. Int. Pat. Publ. No. WO2018/094225).

In some embodiments, the subject is resistant or has acquired resistance to treatment with a prior anti-cancer therapy.

In some embodiments, the prior anti-cancer therapy is chemotherapy, a targeted anti-cancer therapy or a kinase inhibitor.

In some embodiments, the kinase inhibitor is an inhibitor of EGFR, c-Met, HER2, HER3, HER4, VEGFR or AXL.

In some embodiments, the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

In some embodiments, the subject is resistant or has acquired resistance to an EGFR inhibitor. Exemplary EGFR inhibitors for which cancer may acquire resistance are anti-EGFR antibodies cetuximab (ERBITUX®), pantinumumab (VECTIBIX®), matuzumab, nimotuzumab, small molecule EGFR inhibitors erlotinib (TARCEVA®), gefitinib (IRESSA®), EKB-569 (pelitinib, irreversible EGFR TKI), pan-ErbB and other receptor tyrosine kinase inhibitors, lapatinib (EGFR and HER2 inhibitor), pelitinib (EGFR and HER2 inhibitor),vandetanib (ZD6474, ZACTIMA™, EGFR, VEGFR2 and RET TKI), PF00299804 (dacomitinib, irreversible pan-ErbB TKI), CI-1033 (irreversible pan-erbB TKI), afatinib (BIBW2992, irreversible pan-ErbB TKI), AV-412 (dual EGFR and ErbB2 inhibitor), EXEL-7647 (EGFR, ErbB2, GEVGR and EphB4 inhibitor), CO-1686 (irreversible mutant-selective EGFR TKI), AZD9291 (irreversible mutant-selective EGFR TKI),and HKI-272 (neratinib, irreversible EGFR/ErbB2 inhibitor).

Various qualitative and/or quantitative methods may be used to determine if a subject is resistant, has developed or is susceptible to developing a resistance to treatment with an anti-cancer therapy. Symptoms that may be associated with resistance to an anti-cancer therapy include a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to an anti-cancer therapy, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with cervical cancer may include abnormal bleeding, unusual heavy vaginal discharge, pelvic pain that is not related to the normal menstrual cycle, bladder pain or pain during urination, and bleeding between regular menstrual periods, after sexual intercourse, douching, or pelvic exam Symptoms associated with lung cancer may include persistent cough, coughing up blood, shortness of breath, wheezing chest pain, loss of appetite, losing weight without trying and fatigue. Symptoms for liver cancer may include loss of appetite and weight, abdominal pain, especially in the upper right part of abdomen that may extend into the back and shoulder, nausea and vomiting, general weakness and fatigue, an enlarged liver, abdominal swelling (ascites), and a yellow discoloration of the skin and the whites of eyes (jaundice). One skilled in oncology may readily identify symptoms associated with a particular cancer type.

In some embodiments, the EGFR or c-Met expressing cancer is an epithelial cell cancer, breast cancer, ovarian cancer, lung cancer, non-small cell lung cancer (NSCLC), lung adenocarcinoma, small cell lung cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC).

In some embodiments, the EGFR or c-Met expressing cancer is an epithelial cell cancer. In some embodiments, the EGFR or c-Met expressing cancer is breast cancer. In some embodiments, the EGFR or c-Met expressing cancer is ovarian cancer. In some embodiments, the EGFR or c-Met expressing cancer is lung cancer. In some embodiments, the EGFR or c-Met expressing cancer is non-small cell lung cancer (NSCLC). In some embodiments, the EGFR or c-Met expressing cancer is lung adenocarcinoma. In some embodiments, the EGFR or c-Met expressing cancer is small cell lung cancer. In some embodiments, the EGFR or c-Met expressing cancer is colorectal cancer. In some embodiments, the EGFR or c-Met expressing cancer is anal cancer. In some embodiments, the EGFR or c-Met expressing cancer is prostate cancer. In some embodiments, the EGFR or c-Met expressing cancer is kidney cancer. In some embodiments, the EGFR or c-Met expressing cancer is bladder cancer. In some embodiments, the EGFR or c-Met expressing cancer is head and neck cancer. In some embodiments, the EGFR or c-Met expressing cancer is pharynx cancer. In some embodiments, the EGFR or c-Met expressing cancer is cancer of the nose. In some embodiments, the EGFR or c-Met expressing cancer is pancreatic cancer. In some embodiments, the EGFR or c-Met expressing cancer is skin cancer. In some embodiments, the EGFR or c-Met expressing cancer is oral cancer. In some embodiments, the EGFR or c-Met expressing cancer is cancer of the tongue. In some embodiments, the EGFR or c-Met expressing cancer is esophageal cancer. In some embodiments, the EGFR or c-Met expressing cancer is vaginal cancer. In some embodiments, the EGFR or c-Met expressing cancer is cervical cancer. In some embodiments, the EGFR or c-Met expressing cancer is cancer of the spleen. In some embodiments, the EGFR or c-Met expressing cancer is testicular cancer. In some embodiments, the EGFR or c-Met expressing cancer is gastric cancer. In some embodiments, the EGFR or c-Met expressing cancer is cancer of the thymus. In some embodiments, the EGFR or c-Met expressing cancer is colon cancer. In some embodiments, the EGFR or c-Met expressing cancer is thyroid cancer. In some embodiments, the EGFR or c-Met expressing cancer is liver cancer. In some embodiments, the EGFR or c-Met expressing cancer is hepatocellular carcinoma (HCC). In some embodiments, the EGFR or c-Met expressing cancer is sporadic or hereditary papillary renal cell carcinoma (PRCC).

In some embodiments, NSCLC includes squamous cell carcinoma, adenocarcinoma, and large cell carcinoma. In some embodiments, cells of the NSCLC have an epithelial phenotype. In some embodiments, the NSCLC has acquired resistance to treatment with one or more EGFR inhibitors.

In NSCLC, specific mutations in the EGFR gene are associated with high response rates (70-80%) to EGFR tyrosine kinase inhibitors (EGFR-TKIs). A 5 amino acid deletion in exon 19 or the point mutation L858R in EGFR are associated with EGFR-TKI sensitivity (Nakata and Gotoh, Expert Opin Ther Targets 16:771-781, 2012). These mutations result in a ligand-independent activation of the EGFR kinase activity. Activating EGFR mutations occur in 10-30% of NSCLC patients and are significantly more common in East Asians, women, never smokers, and patients with adenocarcinoma histology (Janne and Johnson Clin Cancer Res 12(14 Suppl): 4416s-4420s, 2006). EGFR gene amplification is also strongly correlated with response after EGFR-TKI treatment (Cappuzzo et al., J Natl Cancer Inst 97:643-55, 2005). EGFR exon 20 insertions have been associated with EGFR TKI resistance.

Although the majority of NSCLC patients with EGFR mutations initially respond to EGFR TKI therapy, virtually all acquire resistance that prevents a durable response. 50-60% of patients acquire resistance due to a second-site point mutation in the kinase domain of EGFR (T790M). Nearly 60% of all tumors that become resistant to EGFR tyrosine kinase inhibitors increase c-Met expression, amplify the c-Met gene, or increase its only known ligand, HGF (Turke et al., Cancer Cell, 17:77-88, 2010).

In some embodiments, the subject is homozygous for phenylalanine at position 158 of CD16 or heterozygous for valine and phenylalanine at position 158 of CD16.

Subject homozygous for phenylalanine at position 158 of CD16 has a FcγRIIIa-158F/F genotype. Subject heterozygous for valine and pheynylalanine at position 158 of CD16 has a FcγRIIIa-158F/V genotype. CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277:26733-40, 2002).

In some embodiments, the bispecific anti-EGFR/c-Met antibody has reduced fucose content of about between 1% to about 10%. The bispecific anti-EGFR/c-Met antibody having reduced fucose content may be more efficacious in the treatment of patients with FcγRIIIa-158F/F or FcγRIIIa-158FN genotypes. Patients can be analyzed for their FcγRIIIa polymorphism using routine methods.

Antibodies with reduced fucose content can be made using different methods reported to lead to the successful expression of relatively high defucosylated antibodies bearing the biantennary complex-type of Fc oligosaccharides such as control of culture osmolality (Konno et al., Cytotechnology 64(:249-65, 2012), application of a variant CHO line Lec13 as the host cell line (Shields et al., J Biol Chem 277:26733-26740, 2002), application of a variant CHO line EB66 as the host cell line (Olivier et al., MAbs;2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng88:901-908, 2004), or coexpression of β-1,4-N-acetyl-glucosaminyltransferase III and Golgi α-mannosidase II or a potent alpha-mannosidase I inhibitor, kifunensine (Ferrara et al., J Biol Chem281:5032-5036, 2006, Ferrara et al., Biotechnol Bioeng 93:851-861, 2006; Xhou et al., Biotechnol Bioeng 99:652-65, 2008).

In some embodiments, the subject is further administering a third anti-cancer therapy.

In some embodiments, the third anti-cancer therapy is chemotherapy, a targeted anti-cancer therapy or a kinase inhibitor.

In some embodiments, the kinase inhibitor is an inhibitor of EGFR, c-Met, HER2, HER3, HER4, VEGFR or AXL. In some embodiments, the kinase inhibitor is an inhibitor of EGFR. In some embodiments, the kinase inhibitor is an inhibitor of c-Met. In some embodiments, the kinase inhibitor is an inhibitor of HER2. In some embodiments, the kinase inhibitor is an inhibitor of HER3. In some embodiments, the kinase inhibitor is an inhibitor of HER4. In some embodiments, the kinase inhibitor is an inhibitor of VEGFR. In some embodiments, the kinase inhibitor is an inhibitor of or AXL.

In some embodiments, the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

In some embodiments, the kinase inhibitor is erlotinib. In some embodiments, the kinase inhibitor is gefitinib. In some embodiments, the kinase inhibitor is lapatinib. In some embodiments, the kinase inhibitor is vandetanib. In some embodiments, the kinase inhibitor is afatinib. In some embodiments, the kinase inhibitor is osimertinib. In some embodiments, the kinase inhibitor is lazertinib. In some embodiments, the kinase inhibitor is poziotinib. In some embodiments, the kinase inhibitor is criotinib. In some embodiments, the kinase inhibitor is cabozantinib. In some embodiments, the kinase inhibitor is capmatinib. In some embodiments, the kinase inhibitor is axitinib. In some embodiments, the kinase inhibitor is lenvatinib. In some embodiments, the kinase inhibitor is nintedanib. In some embodiments, the kinase inhibitor is regorafenib. In some embodiments, the kinase inhibitor is pazopanib. In some embodiments, the kinase inhibitor is sorafenib. In some embodiments, the kinase inhibitor is sunitinib.

Anti-cancer therapies that may be administered in combination with the bispecific anti-EGFR/c-Met antibody in the methods of the disclosure include any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL®docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™), toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA®), afatinib (BIBW 2992), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in *Medical Oncology* (Calabresi et aL, eds.), Chapter 10, McMillan Publishing, are also applicable to the methods of the present invention.

Administration

The bispecific anti-EGFR/c-Met antibody and the macrophage activating agent may be administered to the subject together in a mixture, concurrently as single agents or sequentially as single agents in any order.

In some embodiments, the bispecific anti-EGFR/c-Met antibody is administered prior to administration of the macrophage activating agent.

In some embodiments, the bispecific anti-EGFR/c-Met antibody is administered after to administration of the macrophage activating agent.

In some embodiments, the bispecific anti-EGFR/c-Met antibody is administered simultaneously to administration of the macrophage activating agent.

In some embodiments, the bispecific anti-EGFR/c-Met antibody is administered prior to administration of the third anti-cancer agent.

In some embodiments, the bispecific anti-EGFR/c-Met antibody is administered after to administration of the third anti-cancer agent.

In some embodiments, the bispecific anti-EGFR/c-Met antibody is administered simultaneously to administration of the third anti-cancer agent.

The length of time between administrations of the bispecific anti-EGFR/c-Met antibody and the macrophage activating agent or the third anti-cancer therapy may be a few minutes, such as abbot 1, 2, 5, 10, 30 or 660 minutes or several hours, such as about 2, 4, 6, 10, 12, 24 or 36 hours, or such as about 2, 4, 7, 14, 21, 28, 35, 42, 49, 56 days or more. The bispecific anti-EGFR/c-Met antibody and the macrophage activating agent or the third anti-cancer agent may be administered in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used to formulate the bispecific anti-EGFR/c-Met antibody. These solutions are sterile and generally free of particulate matter. They may be sterilized by conventional, well-known sterilization techniques (e.g., filtration). For solid oral preparations, such as powders capsules and tablets, suitable carriers and additives include starches, sugars, diluents, granulating agents, lubricants, binders, disintegrating agents and the like. Solid oral preparations may also be coated with substances such as sugars or be enteric-coated to modulate major site of absorption. For parenteral administration, the carrier may comprise sterile water and other excipients may be added to increase solubility or preservation. Injectable suspensions or solutions may also be prepared utilizing aqueous carriers along with appropriate additives. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The compositions may contain pharmaceutically acceptable auxiliary substances as required to approximate physiological conditions such as pH adjusting and buffering agents, stabilizing, thickening, lubricating and coloring agents, etc. The concentration of the bispecific anti-EGFR/c-Met antibody and the macrophage activating agent in the pharmaceutical formulation may vary, from less than about 0.5%, usually to at least about 1% to as much as 15%, 20%, 30%, 40% or 50% by weight and may be selected primarily based on required dose, fluid volumes, viscosities, etc., according to the particular mode of administration selected. Pharmaceutical compositions comprising solid forms may contain about 0.1 mg to about 2000 mg, such as about 1 mg, about 5 mg, about 10 mg, about 25 mg, about 50 mg, about 100 mg, about 150 mg, about 200 mg, about 300 mg, about 500 mg about 600 mg or about 1000 mg of active ingredient.

The mode of administration may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Generation of Bispecific Anti-EGFR/c-Met Antibodies Used in the Methods of the Disclosure An exemplary anti-EGFR/c-Met antibody that can be used in the methods of the disclosures is JNJ-372. JNJ-273 is characterized by following amino acid sequences:

```
EGFR binding arm
>SEQ ID NO: 1 (HCDR1, EGFR binding arm)
TYGMH
```

```
>SEQ ID NO: 2 (HCDR2, EGFR binding arm)
VIWDDGSYKYYGDSVKG

>SEQ ID NO: 3 (HCDR3, EGFR binding arm)
DGITMVRGVMKDYFDY

>SEQ ID NO: 4 (LCDR1, EGFR binding arm)
RASQDISSALV

>SEQ ID NO: 5 (LCDR2, EGFR binding arm)
DASSLES

>SEQ ID NO: 6 (LCDR3, EGFR binding arm)
QQFNSYPLT

>SEQ ID NO: 7 (HCDR1, c-Met binding arm)
SYGIS

>SEQ ID NO: 8 (HCDR2, c-Met binding arm)
WISAYNGYTNYAQKLQG

>SEQ ID NO: 9 (HCDR3, c-Met binding arm)
DLRGTNYFDY

>SEQ ID NO: 10 (LCDR1, c-Met binding arm)
RASQGISNWLA

>SEQ ID NO: 11 (LCDR2, c-Met binding arm)
AASSLLS

>SEQ ID NO: 12 (LCDR3, c-Met binding arm)
QQANSFPIT

>SEQ ID NO: 13 (VH, EGFR binding arm)
QVQLVESGGGVVQPGRSLRLSCAASGFTFSTYGMHWVRQAPGKGLEWVAVI
WDDGSYKYYGDSVKGRFTISRDNSKNTLYLQMNSLRAEDTAVYYCARDGIT
MVRGVMKDYFDYWGQGTLVTVSS >SEQ ID NO: 14 (VL, EGFR binding arm)
AIQLTQSPSSLSASVGDRVTITCRASQDISSALVWYQQKPGKAPKWYDASS
LESGVPSRFSGSESGTDFTLTISSLQPEDFATYYCQQFNSYPLTFGGGTKV
EIK >SEQ ID NO: 15 (VH, c-Met binding arm)
QVQLVQSGAEVKKPGASVKVSCETSGYTFTSYGISWVRQAPGHGLEWMGWI
SAYNGYTNYAQKLQGRVTMTTDTSTSTAYMELRSLRSDDTAVYYCARDLRG
TNYFDYWGQGTLVTVSS >SEQ ID NO: 16 (VL, c-Met binding arm)
DIQMTQSPSSVSASVGDRVTITCRASQGISNWLAWFQHKPGKAPKLLIYAA
SSLLSGVPSRFSGSGSGTDFTLTISSLQPEDFATYYCQQANSFPITFGQGT
RLEIK >SEQ ID NO: 17 HC1
QVQLVESGGGVVQPGRSLRLSCAASGFTFSTYGMHWVRQAPGKGLEWVAVI
WDDGSYKYYGDSVKGRFTISRDNSKNTLYLQMNSLRAEDTAVYYCARDGIT
MVRGVMKDYFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK >SEQ ID NO: 18 LC1
AIQLTQSPSSLSASVGDRVTITCRASQDISSALVWYQQKPGKAPKLLIYDA
SSLESGVPSRFSGSESGTDFTLTISSLQPEDFATYYCQQFNSYPLTFGGGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC >SEQ ID NO: 19 HC2
QVQLVQSGAEVKKPGASVKVSCETSGYTFTSYGISWVRQAPGHGLEWMGWI
SAYNGYTNYAQKLQGRVTMTTDTSTSTAYMELRSLRSDDTAVYYCARDLRG
TNYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNV
NHKPSNTKVDKRVEPKSCDKTHTCPPCPAPELLGGPSVFLFPPKPKDTLMI
SRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFL
YSRLTVDKSRWQQGNVFSCSVMHEALHNHYTQKSLSLSPGK >SEQ ID NO: 20 LC2
DIQMTQSPSSVSASVGDRVTITCRASQGISNWLAWFQHKPGKAPKLLIYAA
SSLLSGVPSRFSGSGSGTDFTLTISSLQPEDFATYYCQQANSFPITFGQGT
RLEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC
```

Other bispecific anti-EGFR/c-Met antibodies publicly available may also be used in the methods of the disclosure as long as they demonstrate similar characteristics when compared to JNJ-372 as described in U.S. Pat. No. 9,593,164. bispecific anti-EGFR/c-Met antibodies that may be used in the methods of the disclosure may also be generated by combining EGFR binding VH/VL domains and c-Met binding VH/VL domains that are publicly available and testing the resulting bispecific antibodies for their characteristics as described in U.S. Pat. No. 9,593,164.

Bispecific anti-EGFR/c-Met antibodies used in the methods of the disclosure may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on EGFR and an epitope on c-Met.

For example, the bispecific antibodies of the invention may be generated using the technology described in Int.Pat. Publ. No. WO2011/131746. Mutations F405L in one heavy chain and K409R in the other heavy chain may be used in case of IgG1 antibodies. For IgG2 antibodies, a wild-type IgG2 and a IgG2 antibody with F405L and R409K substitutions may be used. For IgG4 antibodies, a wild-type IgG4 and a IgG4 antibody with F405L and R409K substitutions may be used. To generate bispecific antibodies, first monospecific bivalent antibody and the second monospecific bivalent antibody are engineered to have the aforementioned mutation in the Fc region, the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Bispecific anti-EGFR/c-Met antibodies used in the methods of the disclosure may also be generated using designs such as the Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), and the Biclonic (Merus).

In the "knob-in-hole" strategy (see, e.g., Intl. Publ. No. WO 2006/028936) select amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

CrossMAb technology, in addition to utilizing the "knob-in-hole" strategy to promoter Fab arm exchange utilizes CH1/CL domain swaps in one half arm to ensure correct light chain pairing of the resulting bispecific antibody (see e.g. U.S. Pat. No. 8,242,247).

Other cross-over strategies may be used to generate full length bispecific antibodies of the invention by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified positions in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

SEEDbody technology may be utilized to generate bispecific antibodies of the invention. SEEDbodies have, in their constant domains, select IgG residues substituted with IgA residues to promote heterodimerization as described in U.S. Patent No. US20070287170.

Mutations are typically made at the DNA level to a molecule such as the constant domain of the antibody using standard methods.

The present invention will now be described with reference to the following specific, non-limiting examples.
Materials and Methods
PBMCs and Isolation of NK cells and Monocytes from PBMCs The Peripheral Blood Mononuclear Cells (PBMCs) and isolated immune cells (NK cells and Monocytes) were purchased from Hemacare. The PBMCs were isolated from leukopaks collected in HemaCare's FDA-registered collection centers following cGMP and cGTP collection guidelines from IRB consented healthy human donors. Peripheral blood mononuclear cells (PBMCs) were purified by a density gradient centrifugation and purchased from HemaCare in cryopreserved format and stored in liquid nitrogen until use.

For some of the donors, the leukopaks were split 3 ways to isolate PBMCs, NK cells and Monocytes from the same donor leukopak. NK cells were isolated using CD56 negative selection and Monocytes were isolated using CD14 negative selection. The isolated NK cells and Monocytes were purchased from Hemacare in cryopreserved format and stored in liquid nitrogen until use.

Differentiation of Monocytes into M1, M2a and M2c macrophages The monocytes (purchased from Hemacare) were thawed in the XVIVO 15 media supplemented with 10% FBS and plated on tissue culture treated T75 flasks. On day 0, the monocytes were plated in media with 50 ng/mL M-CSF (Cat #216-MC-025/CF purchased from R&D systems) to obtain Mo macrophages. To polarize the MO macrophages into M2a macrophages, on day 5, the media was changed with 50 ng/mL M-CSF and 20 ng/mL IL-4 (Cat #204-IL-020/CF purchased from R&D systems) and 20 ng/mL IL-13 (Cat #213-ILB-025/CF purchased from R&D systems) and incubated for 48 hrs. To polarize the MO macrophages into M2c macrophages, on day 5, the media was changed with 50 ng/mL M-CSF and 20 ng/mL IL-10 (Cat #217-IL-025/CF purchased from R&D systems) and incubated for 48 hrs. To obtain M1 macrophages, on day 6, the media was changed with 50 ng/mL M-CSF and 100 ng/mL IFN-g (Cat #285-IF-100/CF purchased from R&D systems) and incubated 24 hrs. differentiated M1, M2a and M2c macrophages were then removed from the flask using Accutase and utilized for the assays.

Depletion of NK Cells and Monocytes from PBMCs

Depletion of NK cells was performed using the EasySep Human CD56 Positive

Selection kit II (Cat #17855) from STEMCell Technologies and depletion of Monocytes was performed using the EasySep Human CD14 Positive Selection kit II (Cat #17858) from STEMCell Technologies. The PBMCs (purchased from Hemacare) were thawed in X-VIVO-15 media with 10% FBS and counted. The PBMCs (10 million cells per depletion) were resuspended in the Easy Sep buffer at the desired conc of 100 million cells/mL. The depletion for the NK cells and Monocytes were performed as per the manufacturer's protocol. Briefly, 50 µl of the respective antibody selection cocktail was added and incubated at RT for 10 mins. The magnetic particles were vortexed for 30 secs and 50 µl was added to the PBMCs+antibody cocktail. This was incubated for 3 mins at RT and made up to 2.5 mls using the EasySep buffer. The tubes were then placed into the Easy Sep Magnet (Cat #18000 from STEMCell Technologies) and incubated for 3 mins. The supernatant was then carefully transferred to a new tube. The magnetic separation step was repeated twice to obtain NK cell depleted and Monocyte depleted PBMCs. The depletion was verified using flow cytometry (as described below) and these PBMCs were then utilized for the Simple Western assay to detect EGFR and Met protein levels.

Determination of Immune Cell Composition within PBMC

The PBMCs (purchased from Hemacare) were thawed in X-VIVO-15 media with 10% FBS and counted. After counting, 300,000 to 400,000 cells/well were plated (in triplicates) and the plate was spun at 4° C. at 1500 rpms for 3 min. Supernatant was discarded and the cells were washed with 150 µl/well of DPBS. The plate was spun again to pellet as described above. The stock solution for the Near IR-Live/Dead stain (Life Technologies Cat #L10119) was made by adding 150 µL of DMSO to contents of live dead stain. The working solution was then made up by adding 50 µl of stock to 10 mls DPBS. 50 µl of the working solution was then added to each well of the plate and resuspended. The plate was incubated in dark (covered with foil) at RT for 30 min. At the end of the incubation, the plates were spun for 5 min at 4° C. and 1500 rpm. The cells were then washed with FACS/Stain buffer (BD #554657) Buffer by adding 150 µl per well. The antibodies for the multi-color flow cytometry panel was prepared into a cocktail as per the as per calculations and 25 µl well was added. The antibodies used in the panel included CD19 (FITC), CD56 (BV711), Cd11b (BUV395), CD14 (PE-cy7), CD3 (BV605), CD4 (BV785), CD8 (PerCP-cy5.5), CD25 (PE) and PD-1 (APC). The plate was incubated for 30 min at RT in dark. A compensation plate was prepared using compensation beads and the single channel antibodies from the panel above as per calculations and was incubated for 30 mins in dark at RT. All plates were spun at 1500 rpm for 5 min at 4° C. and washed twice with 150 µl FACS Buffer. The assay plate was resuspended in 150 µl of FACS buffer and compensation plate in 200 µl of FACS buffer. The plates were run on the Fortessa where the compensation was set using the single channel control values from the compensation bead plate. The assay plate was then run at flow rate of 1.5 µl sec with the compensation applied. The data was then exported and analyzed in FLOWJo, where appropriate gating was done to obtain the percentage of the each of the individual immune cell populations within the PBMCs.

Proliferation and Apoptosis Assay

HCl-H1975 cells (also herein referred to as H1975 cells) were obtained from ATCC and cultured in RPMI (Invitrogen, Cat #72400-047) supplemented with 10% Hi FBS, 1×NEAA, 1× Sodium Pyruvate. For the proliferation and apoptosis assay using the Incucyte, H1975 cells were infected with Incucyte NucLight Red lentiviral reagent (Cat #4476 from Essen Biosciences) and selected with 1 µg/ml puromycin to generate H1975 NucRed cells. These cells were plated in RPMI-phenol red-free media, supplemented with, 10% HI FBS, 1×NEAA, 1× sodium pyruvate for the experiment.

H1975-NucRed cells were dissociated using Invitrogen Cell Dissociation Buffer (since trypsin disintegrates the cell surface receptors/molecules) and counted. The cells were centrifuged at 1200 rpm for 5 min and the supernatant were removed. The pellets were then resuspended in appropriate volume of phenol red free media. The NucRed cells (target cells) were plated at 12,500 cells/well in 100 µl of Phenol-red media into tissue culture treated, black flat bottom plates and incubated at 37° C. and 5% $CO_2$ overnight. On the next day, PBMCs (purchased from HemaCare) were thawed in X-VIVO-10 media with 10% FBS and counted. The PBMCs were diluted at concentration of 125,000 cells per well in 50 µl, to obtain an effector:target (E:T) ratio of 10:1. Incucyte Annexin V Green reagent (Cat #4642 purchased from Essen Biosciences) was resuspended in 100 µl media and used to stain 100 wells or 1 96-well plate. The diluted Annexin reagent was added to the PBMCs or media. 50 ul of the PBMCs/media (with Annexin) was added to the appropriate wells of the assay plate. The therapeutic antibodies were then serially diluted at 1:5 and prepared at 4× concentration as per calculations and 50 µl of desired antibody was added to the appropriate wells of the assay plate. The assay plates were then placed in the appropriate slots in the Incucyte S3 and equilibrated in the Incucyte for 20 min prior to scanning Plates were scanned every 4 hours with 4 images/well/scan up to 120 hrs to determine target cell proliferation and apoptosis over time. Target cell (NucRed) fluorescence and Annexin (Green) fluorescence was quantified using the Process Definition and the Total NucRed H1975 Area (µm2/well) was calculated, which shows target cell proliferation. Total Green NucRed H1975 Area (um2/well) was also calculated, which shows target cell apoptosis. From this analysis, Graphpad Prism was used to calculate Area under the curve (AUC) and non-linear does-response curves were generated.

Simple Western for Detection of EGFR, c-Met, pEGFR and pMet Protein Levels

H1975 cells and SNU-5 cells were obtained from ATCC and cultured in RPMI (Invitrogen, Cat #72400-047) supplemented with 10% Hi FBS, 1×NEAA, 1× Sodium Pyruvate. H1975 cells were dissociated using Cell Dissociation Buffer and each cell suspension was placed into a 50 mL conical tube and counted. In assays with SNU-5 (suspension cell line), the cell suspension was transferred to a 50 mL conical tube and counted. The cells were pelleted at 1300 rpms for 5 min at 4° C. and resuspended in appropriate volume of RPMI media. The target cells were plated at a concentration of 100,000 cells per well in 6 well plates and incubated overnight. On the next day, PBMCs (purchased from HemeCare) were thawed in X-VIVO-15 media with 10% FBS and counted. The PBMCs were diluted and plated at concentration of 1,000,000 cells per well, to obtain an E:T ratio of 10:1. When individual immune cells such as NK cells, Monocytes or Macrophages were used, they were diluted and plated at concentration of 500,000 cells per well, to obtain an E:T ratio of 5:1. The therapeutic antibodies were then prepared at 2× concentration as per calculations and 1.5 mL of desired antibody was added to the appropriate wells of the assay plate. The plates were incubated for 48 hrs (for most assays) or for varying time points.

At the end of the incubation period, 100 μl of freshly prepared lysis buffer was added to each well and incubated on ice for 5 mins. The lysis buffer was prepared using 10 mL of RIPA buffer (ThermoFisher; Cat #89901) with 1 tab of Phosphatase Inhibitor PhosSTOP (Sigma; Cat #4906837001) and 1 tab of Protease Inhibitor cOmplete™, Mini, EDTA-free Protease Inhibitor Cocktail (Sigma; Cat #04693159001). Using a plate scraper, the lysates were transferred to a 2 ml Eppendorf tube and incubated on ice for 30 mins with occasional vortexing. The lysates were centrifuged at 13,200 rpm for 25 mins at 4° C. and the supernatants were transferred to new tubes. The protein concentration of the lysates was determined using the Pierce BCA Protein assay kit (Cat #23227 obtained from ThermoFisher) as per the manufacturer's protocol. Pierce Bovine Serum Albumin Standard Pre-Diluted standards (Cat #23208 obtained from ThermoFisher) were used to obtain the standard curve for the assay. Briefly, 25 μl of the pre-diluted standards was added in triplicates and 25 μl of the samples (diluted 1:5) were added in duplicates onto a 96 well flat bottom plate. 200 ul of the prepared BCA working reagent was added per well. The plate was gently mixed for 1 min on the plate shaker and incubated for 30 mins at 37° C. covered with foil. After the incubation, the plate was allowed to cool at RT for 5 mins before measuring the protein quantification using the SpectraMAX spectrophotometer at 562 nm To perform the capillary based electrophoresis using PeggySue, the 12-230 kDa Peggy Sue Separation module (Cat #SM-S001 purchased from Protein Simple) was utilized alone with the anti-rabbit detection module (Cat #DM-001) and anti-mouse secondary antibody (Cat #042-205) both purchased from Protein Simple. The samples, antibodies and reagents were prepared, and the capillary based electrophoresis was performed as per the manufacturer's protocol. Briefly, the components of 2 standard packs were used to prepare the biotinylated ladder and 5× master mix. The protein lysates were diluted to a concentration of 0.25 mg/ml using 0.1 × sample buffer as per the calculations using values from the BCA protein assay. 4 parts of prepared lysate was combined with 1 part 5× Fluorescent Master Mix to obtained the final concentration of 0.2 mg/mL. The samples and the biotinylated adder were denatured using a PCR thermocycler at 95° C. for 5 min. The primary antibodies utilized for the assay were diluted as follows using the Antibody diluent: EGFR (Cat #2646 from Cell Signaling Technologies) at 1:50; pEGFR (Cat #AF1095 from R&D Systems) at 1:50; c-Met (Cat #3148 from Cell Signaling Technologies) at 1:50; pMet (Cat #3077 from Cell Signaling Technologies) at 1:50 and loading control Actin (Cat #4970 from Cell Signaling Technologies) at 1:200 or (Cat #4947 from Cell Signaling Technologies) at 1:100. The ladder, samples, primary and secondary antibodies, separation and stacking matrices were added to the 384 well Peggy Sue plate as per the plate layout. The plate was spun at 2500 rpm for 5 mins at RT before loading it onto the machine. The data was analyzed using the Compass for SW software. Peaks were determined based on the molecular weight of the proteins of interest and the Area under the Curve (AUC) was calculate for each protein in each of the samples. The densitometry values for the protein of interest was then normalized to the loading control Actin for each of the samples and then normalized to the no treatment control to obtain relative changes with the treatment.

Confocal Imaging Trogocytosis Assay

Differentiated macrophages were harvested and plated onto CellCarrier96 ultra plates at 1,00,000 cells/well (Perkin-Elmer; Cat #6055302) overnight. Assays were performed using both adhered and non-adhered target cells. For assays with adhered target cells, the H1975 NucLight Red cells were plated at 20,000/well, adhered for 4 hours, then treated with labeled Ab cocktail for 1 hour at 4° C. For assays with non-adhered target cells, target cells alone were stained with AF647-labeled JNJ-372 or control Abs. All live imaging studies were performed at an E:T ratio of 5:1. Labeling Antibody cocktail comprised of anti-CD11b (BD Pharmingen; Cat #557701), anti-CD14 (BD Pharmingen; Cat #562689), and 1:8000 Hoechst33342 (Biotium; Cat #40046). Images were obtained at 11-minute intervals on a Perkin-Elmer Phenix Opera using 60× water-immersion objective and analyzed using Columbus.

ADCC Assay

PBMCs were thawed one day prior to assay in X-VIVO 10 media (Lonza, Cat #04-380Q) supplemented with 10% heat inactivated FBS (GIBCO, Cat #16140) and rested overnight under standard incubation conditions (37° C., 5% $CO_2$, 95% humidity). On the day of assay, NCI-H1975 target cells were loaded with DELFIA BATDA reagent (PerkinElmer Inc., Cat #C136-100) for 30 minutes, washed 3 times, and resuspended in RPMI media. PBMCs and BATDA-loaded target cells were added to 96-well U-bottom plates at an effector to target cell ratio of 25:1 along with increasing concentrations of test antibodies. RPMI media or RPMI media containing 2% Triton X-100 (EMD Millipore, Cat #648463) was added to control wells for measurement of spontaneous and maximal TDA release respectively. Plates were incubated for 2 hours, after which 20 uL of supernatant was removed and combined with 200 μL of DELPHIA Europium solution (Perkin Elmer, Cat #C135-100). After incubation at RT for 15 mins, Relative Fluorescence Units (RFU) were measured using an EnVision 2104 Multilabel Plate Reader (PerkinElmer, Cat #2104-0010). Percent lysis was calculated as (Experimental release—Spontaneous release)/(Maximal release—Spontaneous release)×100.

Differentiation of Monocytes into M1, M2a and M2c Macrophages

Monocytes (Hemacare) were thawed in the XVIVO-15 media and differentiated with 50 ng/mL M-CSF (R&D systems; Cat #216-MC-025/CF) for 6 days to obtain MO macrophages. To obtain M1 macrophages, on day 5, MO macrophages were polarized with 50 ng/mL M-CSF and 100 ng/mL IFN-γ (R&D systems; Cat #285-IF-100/CF) for 48 hrs. To obtain M2 macrophages, on day 5, MO macrophages were polarized with 20 ng/mL IL-4 (R&D systems; Cat #204-IL-020/CF) and IL-13 (R&D systems; Cat #213-ILB-025/CF) for M2a or 20 ng/mL IL-10 (R&D systems; Cat #217-IL-025/CF) for M2c macrophages for 48 hrs.

In vivo Studies

The H1975 cell line was subcutaneously implanted into 6-8 week old female BALB/c nude mice (CAnN.Cg-Foxn1$^{nu}$/Crl, Charles River Laboratories, Wilmington, Ma.). When tumors were an average of 72±8.7 mm$^3$, intraperitoneal anti-mCSF-1R antibody (400 μg/mouse) was administered thrice weekly for the duration of the study, beginning five days prior to compound dosing initiation to facilitate macrophage depletion. At day 5 (average tumor volume=102±36.6 mm$^3$), they were treated twice weekly by intraperitoneal dosing with 10 mg/kg isotype control Ab, JNJ-372, or EGFR/cMet IgG2G Ab. Tumors were sampled to monitor macrophage infiltration following two doses of compound. For SNUS tumor model study, SNUS cells were subcutaneously implanted into 7-8 week old female CB17/SCID mice (HFK Bio-Technology Co. Ltd., Beijing, China). When tumors were at an average of 155±21.4 mm$^3$, mice were treated twice weekly with intraperitoneal Phosphate Buffered Saline (PBS), JNJ-372 (5 mg/kg), or EGFR-cMet IgG2G antibody (5 mg/kg), for three weeks. For both studies, tumor measurements and body weights were recorded twice weekly. Tumor growth inhibition (TGI) was calculated on the final day where >80% control mice remained on study, using the calculation [1-(T/C)]*100. All in vivo experiments were done in accordance with the Johnson and Johnson Institutional Animal Care and Use Committee and the Guide for Care and Use of Laboratory Animals Flow Cytometry-Based Determination of Tumor Associated Macrophages Tumors were excised from mice, weighed, sectioned into 2-4 mm pieces, placed into C-tubes (Miltenyi, Cat #130-093-237) containing 2.5 mL of RPMI and maintained on ice. According to manufacturer's instruction, the lyophilized enzymes contained in a Human Tumor Dissociation Kit (Miltenyi, Cat #130-095-929) were reconstituted and a 2x enzyme cocktail was prepared and tumors were dissociated on a GentleMACS Octo Dissociator (Miltenyi, Cat #130-095-937) using manufacture protocol "h_tumor_01" followed by two rounds of incubation at 37° C. for 30 minutes. Dissociated cells were washed twice in FACS Stain Buffer (BD Pharmingen, Cat #554657) and passed through a Falcon 40 μm cell strainer (Corning, Cat #352340). Cells were incubated in GolgiPlug (BD, Cat #555029) diluted 1:1000 in FACS buffer and incubated for 3 hours at 37° C., washed twice, and resuspended in 100 μL of antibody staining cocktail. The antibody cocktail consisted of anti-CD45 (Cat #103138), anti-F4/80 (Cat #123137), anti-Ly6G (Cat #127639), anti-MHCII (Cat #107612), anti-EpCAM (Cat #324214), anti-PD1 (Cat #135231), anti-PD-L1 (Cat #393606), anti-CD206 (Cat #141729) from BioLegend, anti-CD11b (Cat #563553) and anti-Ly6C (Cat #561237) from Becton-Dickinson, anti-iNOS (Cat #25-5920-82) and Fixable Live/Dead stain (Cat #L10119) from Invitrogen. Cells were incubated with external cell surface marker antibodies for 30 minutes at 4° C. protected from light, washed twice with PBS, and resuspended in PBS containing Fixable Live/Dead stain, incubated for 30 minutes at 4° C., and washed twice with FACS buffer (BD Pharmingen; Cat #554657). Cells were fixed/permeabilized according to manufacturer's instructions (Invitrogen, Cat #88-8824-00), incubated with internal target antibodies for 30 minutes at 4° C., washed 2× with FACS buffer, and resuspended in 200 jut for analysis on BD LSR Fortessa. Compensation was performed using UltraComp eBeads (for antibodies; Invitrogen, Cat #01-2222-42) and ArC Amine Reactive beads (for Fixable Live/Dead, Invitrogen, Cat #A10346). FMO controls were performed for all markers. To determine tumor associated macrophage depletion, macrophages were defined as CD45$^+$ CD11b$^+$ Ly6C$^-$ Ly6G$^-$ F4/80$^+$.

MSD Multi-Plex Assay and Statistical Analysis

For PBMC, NK cells and monocytes experiments, NCI-H1975 cells were plated into 96-well plates and allowed to incubate overnight at 3TC and 5% $CO_2$ The next day, PBMC, monocytes or NK cells were added at a ratio of 10:1, 5:1 and 5:1 respectively. For Macrophage experiments, the monocytes were differentiated as previously described, dissociated using StemPro Acutase (Gibco, Cat #A11105-01) and plated into 96-well plates and allowed to incubate overnight at 37° C. and 5% $CO_2$. The next day, NCI-H1975 cells were added at a E:T ratio of 5:1. The cells were treated with Isotype control, JNJ-61186372 or IgG2Sigma at varying concentrations and incubated at 37° C. and 5% $CO_2$ for 4 hrs, 24 hrs, 48 hrs and/or 72 hrs. At the designated time, the plates were spun at 1200 rpms for 10 min at room temperature. The supernatant was removed and evaluated using MesoScale Discovery (MSD) U-plex and V-plex formats for the respective cytokine assays as per manufacturer's instructions. Briefly, for the U-plex plates, on the day before the assay, the plates were coated with the antibody and linkers according to manufacturer's protocol and incubated on an orbital shaker at 4° C. overnight. On the day of the experiment, the U-plex or V-plex plates were washed 3× with MSD wash buffer and supernatants, standards and calibrators were added to the plates and run according to manufacturer's protocol. Plates were read on an MSD Sector instrument and analyzed using GTS Spotfire to obtain the Calculated levels (in pg/ml) for each cytokine using the standard curve.

From the calculated concentrations, area under the curve (AUC) was calculated by the trapezoidal method for each treatment, cell type, and incubation time in order to compare magnitude of response. Response data was excluded if the observed value was below the lower limit of detection, and AUC was only calculated where there were at least 6 valid observations of the 8 dose concentrations. A heatmap was then generated using to illustrate data availability (no data, not enough data, or calculable AUC data) across all cytokines and conditions. Heatmaps of log-transformed AUC were then produced using by incubation time and limited to cytokines with at least one measurable AUC in the H1975+PBMC cell type. All heatmaps were produced using package heatmap.2 in the statistical software R version 3.5.0 (R Core Team 2018; R: A language and environment for statistical computing; http://www.R-project.org/). Finally, relative change of JNJ-372 and IgG2σ treatment compared to isotype was calculated in each condition and bar graphs or dose curves were generated using Graphpad Prism.

EXAMPLE 1

JNJ-372-Mediated Anti-Proliferative and Apoptotic Effects on Tumor Cells is Driven by Fc Interactions with Immune Cells To evaluate the effect of Fc interaction on the three anti-tumor mechanisms of JNJ-372, JNJ-372 was engineered into an Fc effector silent molecule by replacing JNJ-372 wild-type IgG1 with an effector silent IgG2sigma (IgG2sigma containing V234A G237A P238S H268A V309L A330S P331S mutations when compared to the wild-type IgG2) (JNJ-372.IgG2sigma) using standard cloning methods. The engineered effector silent antibody is referred to as JNJ-372.IgG2sigma (or IgG2s in some Figures). JNJ-372 is produced in a cell lines incorporating low levels (<9%) of fucose to enhance binding to the FcγRIII/CD16 and ADCC. Therefore, as another control, JNJ-372 was also expressed in a CHO cell that incorporates normal fucose level; this molecule is referred to as JNJ-372. NF (NF: normal fucose). Tumor cell killing was evaluated using NCI-H1975 cells (ATCC Cat. No.CRL-5908); the cell line expresses mutant L858R/T790M EGFR and wild type c-Met.

Figure 2:
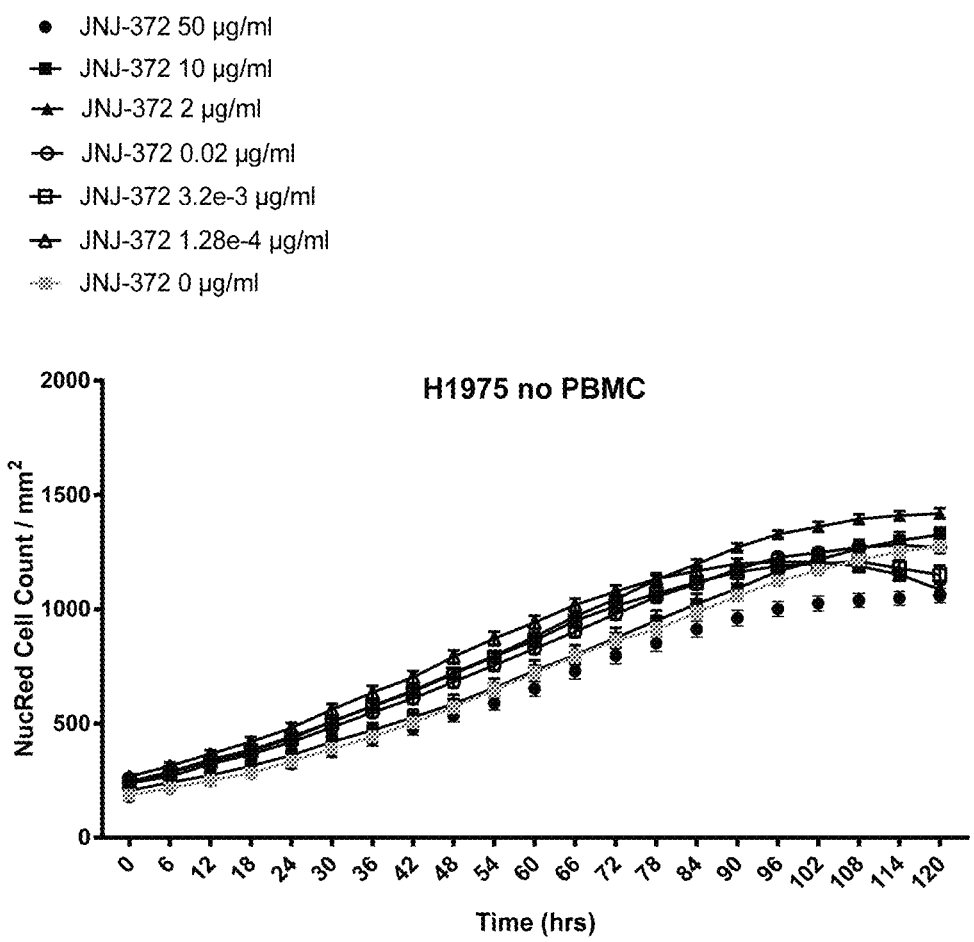
FIG. 2 shows JNJ-372 mediated effect on proliferation of NucLight Red labeled NCI-H1975 cells in the absence of PBMCs at indicated JNJ-372 concentrations in cultures up to 120 hours as measured using NucLight Red cell count/mm$^2$.

NCI-H1975 NucLight Red expressing cells were treated with Isotype control, JNJ-372, JNJ-372.IgG2s or JNJ-372.NF and cultured in the presence or absence of PBMCs at effector:target ratio of 10:1 and proliferation of NCI-H1975 cells was assessed over 5 days after initiation of co-cultures. The presence of PBMCs enhanced the ability of JNJ-372 to inhibit tumor cell proliferation over time in a dose-dependent manner (FIG. 1) whereas JNJ-372 did not inhibit proliferation in the absence of PBMCs at tested concentrations (FIG. 2).

Figure 3:
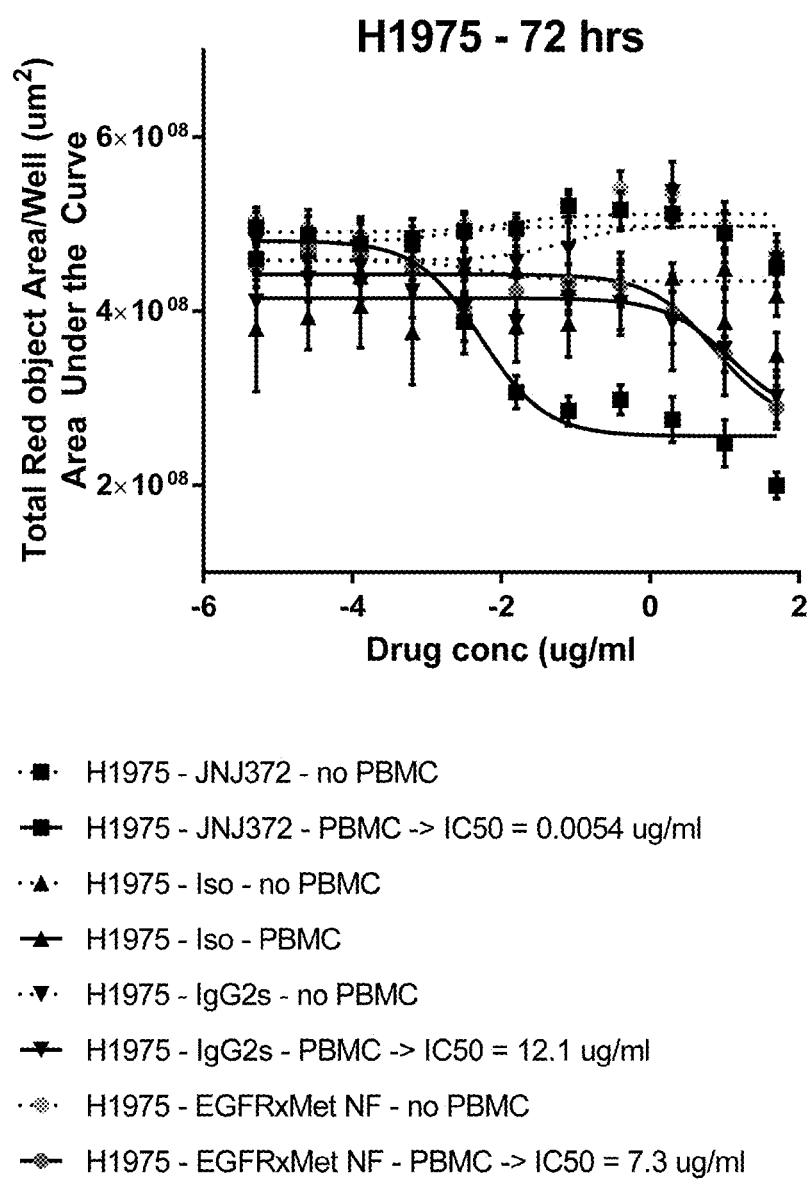
FIG. 3 shows JNJ-372, JNJ-372.IgG2sigma, JNJ-372.NF or isotype control mediated inhibition of proliferation of NucLight Red labeled NCI-H1975 cells in the presence of PBMCs. Proliferation was not inhibited in the absence of PBMCs or by the isotype control or by an Fc effector silent JNJ-372.IgG2sigma. JNJ-372.NF cultured in the presence of PBMCs partially inhibited proliferation. Iso: isotype control; IgG2s: JNJ-372. IgG2sigma; EGFRxMet NF: JNJ-372.NF.
Figure 4:
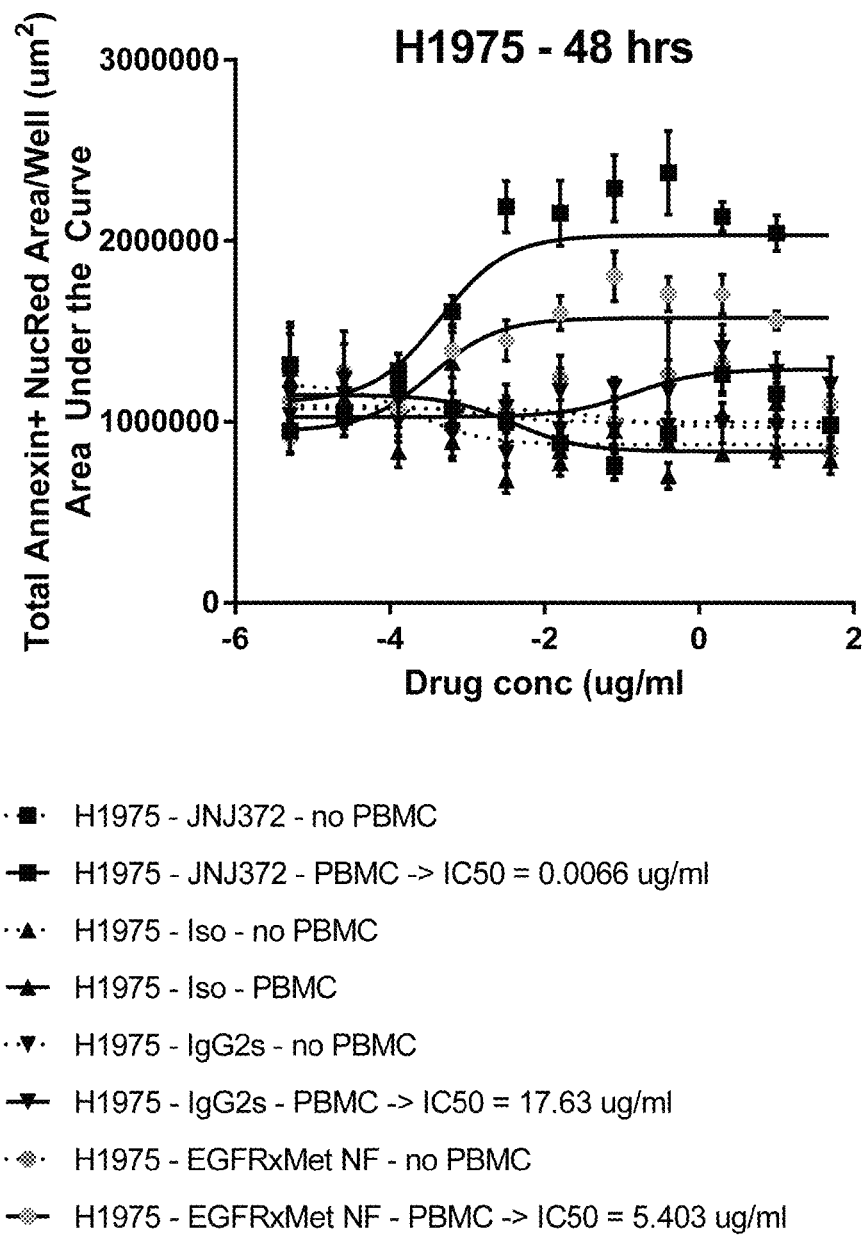
FIG. 4 shows JNJ-372, JNJ-372.IgG2sigma, JNJ-372.NF or isotype control mediated apoptosis of NucLight Red labeledNCI-H1975 cells in the presence of PBMCs after 48 hours of culture. Apoptosis was not induced in the absence of PBMCs or by the isotype control or an Fc effector silent JNJ372.IgG2sigma. JNJ-372.NF cultured in the presence of PBMCs partially mediated apoptosis. Iso: Isotype control; IgG2s: JNJ-372. IgG2sigma; EGFRxMet NF: JNJ-372.NF.

To confirm that Fc engagement on PBMCs were responsible for the effect, H1975 NucLight Red expressing cells were treated with JNJ-372, JNJ-372.IgG2sigma and JNJ-372. NF and cultured in the presence or absence of PBMCs at E:T ratio of 10:1 for 4, 24, 48, 72 or 96 hours, after which proliferation and apoptosis of H1975 cells were assessed. The presence of PBMCs enhanced the dose-dependent anti-proliferative effects and dose-dependent apoptosis (measured by annexin positivity) induced by JNJ-372 at 24, 48, 72 and 96 hours. No or minimal effects were seen with isotype or JNJ-372.IgG2sigma. FIG. 3 shows the dose response of Isotype control, JNJ-372, JNJ-372.IgG2sigma or JNJ-372. NF mediated inhibition of H1975 cell proliferation in the presence or absence of PBMCs after 72 hours of culture. FIG. 4 shows the dose response of Isotype control, JNJ-372, JNJ-372.IgG2sigma or JNJ-372.NF mediated apoptosis the presence or absence of PBMCs after 48 hours of culture. JNJ-372.NF had a partial effect on proliferation (FIG. 3) and apoptosis (FIG. 4) when compared to JNJ-372, suggesting that FcγRIII plays a role but does not entirely account for Fc interaction mediated effects.

In the assays, PBMCs from seven different donors at effector:target ratio of 10:1 were used. The $IC_{50}$ values and % Max killing in the NCI-H1975 proliferation assay is shown in Table 1 for six donors. PBMCs from one donor had no effect. Variability in the $IC_{50}$ and % Max killing was observed across the PBMCs obtained from different donors.

TABLE 1

| Donor Number | 72 hours | | 48 hours | |
| --- | --- | --- | --- | --- |
| | $IC_{50}$ (ng/ml) | % Max Killing | $IC_{50}$ (ng/ml) | % Max Killing |
| 1 | 1.2 | 43.7 | 2.99 | 31.8 |
| 2 | 0.776 | 53.7 | 1.57 | 36.6 |
| 3 | 4.87 | 72.3 | 6.93 | 52.6 |
| 4 | 4.44 | 57.8 | 4.36 | 40.5 |
| 5 | 0.59 | 70.5 | 0.79 | 43.9 |
| 7 | 0.567 | 34.7 | 0.76 | 28.3 |

EXAMPLE 2

JNJ-372-Mediated Downregulation of EGFR and C-Met Protein and Their Downstream Signaling in EGFR Mutant Tumor Cell Lines is Mediated by Fc Interactions with Immune Cells Presence of immune cells (PBMCs) potentiated JNJ-372-mediated downregulation of EGFR and c-Met protein and inhibition of their phosphorylation.

Figure 5:
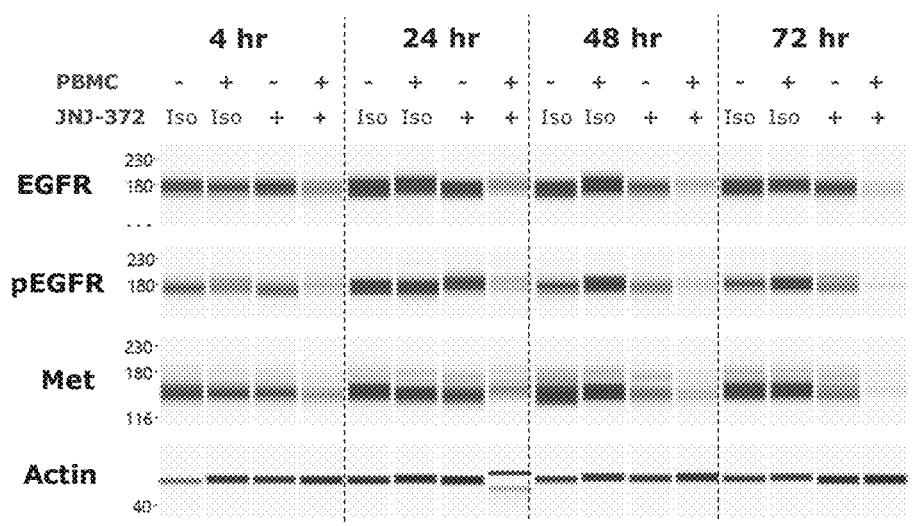
FIG. 5 shows the image from capillary based electrophoresis (Simple Western using PeggySue) showing EGFR, c-Met and pEGFR proteins in NCI-H1975 samples treated with isotype control or JNJ-372 and cultured in the presence or absence of PBMCs for 4, 24, 48 or 72 hours as indicated in the Figure. The presence of PBMCs potentiated JNJ-372 mediated downregulation of EGFR and c-Met proteins and inhibition of pEGFR.
Figure 6:
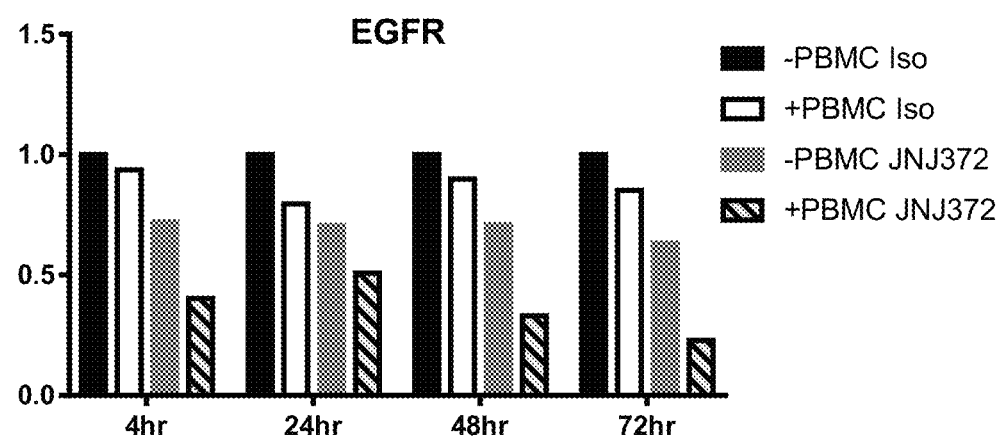
FIG. 6 shows the relative amount of EGFR (normalized to loading control Actin) in NCI-H1975 samples treated with isotype control or JNJ-372 and cultured in the presence or absence of PBMCs for 4, 24, 48 or 72 hours as indicated in the Figure. The presence of PBMCs potentiated JNJ-372 mediated downregulation of EGFR.
Figure 7:
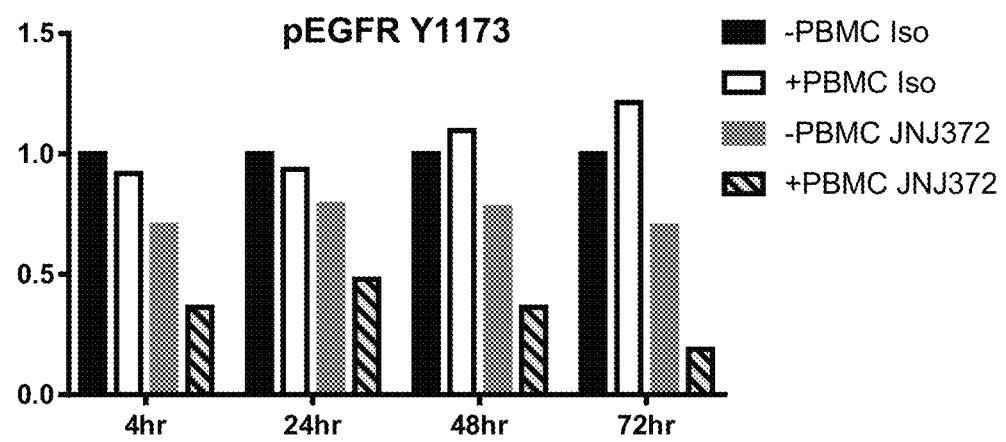
FIG. 7 shows the relative amount of pEGFR (pY1173) (normalized to loading control Actin) in NCI-H1975 samples treated with isotype control or JNJ-372 and cultured in the presence or absence of PBMCs for 4, 24, 48 or 72 hours as indicated in the Figure. The presence of PBMCs potentiated JNJ-372 mediated downregulation of pEGFR.
Figure 8:
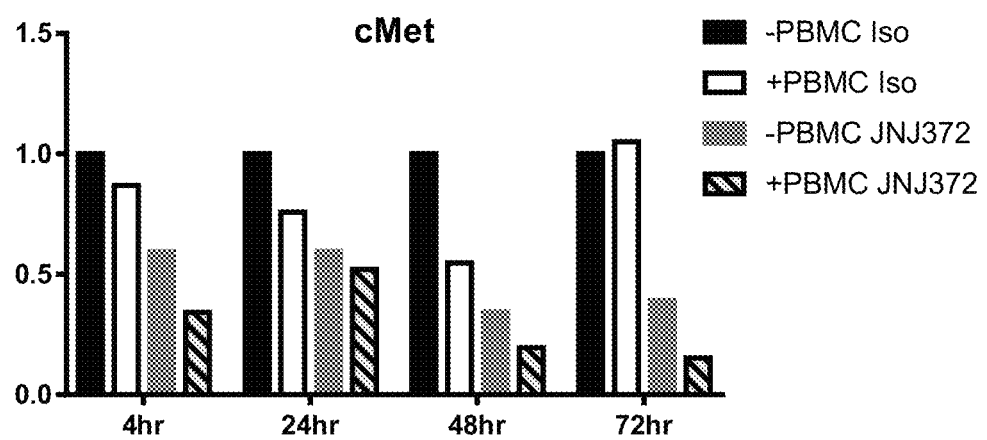
FIG. 8 shows the relative amount of c-Met (normalized to loading control Actin) in NCI-H1975 samples treated with isotype control or JNJ-372 and cultured in the presence or absence of PBMCs for 4, 24, 48 or 72 hours as indicated in the Figure. The presence of PBMCs potentiated JNJ-372 mediated downregulation of c-Met.

NCI-H1975 cells were treated with 10 μg/mL isotype or JNJ-372 and cultured in the presence or absence of PBMCs from one donor at E:T ratio of 10:1 for 4, 24, 48 or 72 hours and the amount of EGFR, c-Met and pEGFR (pY1173) was measured. Actin was used as a loading control. The presence of PBMCs potentiated JNJ-372 mediated downregulation of EGFR, c-Met and pEGFR (pY1173) at all timepoints tested. FIG. 5 shows the image from capillary based electrophoresis (Simple Western using Peggy Sue) showing EGFR and c-Met proteins and pEGFR in samples treated with isotype control or JNJ-372 and cultured in the presence or absence of PBMCs as indicated in the Figure. FIG. 6 shows the relative amount of EGFR in each sample. FIG. 7 shows the relative amount of pEGFR pY1173 in each sample. FIG. 8 shows the relative amount of c-Met in each sample. Samples were normalized to the amount of the loading control Actin present in each sample and then to the control (no treatment) sample.

Figure 9:
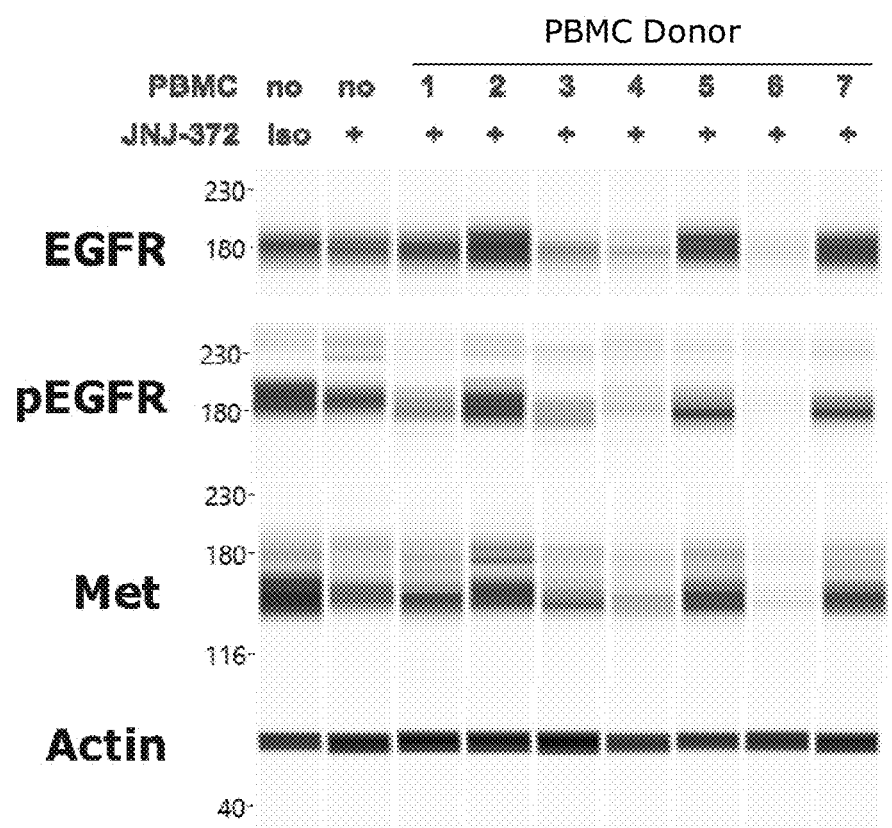
FIG. 9 shows the image from capillary based electrophoresis (Simple Western using PeggySue) showing EGFR, c-Met and pEGFR proteins in NCI-H1975 samples treated with isotype control or JNJ-372 and cultured for 48 hours in the presence or absence of PBMCs from seven different donors as indicated in the Figure.
Figure 10:
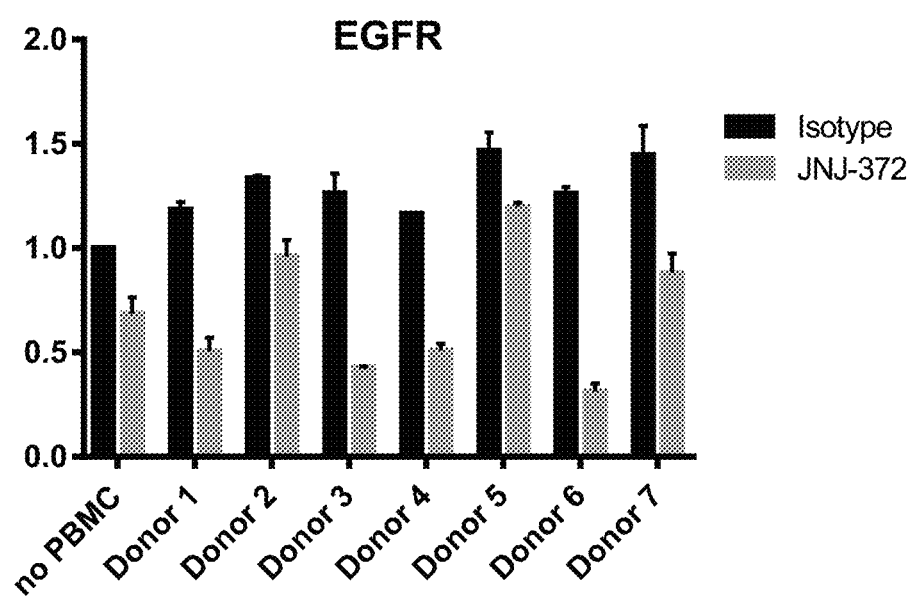
FIG. 10 shows the relative amount of EGFR (normalized to loading control Actin) in NCI-H1975 samples treated with isotype control or JNJ-372 and cultured for 48 hours in the presence or absence of PBMCs from seven different donors as indicated in the Figure.
Figure 11:
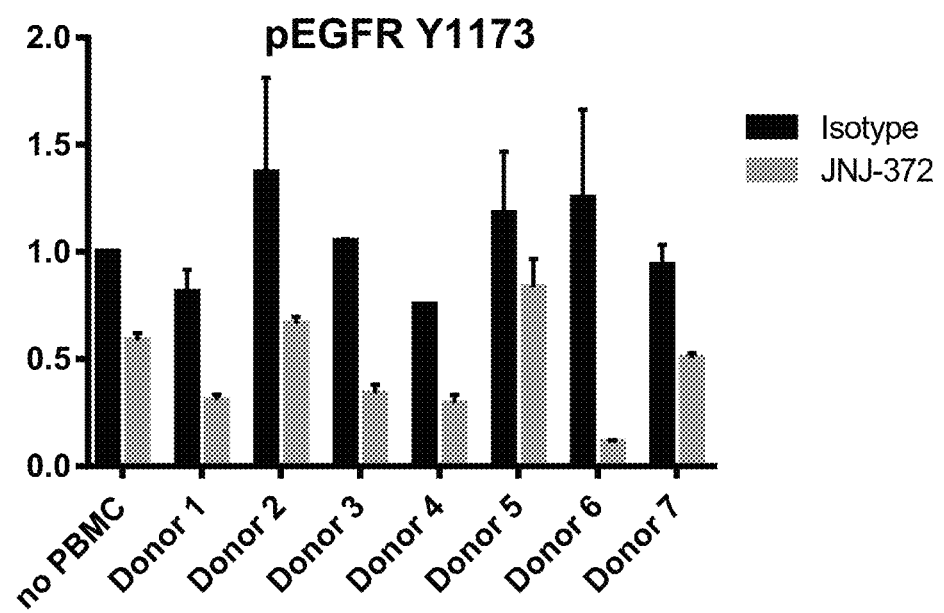
FIG. 11 shows the relative amount of pEGFR (pY1173) (normalized to loading control Actin) in NCI-H1975 samples treated with isotype control or JNJ-372 and cultured for 48 hours in the presence or absence of PBMCs from seven different donors as indicated in the Figure.
Figure 12:
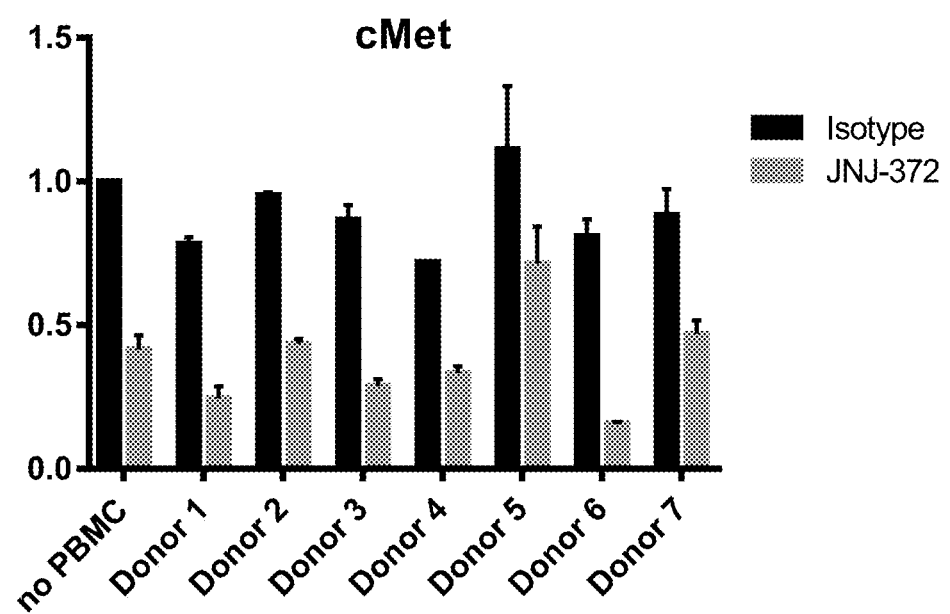
FIG. 12 shows the relative amount of c-Met (normalized to loading control Actin) in NCI-H1975 samples treated with isotype control or JNJ-372 and cultured for 48 hours in the presence or absence of PBMCs from seven different donors as indicated in the Figure.

PBMCs from seven donors were tested for their ability to potentiate JNJ-372 mediated inhibition of EGFR and c-Met protein levels and pEGFR. Variation was observed among the donor PBMC. PBMCs from donors 1,3,4 and 6 were most potent in potentiating JNJ-372 mediated effects. FIG. 9 shows the image from capillary based electrophoresis (Simple Western using Peggy Sue) showing EGFR and c-Met proteins and pEGFR in samples treated with isotype control or JNJ-372 cultured in the presence or absence of PBMCs from seven different donors as indicated in the Figure. FIG. 10 shows the relative amount of EGFR in each sample. FIG. 11 shows the relative amount of pEGFR pY1173 in each sample. FIG. 12 shows the relative amount of c-Met in each sample. Samples were normalized to the amount of the loading control Actin present in each sample and then to the control (no treatment) sample.

EXAMPLE 3

Figure 13:
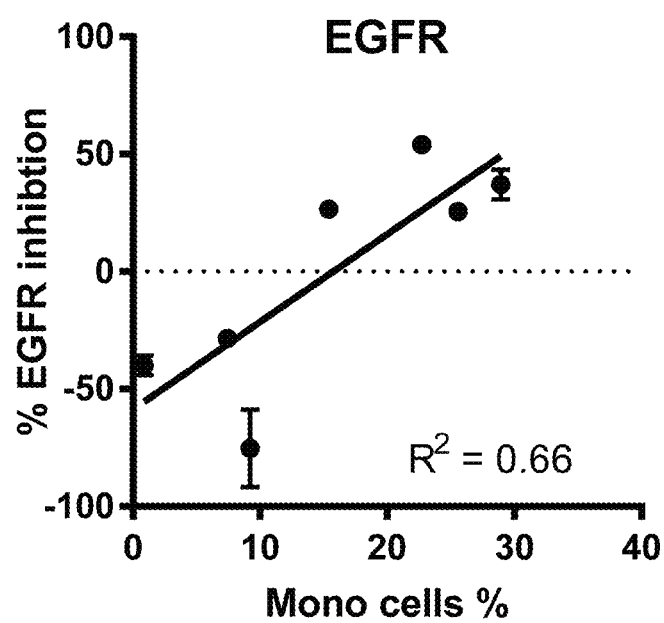
FIG. 13 shows the correlation between the percent (%) monocytes in the PBMC sample of each donor and the percent (%) change in EGFR inhibition with JNJ-372 in the presence of PBMCs (relative fold change over no PBMCs), as measured by the amount of EGFR protein (normalized to loading control Actin) in NCI-H1975 cells.
Figure 14:
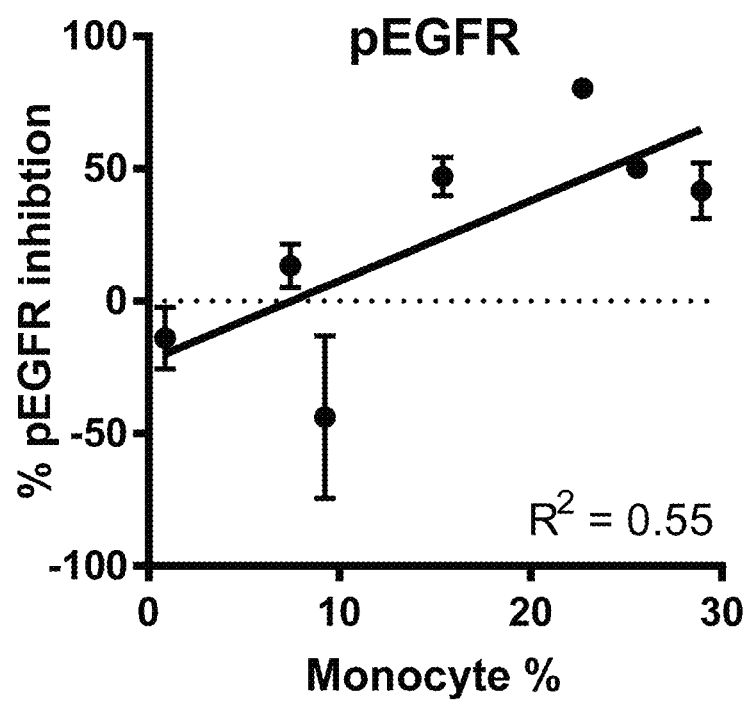
FIG. 14 shows the correlation between the percent (%) monocytes in the PBMC sample of each donor and the percent (%) change in pEGFR Y1173 inhibition with JNJ-372 in the presence of PBMCs (relative fold change over no PBMCs), as measured by the amount of pEGFR protein (normalized to loading control Actin) in NCI-H1975 cells.
Figure 15:
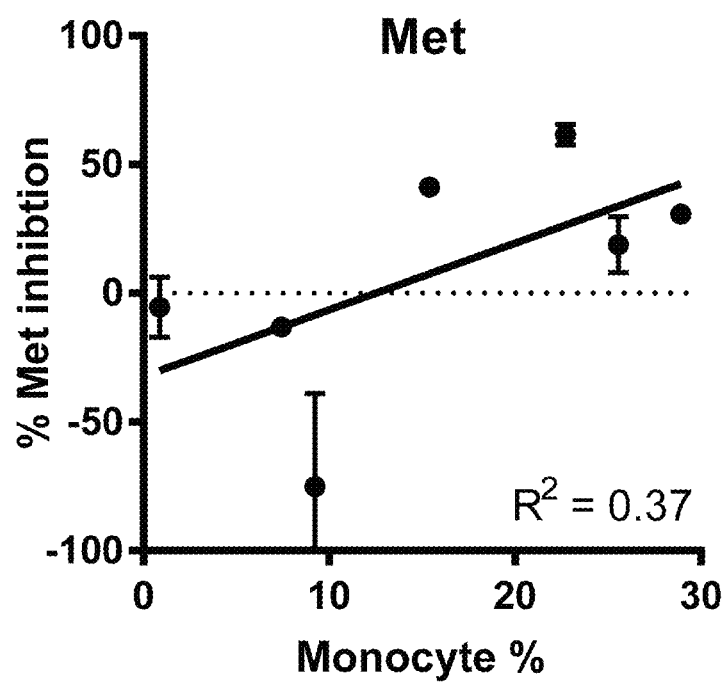
FIG. 15 shows the correlation between the percent (%) monocytes in the PBMC sample of each donor and the percent (%) change in c-Met inhibition with JNJ-372 in the presence of PBMCs (relative fold change over no PBMCs), as measured by the amount of c-Met protein (normalized to loading control Actin) in NCI-H1975 cells.

Presence Of Monocytes or Macrophages is Sufficient and Necessary for Fc Mediated Potentiation of JNJ-372 Inhibitory Effect on EGFR and C-Met Signaling The composition of the immune cells within PBMCs from the seven different donors used in Example 2 was evaluated using multi-color Flow cytometry to understand the variation in the ability of the various PBMC samples to potentiate the ability of JNJ-372 to downregulate of EGFR and c-Met signaling. Variability was detected among the donors in the percentage of the individual immune cells (data not shown). A correlation was performed with the percentage of the individual immune cells in each of the 7 donors and the ability of each donor PBMCs to mediate EGFR/pEGFR/Met downregulation. No correlation was observed between NK cell, B cells or T cells and the ability of the PBMCs to potentiate downmodulation of EGFR, pEGFR or c-Met (data not shown). However, a positive correlation was identified between the % monocytes in the PBMCs and the ability of the PBMCs to potentiate the downmodulation of EGFR protein levels (FIG. 13), between the % monocytes in the PBMCs and the ability of the PBMCs to potentiate the downmodulation of pEGFR (FIG. 14) and between the % monocytes in the PBMCs and the ability of the PBMCs to potentiate the downmodulation of c-Met protein levels (FIG. 15). This suggested that higher monocyte percentage in the PBMCs is required for JNJ-372 mediated signal downregulation.

PBMCs from one donor were depleted of NK cells or monocytes and the effect of the NK- or monocyte-depleted PBMC on JNJ-372-mediated downmodulation of EGFR and c-Met pathways was assessed. H1975 cells were treated with 10 μg/mL isotype control or JNJ-372 and cultured in the presence or absence of NK cell depleted PBMCs or monocyte depleted PBMCs obtained from one donor at E:T ratio of 10:1 for 48 hours. Consistent with previous results, the presence of PBMCs enhanced JNJ-372 mediated downregulation of EGFR, pEGFR and c-Met in the H1975 cell line.

Figure 16:
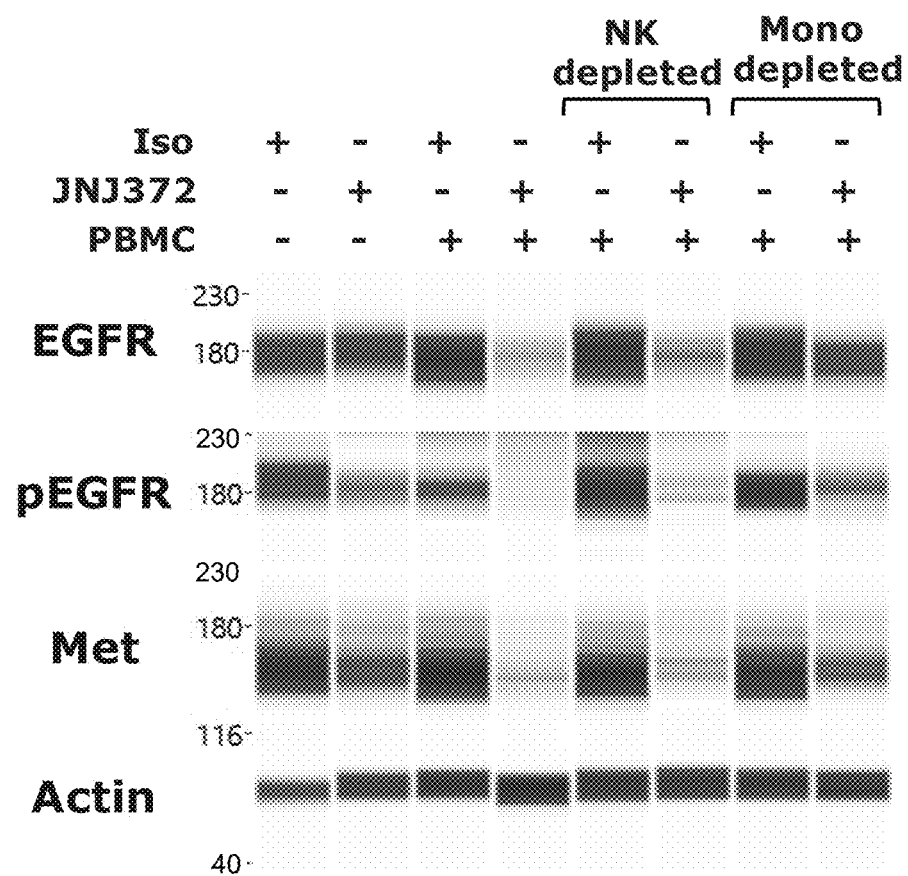
FIG. 16 shows the image from capillary based electrophoresis (Simple Western using PeggySue) detecting EGFR, c-Met and pEGFR protein levels in NCI-H1975 cells treated with JNJ-372 or isotype control and cultured for 48 hours in the presence or absence of NK cell depleted PBMCs or monocyte (mono) depleted PBMCs from one donor as indicated in the Figure.
Figure 17:
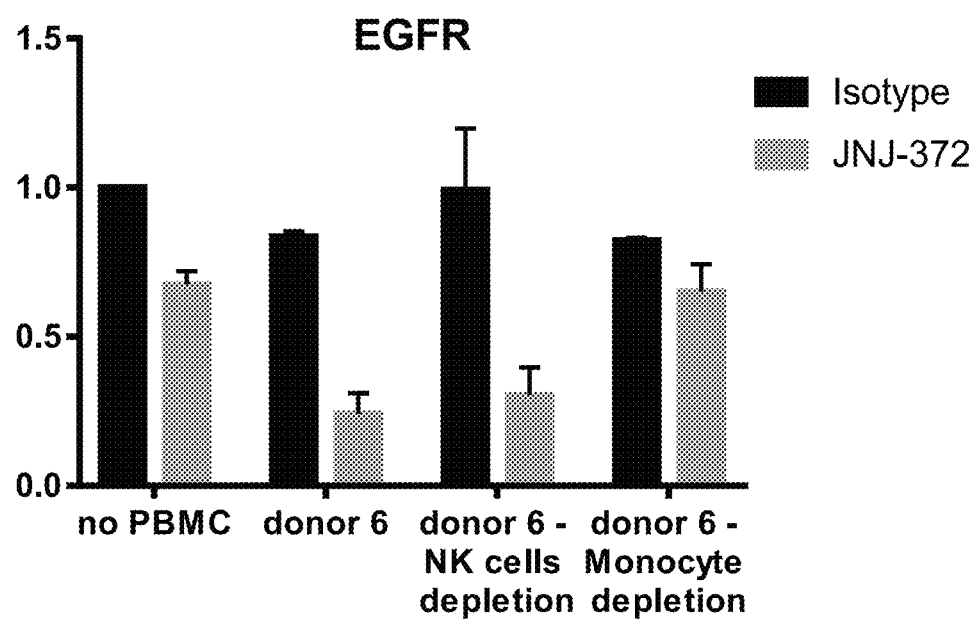
FIG. 17 shows the relative amount of EGFR (normalized to loading control Actin) in NCI-H1975 cells treated with JNJ-372 or isotype control and cultured for 48 hours in the presence or absence of NK cell depleted PBMCs or monocyte (mono) depleted PBMCs from one donor as indicated in the Figure.
Figure 18:
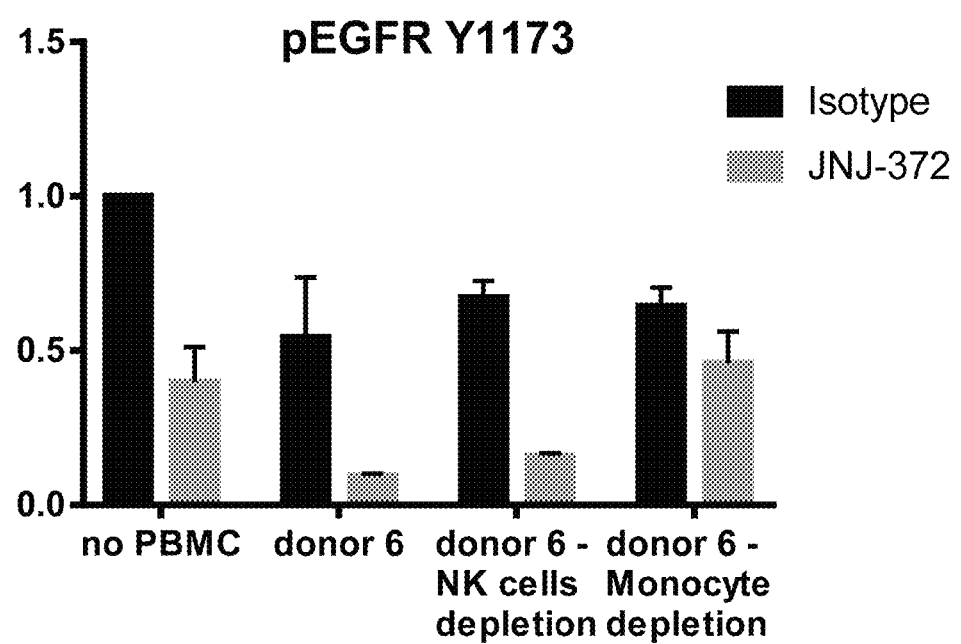
FIG. 18 shows the relative amount of pEGFR (pY1173) (normalized to loading control Actin) in NCI-H1975 treated with JNJ-372 or isotype control and cultured for 48 hours in the presence or absence of NK cell depleted PBMCs or monocyte (mono) depleted PBMCs from one donor as indicated in the Figure.
Figure 19:
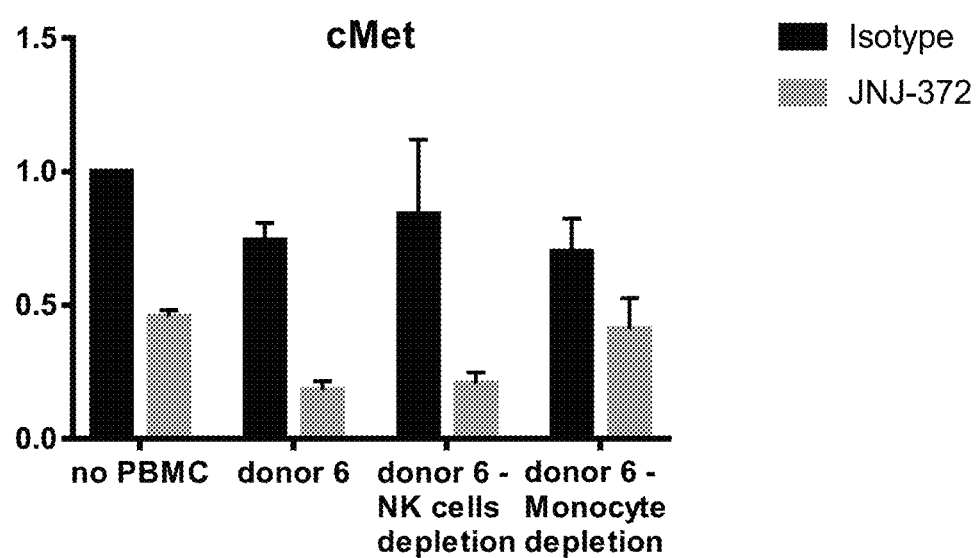
FIG. 19 shows the relative amount of c-Met (normalized to loading control Actin) in NCI-H1975 treated with JNJ-372 or isotype control and cultured for 48 hours in the presence or absence of NK cell depleted PBMCs or monocyte (mono) depleted PBMCs from one donor as indicated in the Figure.

While depletion of the NK cells only had a marginal effect, depletion of the monocytes from the PBMCs significantly reversed the ability of PBMCs to potentiate JNJ-372 mediated signal downmodulation. FIG. 16 shows the image from capillary based electrophoresis (Simple Western using Peggy Sue) detecting EGFR, c-Met and pEGFR protein levels in NCI-H1975 cells treated with JNJ-372 or isotype control and cultured for 48 hours in the presence or absence of NK cell depleted PBMCs or monocyte (mono) depleted PBMCs from one donor as indicated in the Figure. FIG. 17 shows the relative amount of EGFR in NCI-H1975 treated with JNJ-372 or isotype control and cultured for 48 hours in the presence or absence of NK cell depleted PBMCs or monocyte (mono) depleted PBMCs from one donor as indicated in the Figure. FIG. 18 shows the relative amount of pEGFR (pY1173) in NCI-H1975 treated with JNJ-372 or isotype control and cultured for 48 hours in the presence or absence of NK cell depleted PBMCs or monocyte (mono) depleted PBMCs from one donor as indicated in the Figure. FIG. 19 shows the relative amount of c-Met in NCI-H1975 treated with JNJ-372 or isotype control and cultured for 48 hours in the presence or absence of NK cell depleted PBMCs or monocyte (mono) depleted PBMCs from one donor as indicated in the Figure. Samples were normalized to the amount of the loading control Actin present in each sample and then to the control (no treatment) sample.

Figure 20:
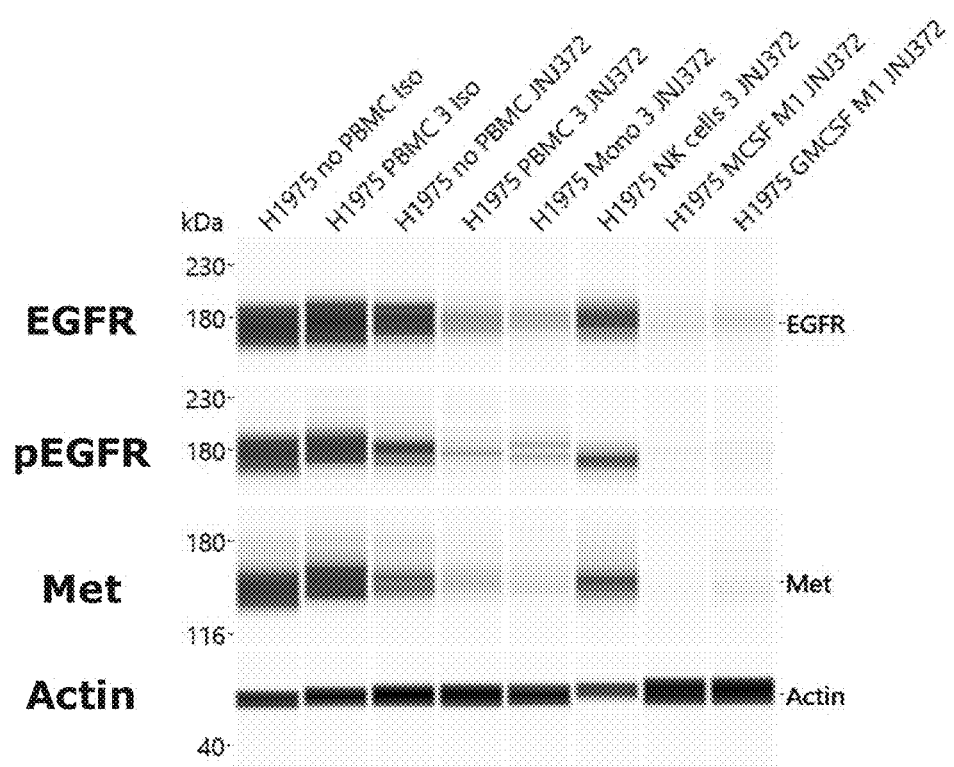
FIG. 20 shows the image from capillary based electrophoresis (Simple Western using PeggySue) detecting EGFR, c-Met and pEGFR protein levels in NCI-H1975 cells treated with JNJ-372, JNJ-372.IgG2sigma or isotype control for 48 hours in the presence or absence of PBMCs, isolated NK cells, isolated monocytes, MCSF differentiated M1 macrophages or GMCSF differentiated M1 macrophages from the same donor as indicated in the Figure.
Figure 21:
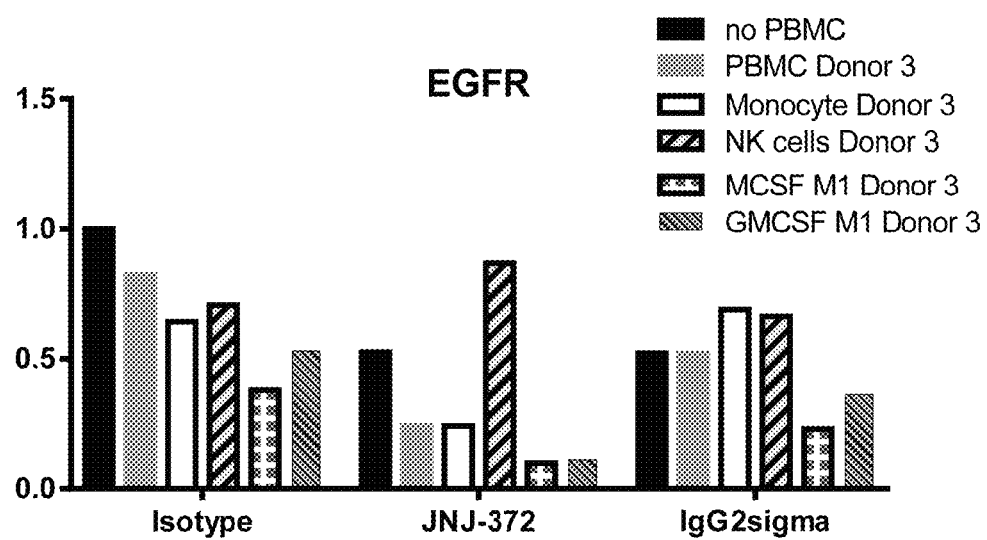
FIG. 21 shows the relative amount of EGFR (normalized to loading control Actin) in NCI-H1975 cells treated with JNJ-372, JNJ-372.IgG2sigma or isotype control for 48 hours in the presence or absence of PBMCs, monocytes, MCSF differentiated M1 macrophages or GMCSF differentiated M1 macrophages isolated from the same donor as indicated in the Figure.
Figure 22:
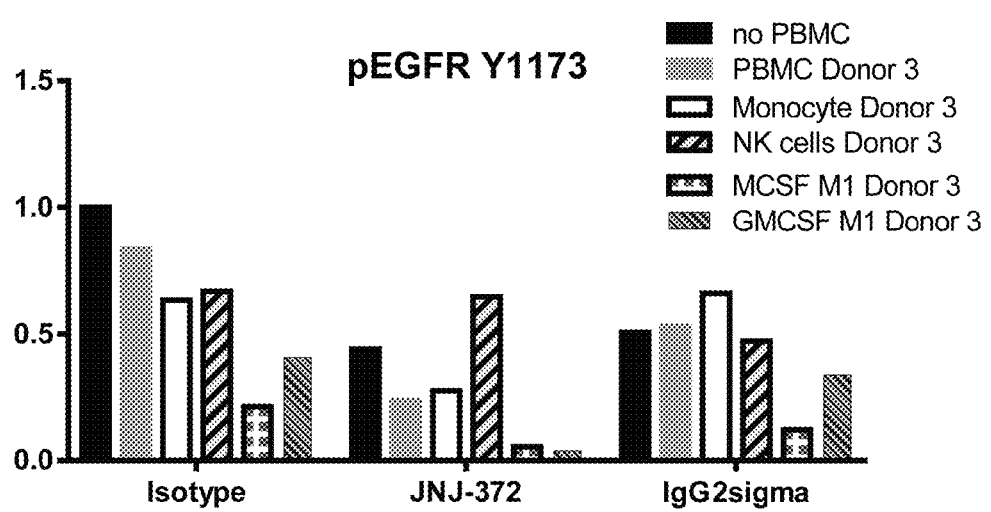
FIG. 22 the shows the relative amount of pEGFR (pY1173) (normalized to loading control Actin) in NCI-H1975 cells treated with JNJ-372, JNJ-372.IgG2sigma or isotype control for 48 hours in the presence or absence of PBMCs, monocytes, MCSF differentiated M1 macrophages or GMCSF differentiated M1 macrophages isolated from the same donor as indicated in the Figure.
Figure 23:
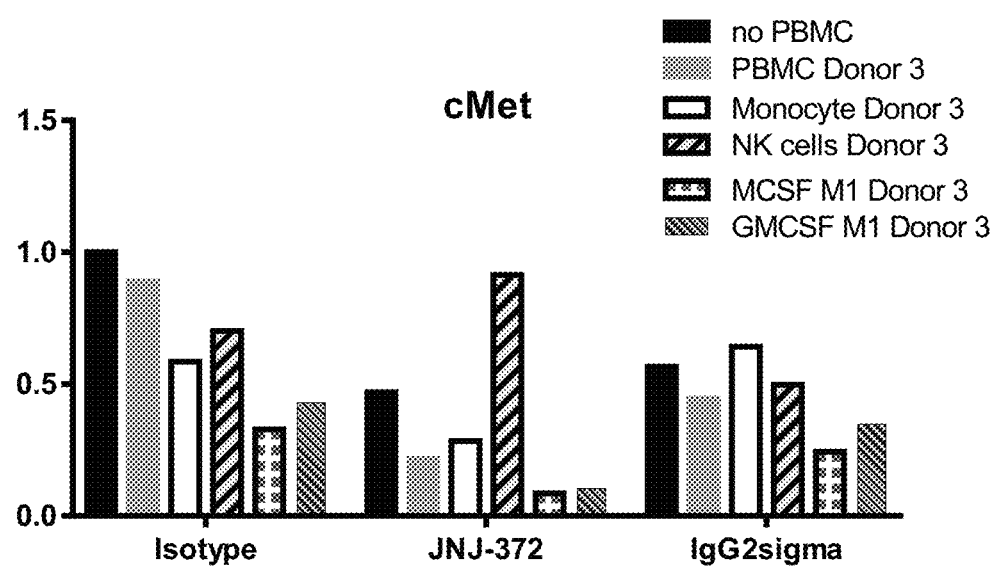
FIG. 23 the shows the relative amount of c-Met (normalized to loading control Actin) in NCI-H1975 cells treated with JNJ-372, JNJ-372.IgG2sigma or isotype control for 48 hours in the presence or absence of PBMCs, monocytes, MCSF differentiated M1 macrophages or GMCSF differentiated M1 macrophages isolated from the same donor as indicated in the Figure.

To assess the role of myeloid compartment further, the effect of monocytes or M1 macrophages isolated from one PBMC donor on JNJ-372 Fc interaction driven EGFR/c-Met downregulation was assessed. M1 macrophages were obtained by differentiating the monocytes two ways, with M-CSF and GM-CSF to assess any potential differential effects. H1975 cells were treated with 10 µg/mL isotype, JNJ-372 or JNJ-372.IgG2sigma and cultured in the presence or absence of PBMCs from one donor at E:T ratio of 10:1 (for PBMCs) or 5:1 (for individual immune cells (monocytes, NK cells, MCSF M1 or GMCSF M1 macrophages) for 48 hours. The presence of PBMCs enhanced JNJ-372 mediated downregulation of EGFR, pEGFR and c-Met proteins. While NK cells did not have a significant effect, isolated monocytes or M1 macrophages (differentiated by M-CSF or GM-CSF) from the same PBMC donor significantly enhanced the ability of JNJ-372 mediated signal downmodulation. This suggested that the myeloid lineage is sufficient for Fc interaction and PBMC mediated enhancement in JNJ-372 signal downregulation. FIG. 20 shows the image from capillary based electrophoresis (Simple Western using PeggySue) detecting EGFR, c-Met and pEGFR protein levels in NCI-H1975 cells treated with JNJ-372 or isotype control and for 48 hours in the presence or absence of PBMCs, isolated monocytes isolated NK cells, MCSF differentiated M1 macrophages or GMCSF differentiated M1 macrophages from the same donor as indicated in the Figure. FIG. 21 shows the relative amount of EGFR in NCI-H1975 cells treated with JNJ-372, JNJ-372. IgG2sigma or isotype control for 48 hours in the presence or absence of PBMCs, NK cells, monocytes, MCSF M1 macrophages or GMCSF M1 macrophages isolated from the same donor as indicated in the Figure. FIG. 22 the shows the relative amount of pEGFR (pY1173) in NCI-H1975 cells treated with JNJ-372, JNJ-372.IgG2sigma or isotype control for 48 hours in the presence or absence of PBMCs, NK cells, monocytes, MCSF M1 macrophages or GMCSF M1 macrophages isolated from the same donor as indicated in the Figure. FIG. 23 the shows the relative amount of c-Met in NCI-H1975 cells treated with JNJ-372, JNJ-372.IgG2sigma or isotype control for 48 hours in the presence or absence of PBMCs, NK cells, monocytes, MCSF M1 macrophages or GMCSF M1 macrophages isolated from the same donor as indicated in the Figure. Samples were normalized to the amount of the loading control Actin present in each sample and then to the control (no treatment) sample.

Figure 24:
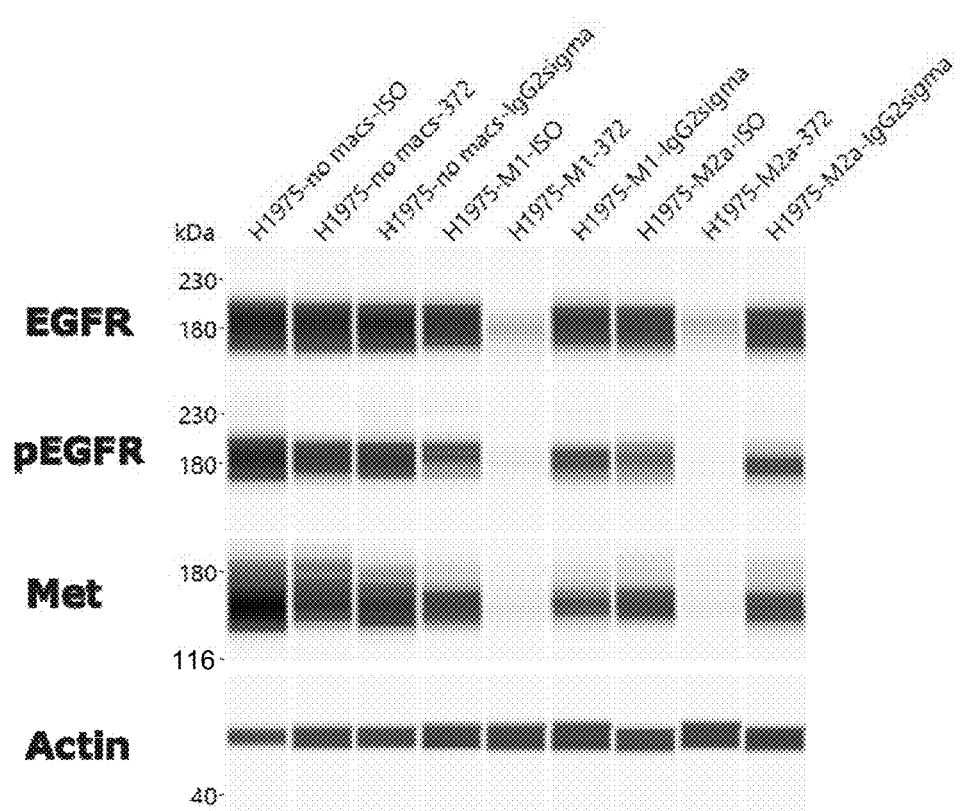
FIG. 24 shows the image from capillary based electrophoresis (Simple Western using PeggySue) detecting EGFR, c-Met and pEGFR protein levels in NCI-H1975 cells treated with JNJ-372, JNJ-372.IgG2sigma or isotype control and cultured in the presence of M1 macrophages (M1) or M2a macrophages (M2a) as indicated in the Figure. ISO: isotype control, 372: JNJ-372, IgG2sigma: JNJ-372.IgG2sigma.
Figure 25:
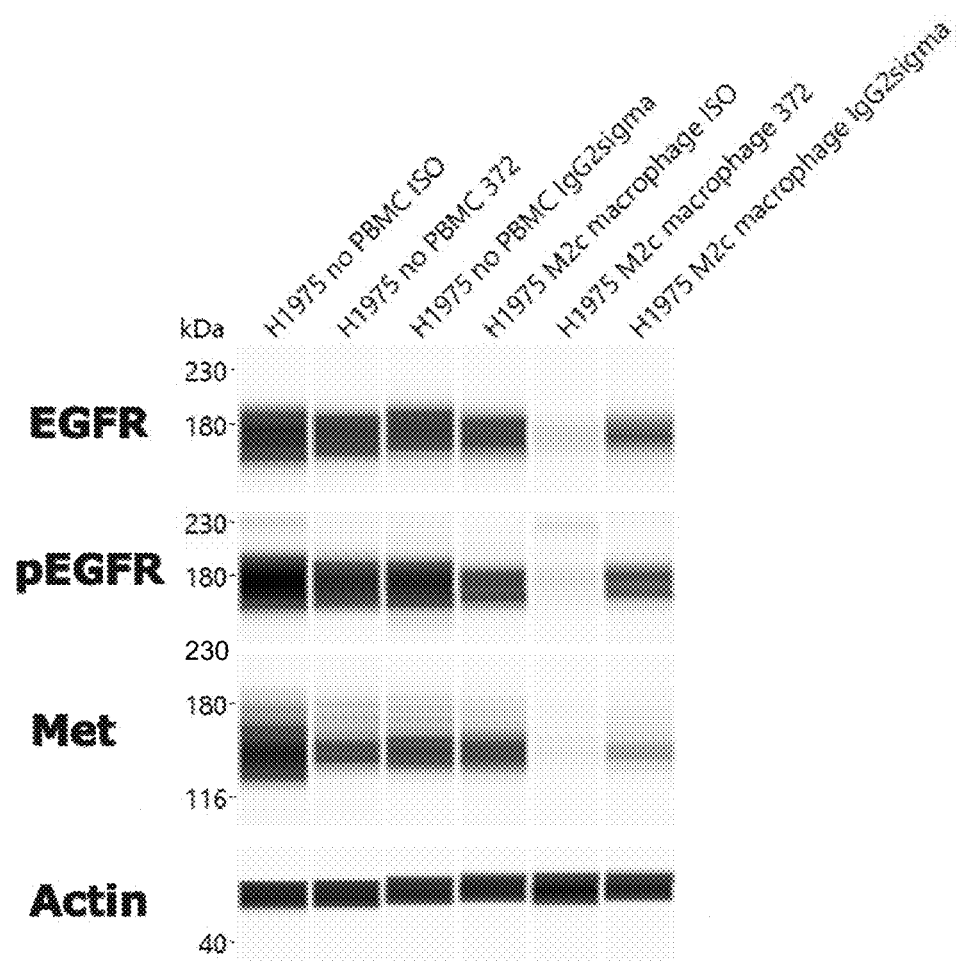
FIG. 25 shows the image from capillary based electrophoresis (Simple Western using PeggySue) detecting EGFR, c-Met and pEGFR protein levels in NCI-H1975 cells treated with JNJ-372, JNJ-372.IgG2sigma or isotype control and cultured for 48 hours in the presence or absence of M2c macrophages (M2c) as indicated in the Figure. ISO: isotype control, 372: JNJ-372, IgG2sigma: JNJ-372.IgG2sigma.

The effect of the different macrophage subtypes in JNJ-372 Fc interaction driven EGFR/c-Met downregulation was subsequently assessed. Monocytes derived from one donor were differentiated into M1, M2a and M2c macrophages and their ability to potentiate JNJ-372-mediated EGFR/c-Met downmodulation was assessed. H1975 cells were treated with 10 µg/mL isotype, JNJ-372 or JNJ-372.IgG2sigma and cultured in the presence or absence of M1, M2a or M2c macrophages obtained by differentiation monocytes from one donor at E:T ratio of 5:1 for 48 hours. The presence of M1, M2a and M2c all significantly enhanced JNJ-372 mediated downregulation of EGFR, pEGFR and c-Met proteins. FIG. 24 shows the image from capillary based electrophoresis (Simple Western using PeggySue) detecting EGFR, c-Met and pEGFR protein levels in NCI-H1975 cells treated with JNJ-372, JNJ-372.IgG2sigma or isotype control and cultured in the presence of M1 macrophages (M1) or M2a macrophages (M2a) as indicated in the Figure. FIG. 25 shows the image from capillary based electrophoresis (Simple Western using PeggySue) detecting EGFR, c-Met and pEGFR levels in NCI-H1975 cells treated with JNJ-372, JNJ-372.IgG2sigma or isotype control and cultured for 48 hours in the presence or absence of M2c macrophages (M2c) as indicated in the Figure.

EXAMPLE 4

Figure 26:
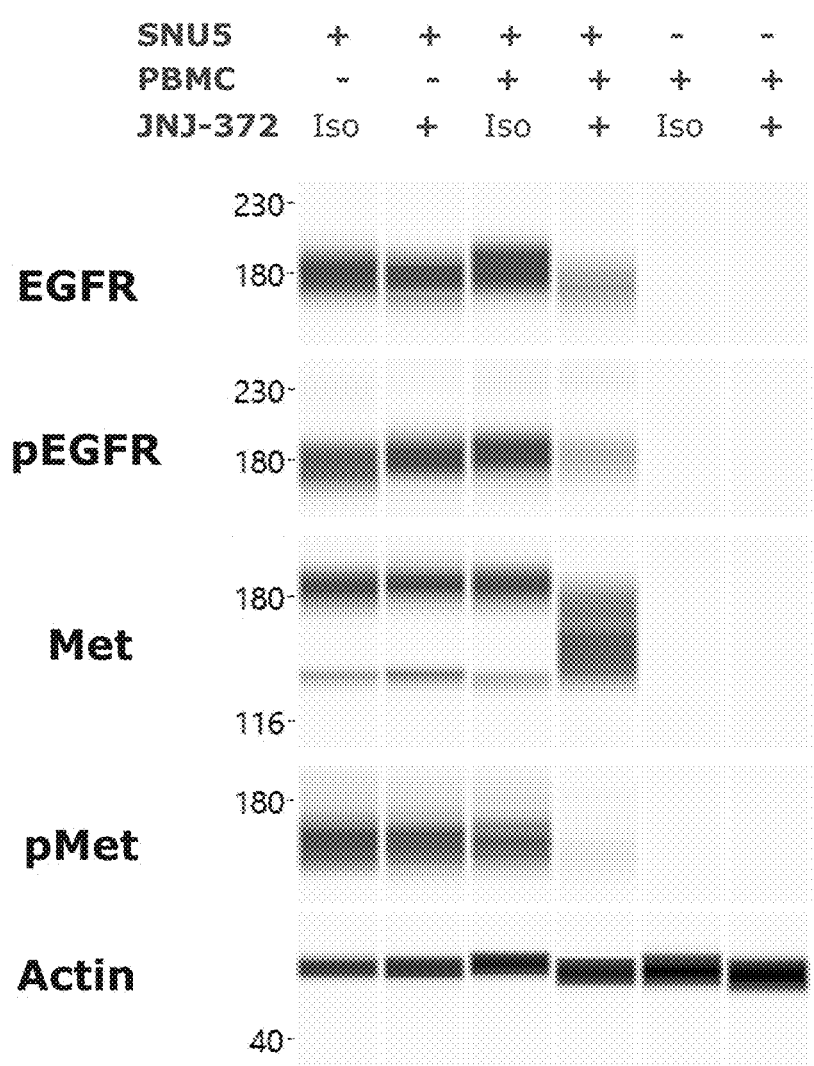
FIG. 26 shows the image from capillary based electrophoresis (Simple Western using Peggy Sue) detecting EGFR, c-Met, pEGFR and pMet protein levels in SNU-5 cells treated with JNJ-372 or isotype control and cultured in the presence or absence of PBMCs as indicated in the Figure.
Figure 27:
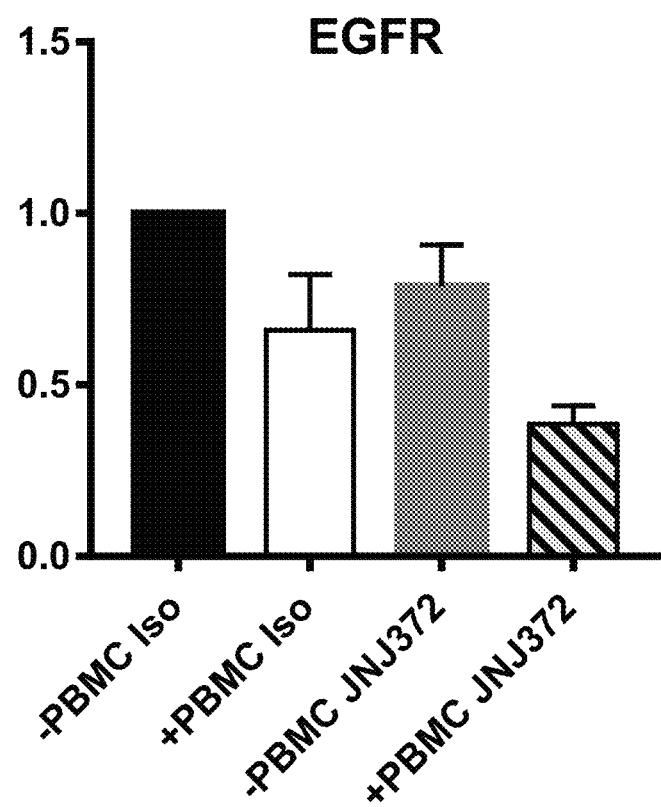
FIG. 27 shows the relative amount of EGFR (normalized to loading control Actin) in SNU-5 cells treated with JNJ-372 or isotype control and cultured for 48 hours in the presence or absence of PBMCs as indicated in the Figure.
Figure 28:
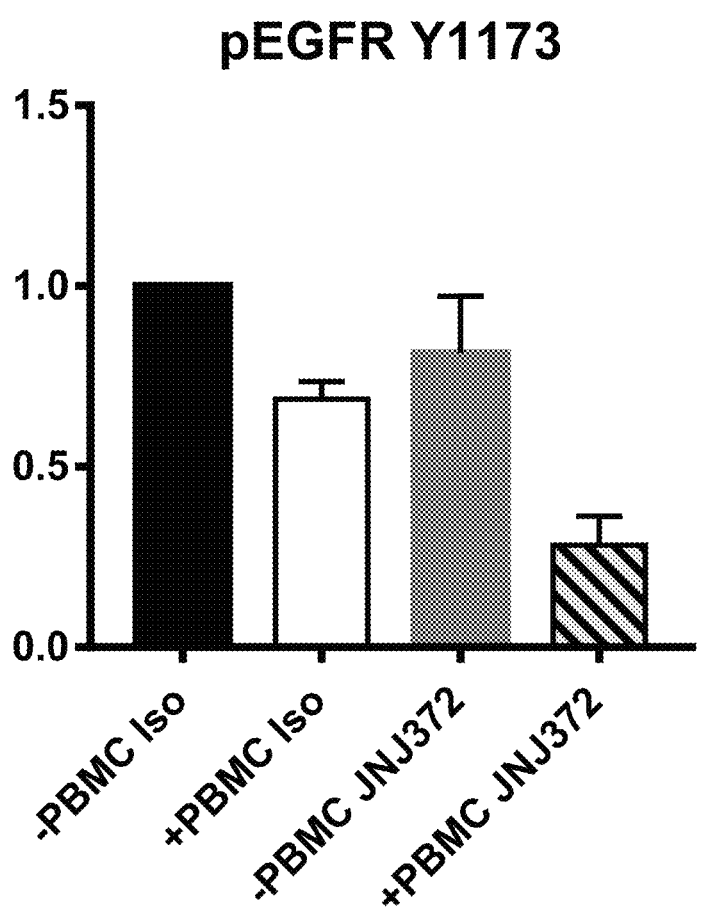
FIG. 28 shows the relative amount of pEGFR (pY1173) (normalized to loading control Actin) in SNU-5 cells treated with JNJ-372 or isotype control and cultured for 48 hours in the presence or absence of PBMCs as indicated in the Figure.
Figure 29:
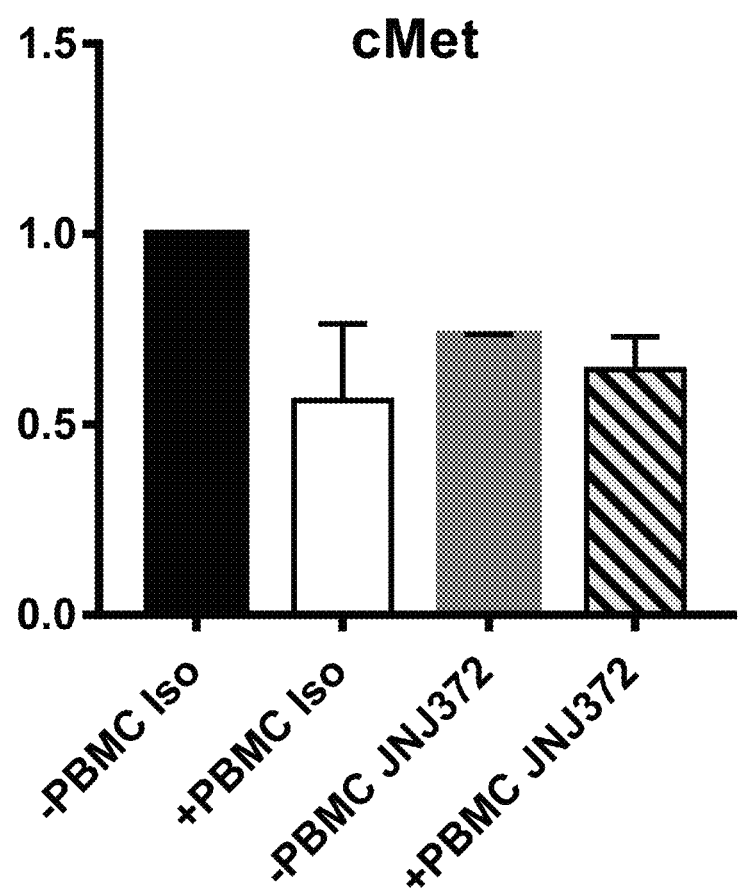
FIG. 29 shows the relative amount of c-Met (normalized to loading control Actin) in SNU-5 cell culture samples cultured for 48 hours in the presence or absence of JNJ-372, isotype control or PBMCs as indicated in the Figure.
Figure 30:
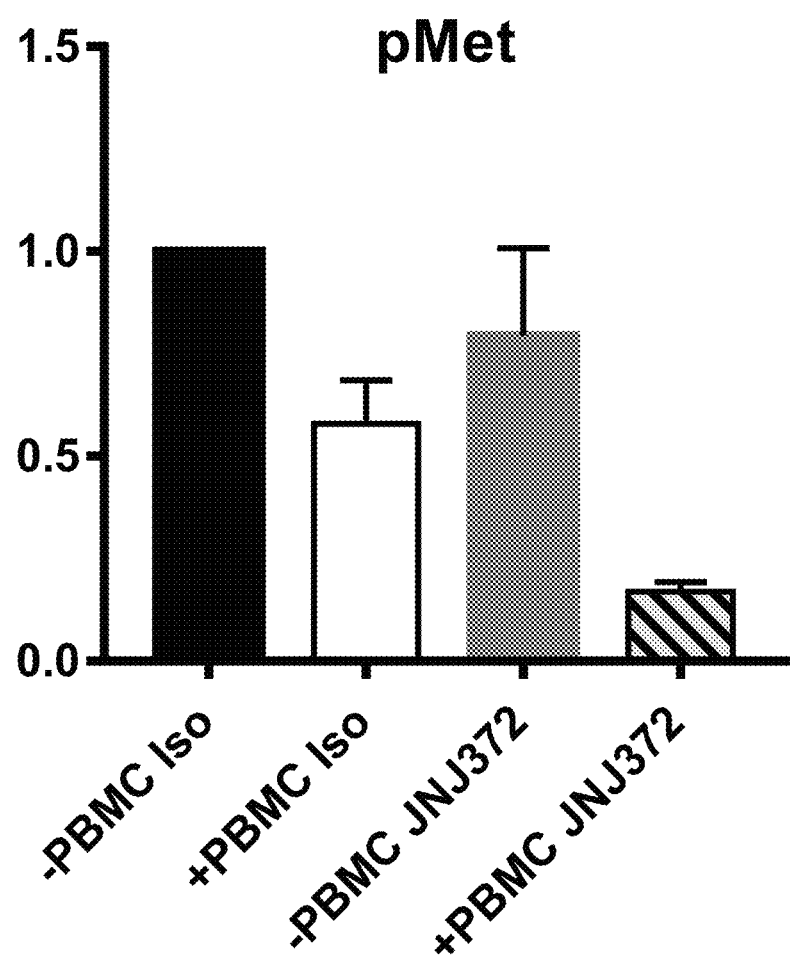
FIG. 30 shows the relative amount of pMet (pY1234/1235) (normalized to loading control Actin) in SNU-5 cells treated with JNJ-372 or isotype control and cultured for 48 hours in the presence or absence of PBMCs as indicated in the Figure.

JNJ-372-Mediated Downregulation of EGFR and C-Met Protein and Their Downstream Signaling is Mediated by Fc Interactions in C-Met Amplified Tumor Cell Lines SNU-5 (c-Met amplified cell line) cells were treated with 10 µg/mL, JNJ-372 or isotype control and cultured in the presence or absence of PBMCs from one donor at E:T ratio of 10:1 for 48 hours. The addition of PBMCs potentiated the ability of JNJ-372 to downmodulate EGFR, pEGFR, c-Met and p-Met. FIG. 26 shows the image from capillary based electrophoresis (Simple Western using Peggy Sue) detecting EGFR, c-Met and pEGFR protein levels in SNU-5 cells treated with JNJ-372 or isotype control and cultured in the presence or absence of PBMCs as indicated in the Figure. FIG. 27 shows the relative amount of EGFR in SNU-5 cells treated with JNJ-372 or isotype control and cultured in the presence or absence of PBMCs as indicated in the Figure. FIG. 28 shows the relative amount of pEGFR (pY1173) in SNU-5 cells treated with JNJ-372 or isotype control and cultured in the presence or absence of PBMCs as indicated in the Figure. FIG. 29 shows the relative amount of c-Met in SNU-5 cell culture samples cultured for 48 hours in the presence or absence of JNJ-372, isotype control or PBMCs as indicated in the Figure. FIG. 30 shows the relative amount of pMet (pY1234/1235) in SNU-5 cells treated with JNJ-372 or isotype control and cultured in the presence or absence of PBMCs as indicated in the Figure. Samples were normalized to the amount of the loading control Actin present in each sample and then to the control (no treatment) sample.

EXAMPLE 5

JNJ-372 Fc Interaction with FcγR Mediated Tumor Growth Inhibition in Vivo

The role and relevance of Fc/FcγR interactions was then evaluated in vivo using H1975 and SNU5 cell line xenograft models.

The NCI-H1975 cell line was subcutaneously implanted into 6-8 week old female BALB/c nude mice (CAnN.Cg-Foxnl$^{nmi}$/Crl, Charles River Laboratories, Wilmington, Ma.). When tumors were an average of 72±8 7 mm³, intraperitoneal anti-mCSF-1R antibody (400 µg/mouse) was administered thrice weekly for the duration of the study, beginning five days prior to compound dosing initiation to facilitate macrophage depletion. At day 5, when tumors were an average of 102±36.6 mm³, they were treated twice weekly by intraperitoneal dosing with isotype control Ab (10 mg/kg), JNJ-372 (10 mg/kg), or JNJ-372.IgG2sigma (10 mg/kg). Tumors were sampled from a cohort of mice to monitor macrophage infiltration following two doses of compound. The SNU5 cell line was subcutaneously implanted into 7-8 week old female CB17/SCID mice (HFK Bio-Technology Co. Ltd., Beijing, China). When tumors were an average of 155±21 4 mm³, mice were treated twice weekly with intraperitoneal Phosphate Buffered Saline (PBS), JNJ-372 (5 mg/kg), or JNJ-372.IgG2sigma (5 mg/kg), for three weeks. For both studies, tumor measurements and body weights were recorded twice weekly for the duration of each study. Tumor growth inhibition (TGI) was calculated on the final day where >80% control mice remained on study, using the calculation [1-(T/C)]*100. All in vivo experiments were done in accordance with the Johnson and Johnson Institutional Animal Care and Use Committee and the Guide for Care and Use of Laboratory Animals.

Figure 31:
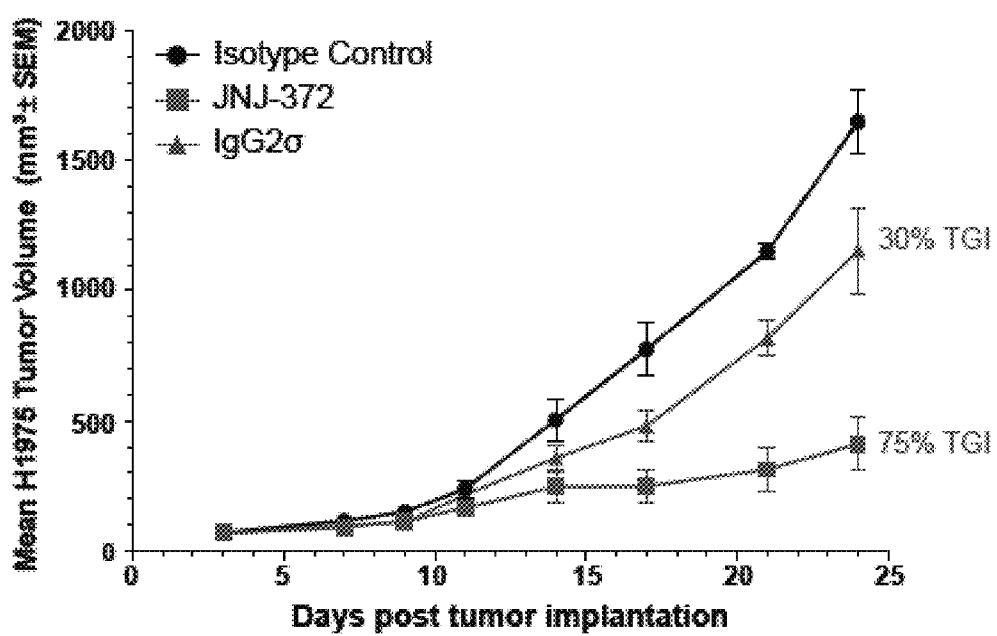
FIG. 31 shows tumor volumes of subcutaneously injected H1975 cell line xenograft tumors treated with 10 mg/kg isotype control (n=8), JNJ-372 (n=8) or JNJ-372.IgG2sigma (IgG2σ in the Figure) (n=8) for 3 weeks BIW. % TGI was calculated at day 24.
Figure 32:
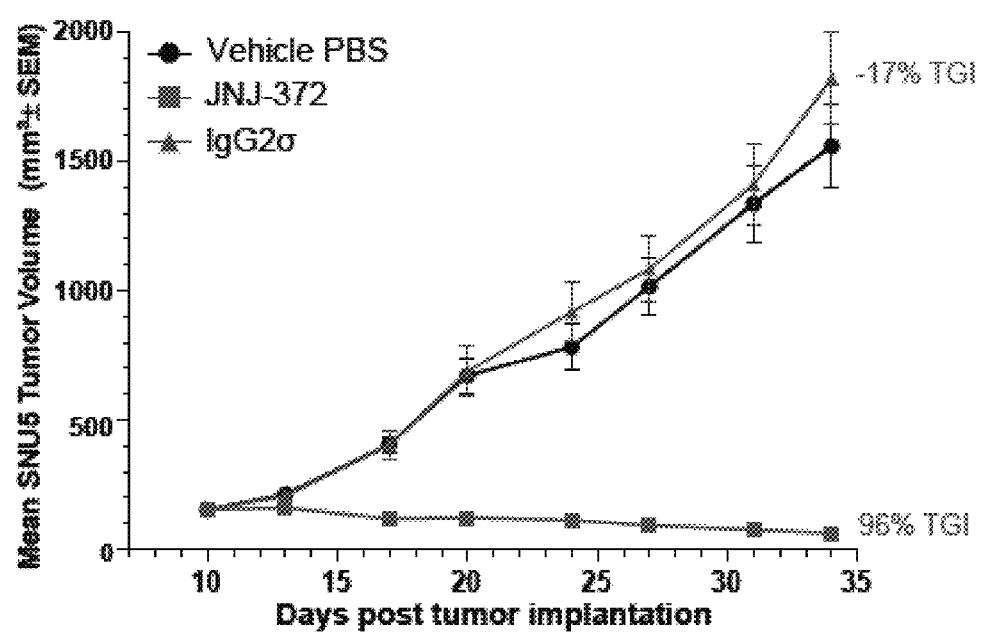
FIG. 32 shows tumor volumes of subcutaneously injected SNUS cell line xenograft tumors treated with vehicle (PBS) (n=8), 5 mg/kg JNJ-372 (n=8) or JNJ-372.IgG2sigma (IgG2σ in the Figure) (n=8) for 3 weeks BIW. % TGI was calculated at day 34. All data represented as Mean±S.E.M within each treatment group.

In the H1975 model, JNJ-372 treatment resulted in tumor growth inhibition (TGI) of 75% as compared to isotype control (FIG. 31). However, JNJ-372.IgG2sigma was considerably less effective, with a TGI of only 30% (FIG. 31). Similarly, JNJ-372 treatment was highly effective in reducing tumor growth in the MET amplified SNUS model with a TGI of 96%, whereas JNJ-372.IgG2sigma treatment was ineffective (TGI of −17%) (FIG. 32). No effects on mouse body weight were seen with antibody treatments in either of these tumor models (FIG. 32).

EXAMPLE 6

Fc Interaction Induced NK Cell-Mediated ADCC but Not CDC

Figure 33:
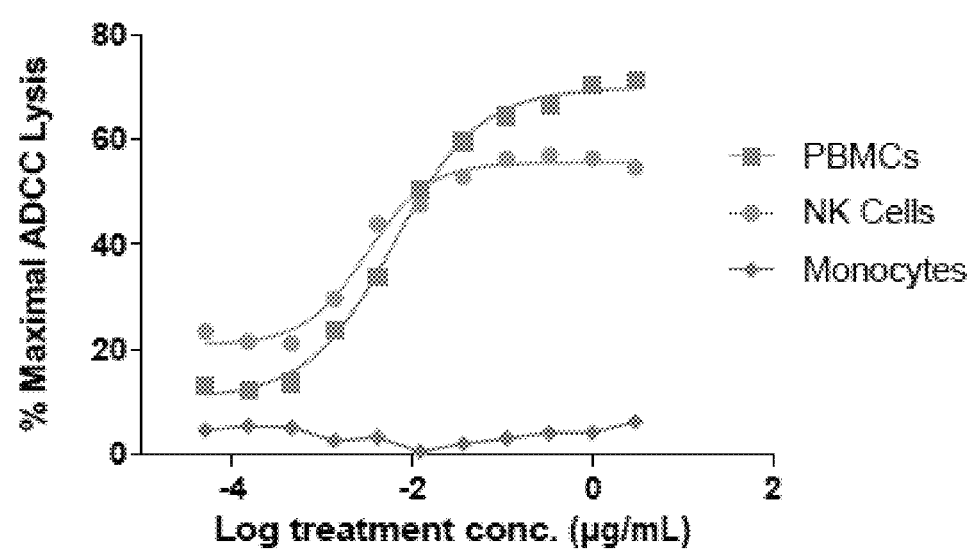
FIG. 33 shows BATDA-loaded H1975 cells treated for 2 hours with JNJ-372 in presence of PBMCs, NK cells or monocytes isolated from the same donor at E:T ratios of 25:1, 5:1, and 5:1, respectively and ADCC lysis measured by Europium release.

The ability of JNJ-372 to induce different Fc effector functions was examined. JNJ-372-induced ADCC was measured using a Europium release assay in the presence of PBMCs from seven different donors. Antibody-mediated H1975 cell lysis was variable across donors, with some donors exhibiting ~60-70% ADCC activity, while others had no measurable ADCC activity (data not shown). To assess the contribution of Fc/FcγR engagement, H1975 cells were treated with isotype control, JNJ-372 or JNJ-372.IgG2sigma in presence of PBMCs from 2 donors. While JNJ-372 induced dose-dependent ADCC, no cell death was observed with isotype control or JNJ-372.IgG2sigma treatment (data not shown). To determine the immune cell subtype within the PBMCs responsible for JNJ-372-induced ADCC, ADCC lysis elicited in the presence of PBMCs versus isolated NK cells or isolated monocytes from the same donor was assessed. Both PBMCs and NK cells, but not isolated monocytes, induced JNJ-372-dependent ADCC lysis (FIG. 33), indicating that NK cells are responsible for JNJ-372-induced ADCC activities. No measurable CDC activity was observed with JNJ-372 or JNJ-372. IgG2sigma towards H1975 and H292 NSCLC cell lines (data not shown), suggesting that JNJ-372 does not induce CDC against these NSCLC cell lines.

EXAMPLE 7

Effect of Macrophages on JNJ-372 Meidated Tumor Cell Killing in Vivo

Figure 34:
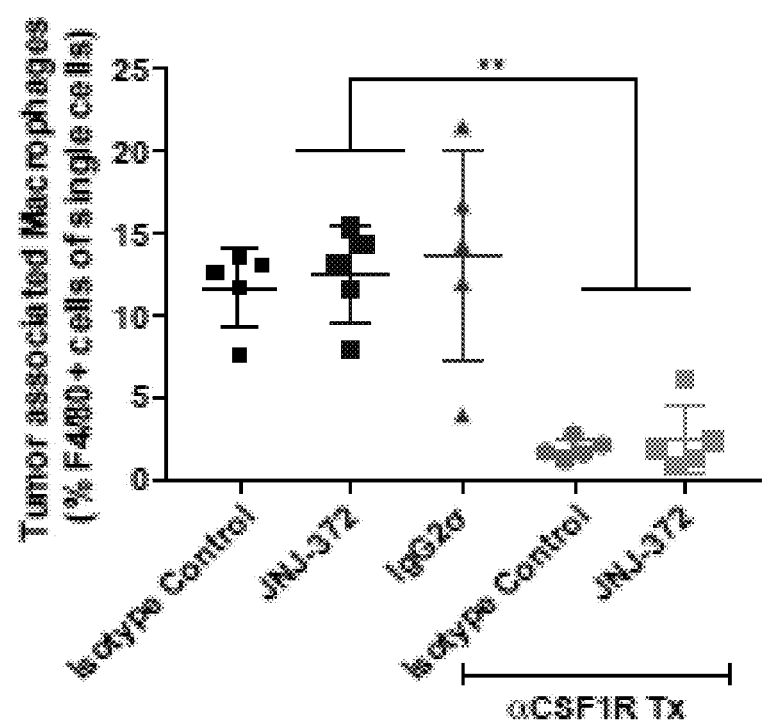
FIG. 34 shows the number of tumor-associated macrophages using multi-color flow cytometry analysis of H1975 tumor samples isolated 24 hrs after two doses of 10 mg/kg isotype, JNJ-372 or JNJ-372.IgG2sigma treatment (n=5 mice/treatment) to examine the percentage (%) of macrophages (CD45+ CD11b+ Ly6G– Ly6C– F4/80+) within the tumor post depletion with anti-mouse CSF1R antibody.
Figure 35:
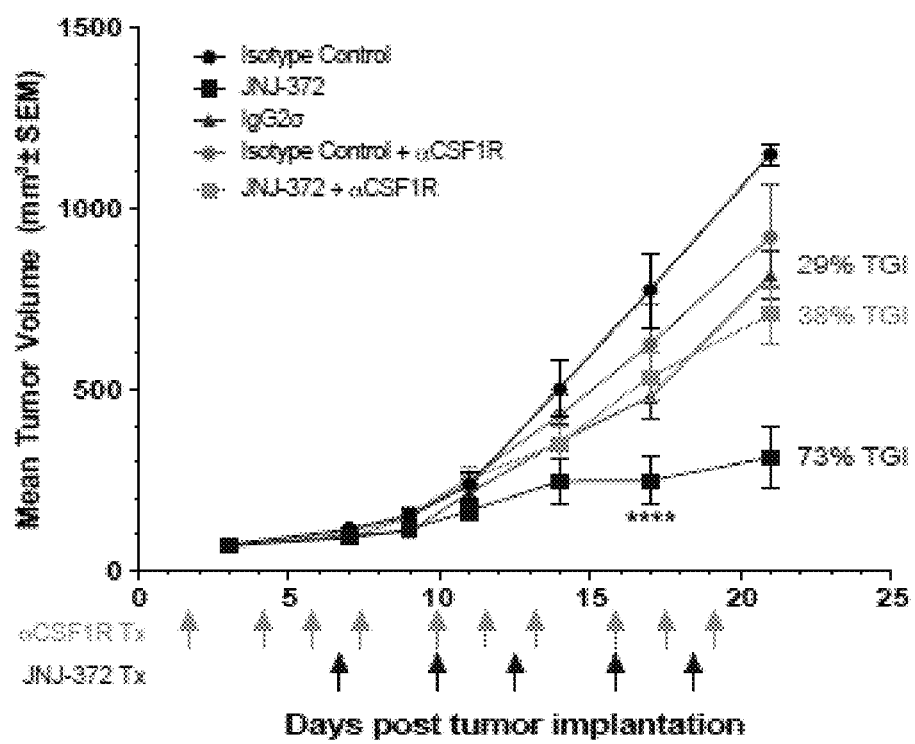
FIG. 35 shows tumor volumes of subcutaneously injected H1975 cell line xenograft tumors treated with 10 mg/kg JNJ-372, JNJ-372.IgG2sigma or isotype (n=8 mice per treatment group) for 3 weeks BIW in combination with anti-mouse CSF1R or its Isotype control thrice weekly to deplete macrophages. % TGI was calculated on day 21 and ****, p value<0.0001 was calculated by 2way ANOVA on day 17 (when all groups had all mice in the study)

To examine the role of macrophages in vivo, tumor associated macrophages were depleted in mice harboring H1975 xenograft tumors using anti-CSF1R antibody and JNJ-372 efficacy measured. Treatment with anti-CSF1R antibody showed significant reduction in TAMs compared to untreated (, p<0.002), with macrophages depleted from 11-15% to ~2% (FIG. 34). The animals were then treated with isotype control, JNJ-372, or JNJ-372.IgG2sigma for 3 weeks, with no mouse body weight loss observed in any groups (data not shown). As shown previously, treatment with JNJ-372 showed significantly higher anti-tumor efficacy compared to the isotype control (, p<0.0001) or JNJ-372.IgG2sigma treatment (, p=0.004) in non-CSF1R antibody-treated tumors (FIG. 35). Strikingly, depletion of tumor-associated-macrophages (anti-CS1R-treated) significantly reduced TGI from 72.8% to 38.5% (****, p<0.0001) (FIG. 35), suggesting that macrophages play a key role in mediating the anti-tumor efficacy of JNJ-372 in vivo.

These results demonstrated that macrophages are essential for anti-tumor efficacy in vivo.

EXAMPLE 8

JNJ-372 Fc Interaction with Immune Cells Induces Antibody Dependent Cytokine and Chemokine Release (ADCR)

Figure 36:
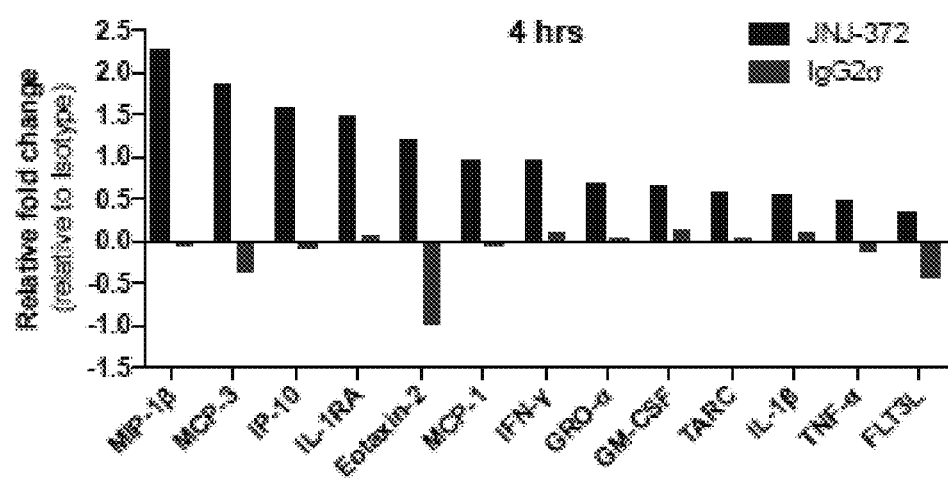
FIG. 36 shows bar graphs representing the relative fold change of indicated chemokines and cytokines produced by H1975 cells after 4 hour treatment with JNJ-372 or JNJ-372.IgG2sigma over isotype in the presence of PBMCs.
Figure 37:
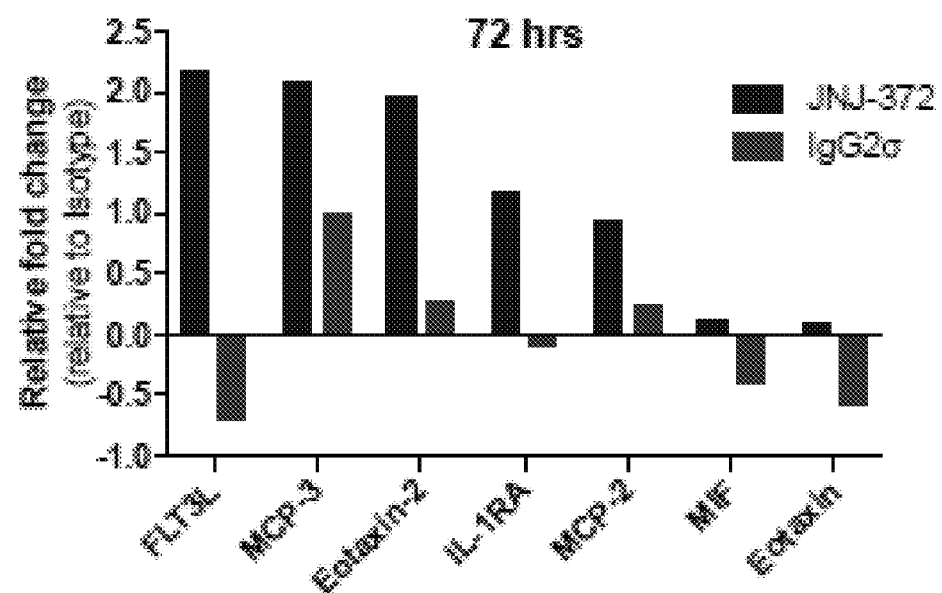
FIG. 37 shows bar graphs representing the relative fold change of indicated chemokines and cytokines produced by H1975 cells after 72 hour treatment with JNJ-372 or JNJ-372.IgG2sigma over isotype in the presence of PBMCs.

Interaction of the Fc region of therapeutic antibodies with FcγR on immune cells is known to induce secretion of chemokines and cytokines (ADCR) (Kinder et al., mAbs 7:494-504, 2015). A 71-plex MSD cytokine panel was utilized to assess chemokines and cytokines secreted upon treatment with isotype control, JNJ-372, or JNJ-372.IgG2sigma in the presence of absence of PBMCs for 4 or 72 hours. Distinct differences were observed in several secreted cytokines in a treatment- and timepoint-dependent manner; 32 out of the 71 cytokines and 42 out of 71 cytokines tested had a reliably measurable response (AUC) at 4 and 72 hours respectively. Further analysis focusing on cytokines with >1.5-fold difference between treatments showed that at 4 h (FIG. 36) and 72 h (FIG. 37) post-treatment, thirteen and seven cytokines, respectively, were upregulated upon JNJ-372 treatment compared to isotype control or JNJ-372.IgG2sigma in the co-culture of H1975+ PBMCs. Many of the altered cytokines belong to the family of chemotactic cytokines (CC chemokines) (FIG. 6B—MIP1β, MCP-1, MCP-3, Eotaxin, Eotaxin-2), which are known to function as chemo-attractants for innate immune cells, monocytes and macrophages (Graves et al., Crit Rev Oral Biol Med 6:109-18, 1995; Uguccioni et al., Eur J Immunol 25:64-8, 1995; Balkwill, Nat Rev Cancer 4: 540-50, 2004).

Figure 38:
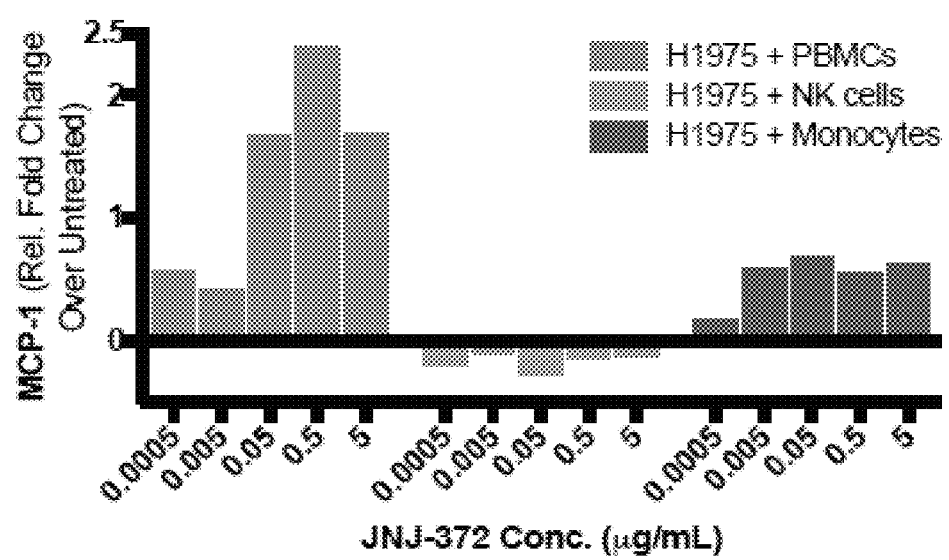
FIG. 38 shows relative fold change of MCP-1 productioton over untreated in H1975 cells treated with an indicated dose range of JNJ-372 for 4 hours in the presence of PBMCs (E:T=10:1) (first 5 bars from the left), NK cells (bars 6-10 from the left) or monocytes (first 5 bars from the right) at effetor:target ratio of 5:1 (E:T=5:1).
Figure 39:
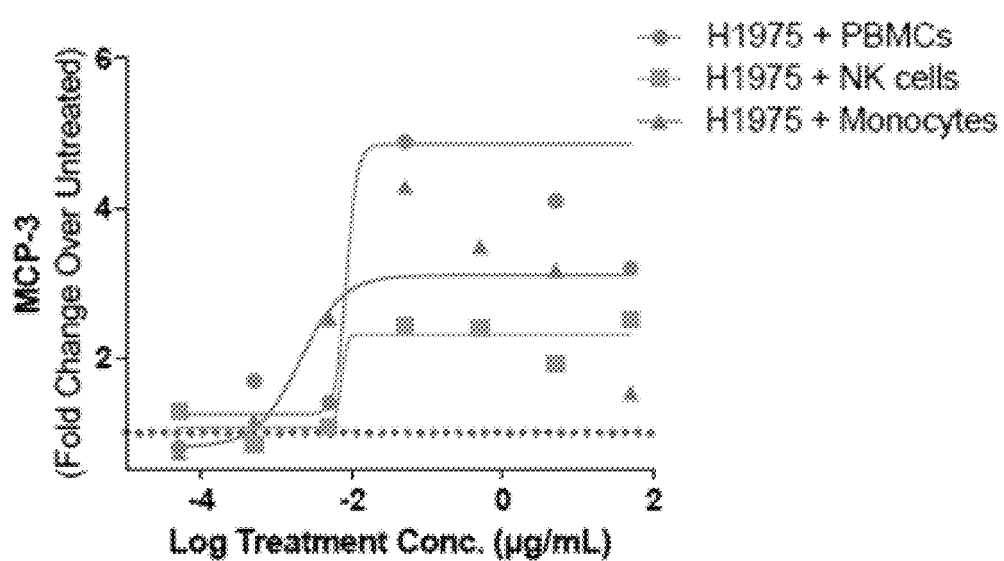
FIG. 39 shows dose-response curves from MSD based cytokine analysis measuring the fold change (compared to untreated controls) in levels of MCP-3 upon treatment of H1975 cells with JNJ-372 in the presence of PBMCs, NK cells or monocytes. Grey dotted line indicates the value of untreated control.
Figure 40:
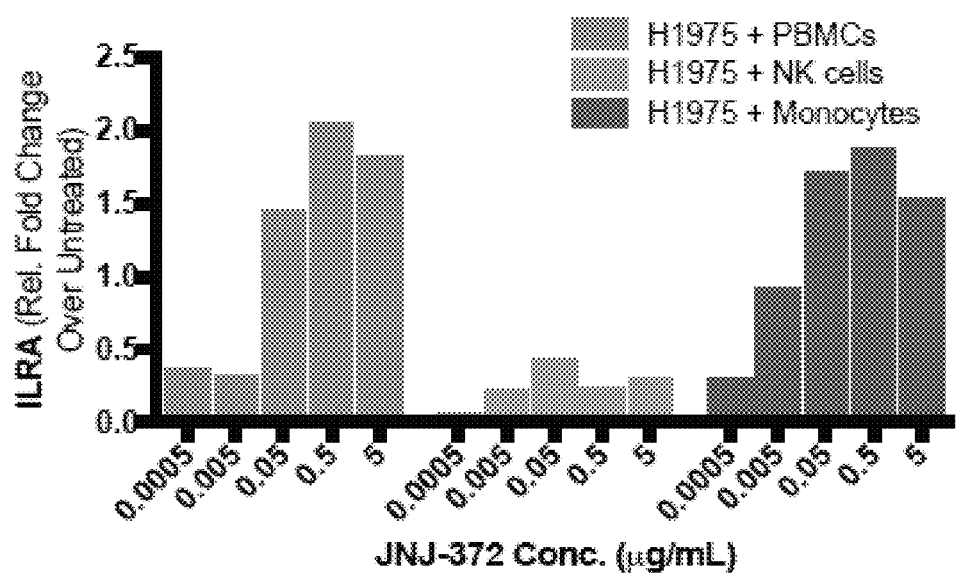
FIG. 40 shows relative fold change of IL1-RA (ILRA shown in the Figure) productioton over untreated in H1975 cells treated with an indicated dose range of JNJ-372 for 4 hours in the presence of PBMCs (E:T=10:1) (first 5 bars from the left), NK cells (bars 6-10 from the left) or monocytes (first 5 bars from the right) at effctor:target ratio of 5:1 (E:T=5:1).
Figure 41:
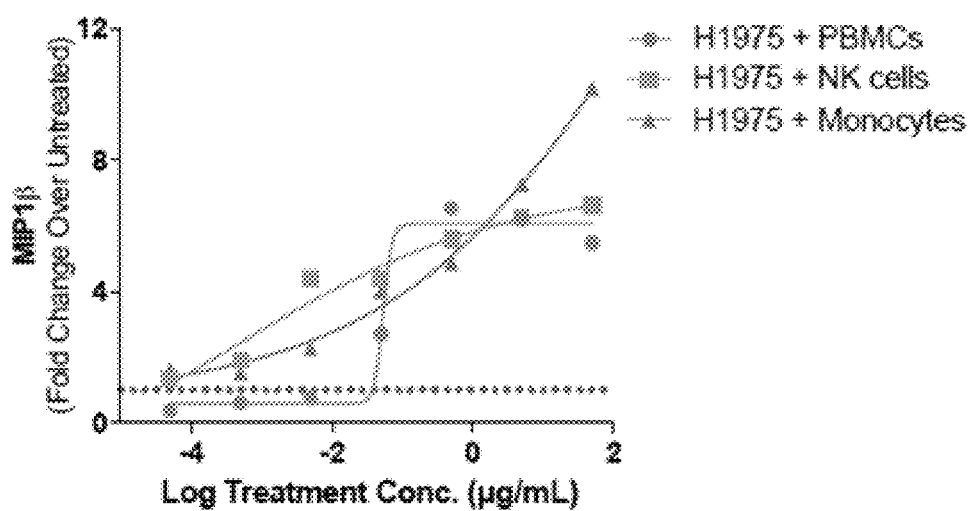
FIG. 41 shows dose-response curves from MSD based cytokine analysis measuring the fold change (compared to untreated controls) in levels of MIP-1β upon treatment of H1975 cells with JNJ-372 in the presence of PBMCs, NK cells or monocytes. Grey dotted line indicates the value of untreated control.
Figure 42:
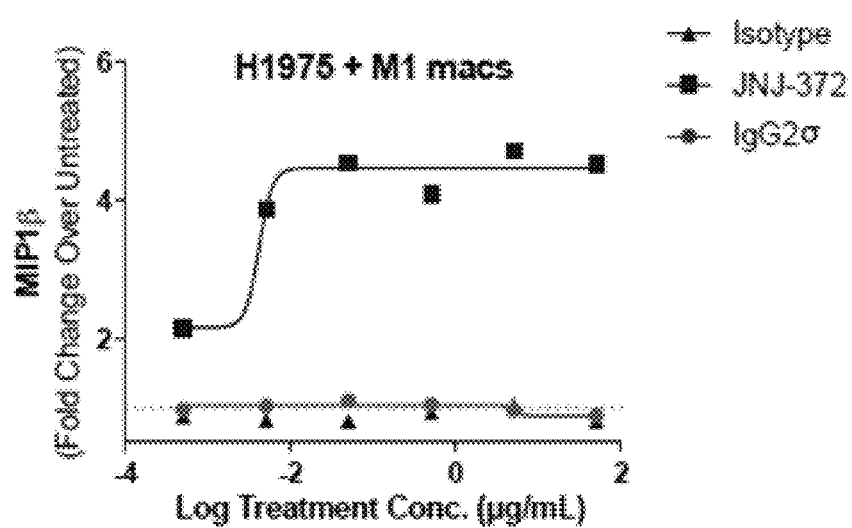
FIG. 42 shows dose-response curves from MSD based cytokine analysis measuring the fold change (compared to untreated controls) in levels of MIP-1β upon treatment of H1975 cells with JNJ-372, JNJ-372.IgG2sigma (IgG2σ in the Figure) or isotype control in the presence of M1 macrophages (M1 macs). Grey dotted line indicates the value of untreated control.
Figure 43:
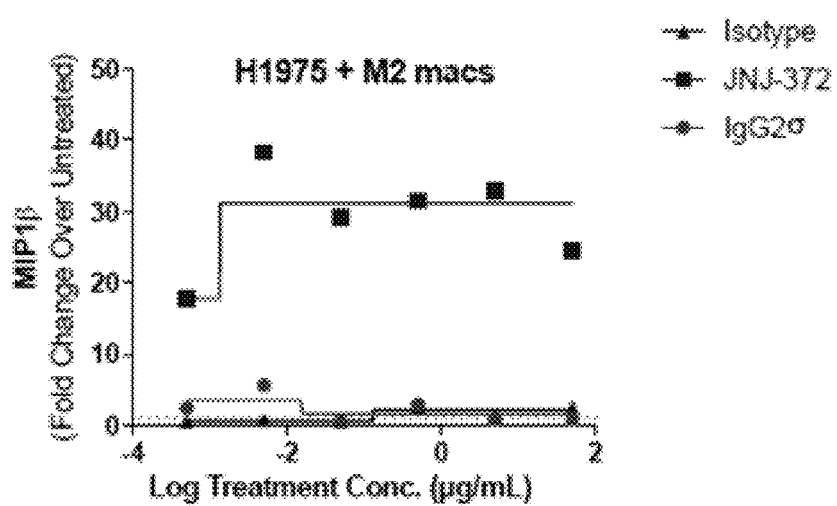
FIG. 43 shows dose-response curves from MSD based cytokine analysis measuring the fold change (compared to untreated controls) in levels of MIP-1β upon treatment of H1975 cells with JNJ-372, JNJ-372.IgG2sigma (IgG2σ in the Figure) or isotype control in the presence of M2 macrophages (M2 macs). Grey dotted line indicates the value of untreated control.
Figure 44:
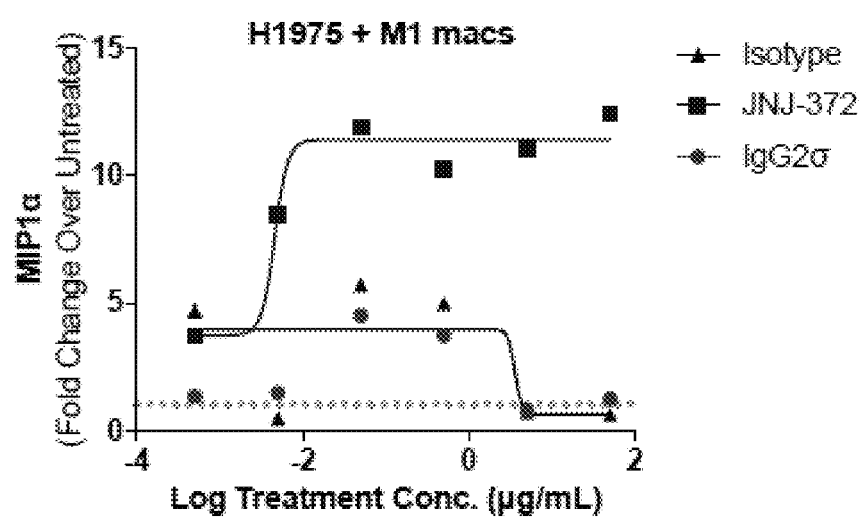
FIG. 44 shows dose-response curves from MSD based cytokine analysis measuring the fold change (compared to untreated controls) in levels of MIP-1α upon treatment of H1975 cells with JNJ-372, JNJ-372.IgG2sigma (IgG2σ in the Figure) or isotype control in the presence of M1 macrophages (M1 macs). Grey dotted line indicates the value of untreated control.
Figure 45:
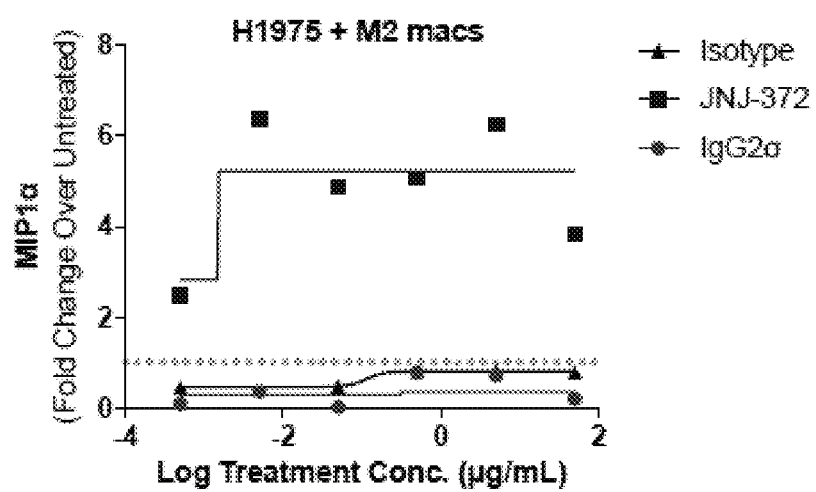
FIG. 45 shows dose-response curves from MSD based cytokine analysis measuring the fold change (compared to untreated controls) in levels of MIP-1α upon treatment of H1975 cells with JNJ-372, JNJ-372.IgG2sigma (IgG2σ in the Figure) or isotype control in the presence of M2 macrophages (M2 macs). Grey dotted line indicates the value of untreated control.

To further evaluate these cytokines and examine the role of individual immune cells in their secretion, 23 cytokines were selected (based on their function or alteration upon JNJ-372 treatment) and assessed upon treatment with isotype, JNJ-372 or JNJ-372. IgG2sigma antibodies in the presence of PBMCs vs individual immune cells isolated from the same donor. Heatmap analysis revealed distinct changes in cytokine expression patterns with the individual immune cells, with the CC chemokines being the most frequently upregulated family upon JNJ-372 treatment across all immune cells. A more focused analysis on the cytokines with >1.5-fold difference in the presence of PBMCs, revealed a pattern of upregulation upon JNJ-372 treatment that was specific to PBMCs, monocytes and macrophages but not NK cells. For example, treatment with JNJ-372 resulted in a dose-dependent increase in the levels of MCP-1 (FIG. 38) and MCP-3 (FIG. 39) in the presence of PBMCs or monocytes but not with isotype or JNJ-372.IgG2sigma or in the presence of NK cells. IL1-RA, which is known to be secreted by monocytes and macrophages in response to activating stimuli (Janson et al., *J Immunol* 147:4218-23, 1991; Arend et al., *Ann Rheum Dis* 59 Suppl 1:i60-4, 2000) increased in a dose dependent manner upon treatment with JNJ-372 in presence of PBMCs and monocytes but not NK cells (FIG. 40). Further, a dose-dependent increase in MIP1β levels was observed upon JNJ-372 treatment but not upon isotype control or JNJ-372.IgG2sigma in the presence of immune cells (FIG. 41). Both the MIP family proteins, MIP1α and MIP1β were also upregulated upon JNJ-372 treatment in co-culture with M1 and M2 macrophages, with a higher magnitude fold-change of MIP1β seen with the M2c macrophages. FIG. 42 shows the dose response curve of levels of MIP-1β in H1975 cells cultured in the presence of M1 macrophages. FIG. 43 shows the dose response curve of levels of MIP-1β in H1975 cells cultured in the presence of M2 macrophages. FIG. 44 shows the dose response curve of levels of MIP-lec in H1975 cells cultured in the presence of M1 macrophages. FIG. 45 shows the dose response curve of levels of MIP-1α in H1975 cells cultured in the presence of M2 macrophages.

To evaluate the effect of the secreted chemokines on EGFR/cMet downregulation, conditioned media from H1975 cells treated with isotype control, JNJ-372, or JNJ-372. IgG2sigma in the presence or absence of PBMCs for 4 or 72 hours was transferred onto untreated H1975 cells, and changes in EGFR and cMet pathway was assessed. No measurable downregulation of EGFR, pEGFR, and cMet protein levels was observed in the presence of conditioned media at either time point (data not shown). This suggests that secreted cytokines and chemokines were not sufficient to induce enhanced EGFR/cMet downmodulation as this requires antibody-mediated direct contact between the tumor cells and immune cells.

EXAMPLE 9

JNJ-372 Fc Interaction with Monocytes and Macrophages Induces Trogocytosis (ADCT)

Figure 46:
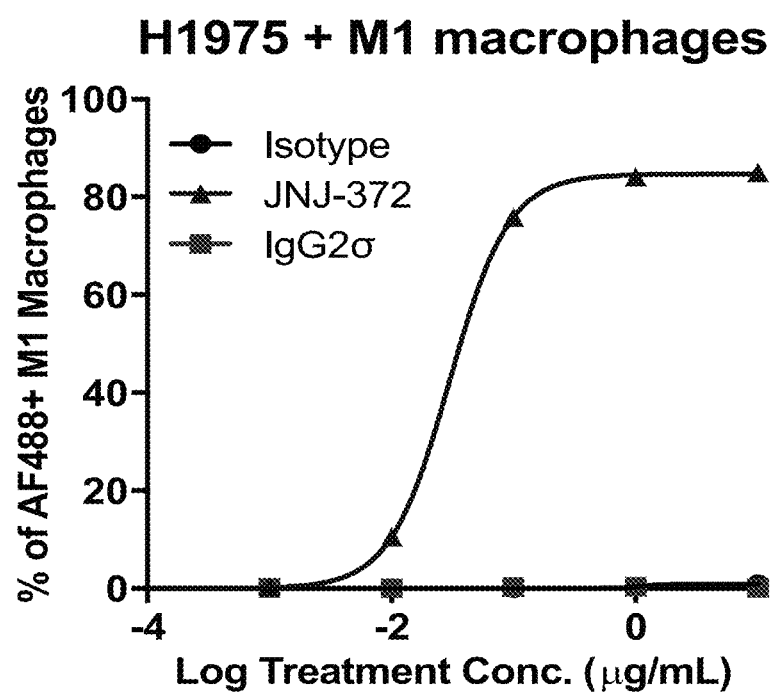
FIG. 46 shows dose-response curve from flow cytometry based trogocytosis assay measuring the percentage (%) of AF488 label within CD11b positive M1 macrophages upon opsonization of H1975 cells with labeled isotype, JNJ-372 or JNJ-372.IgG2sigma (IgG2σ in the Figure) for 3 hours. Treatment with JNJ-372 but not isotype or IgG2a induced dose-dependent trogocytosis with M1 macrophages.
Figure 47:
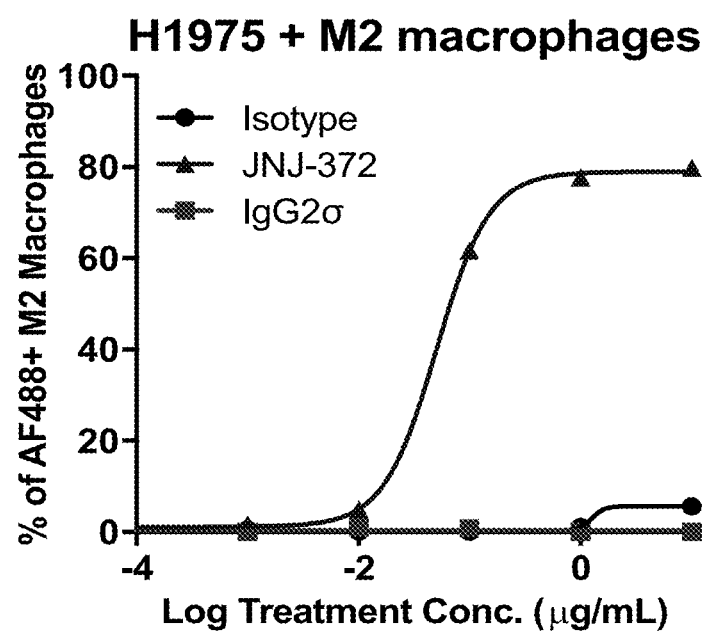
FIG. 47 shows dose-response curve from flow cytometry based trogocytosis assay measuring the percentage (%) of AF488 label within CD11b positive M2 macrophages upon opsonization of H1975 cells with labeled isotype, JNJ-372 or JNJ-372.IgG2sigma (IgG2σ in the Figure) for 3 hours. Treatment with JNJ-372 but not isotype or IgG2a induced dose-dependent trogocytosis with M2 macrophages.

Another key Fc effector function, trogocytosis (ADCT), was evaluated using a flow cytometry-based assay measuring the transfer of labelled antibody bound on target cells into effector cells (macrophages). H1975 NucLight Red cells were opsonized with AF488-labeled isotype, JNJ-372 or JNJ-372.IgG2sigma, co-cultured with M1 or M2c macrophages and the percentage of AF488+ macrophages was assessed. Labeled JNJ-372 was transferred in a dose-dependent manner to both M1 (FIG. 46) and M2c (FIG. 47) macrophages, whereas neither isotype control nor JNJ-372.IgG2sigma labeled antibody was detected in CD11b+ macrophages (data not shown). No appreciable NucLight Red+ macrophages were detected indicating a lack of phagocytosis. This suggests that trogocytosis is the predominant mechanism in this assay.

Figure 48:
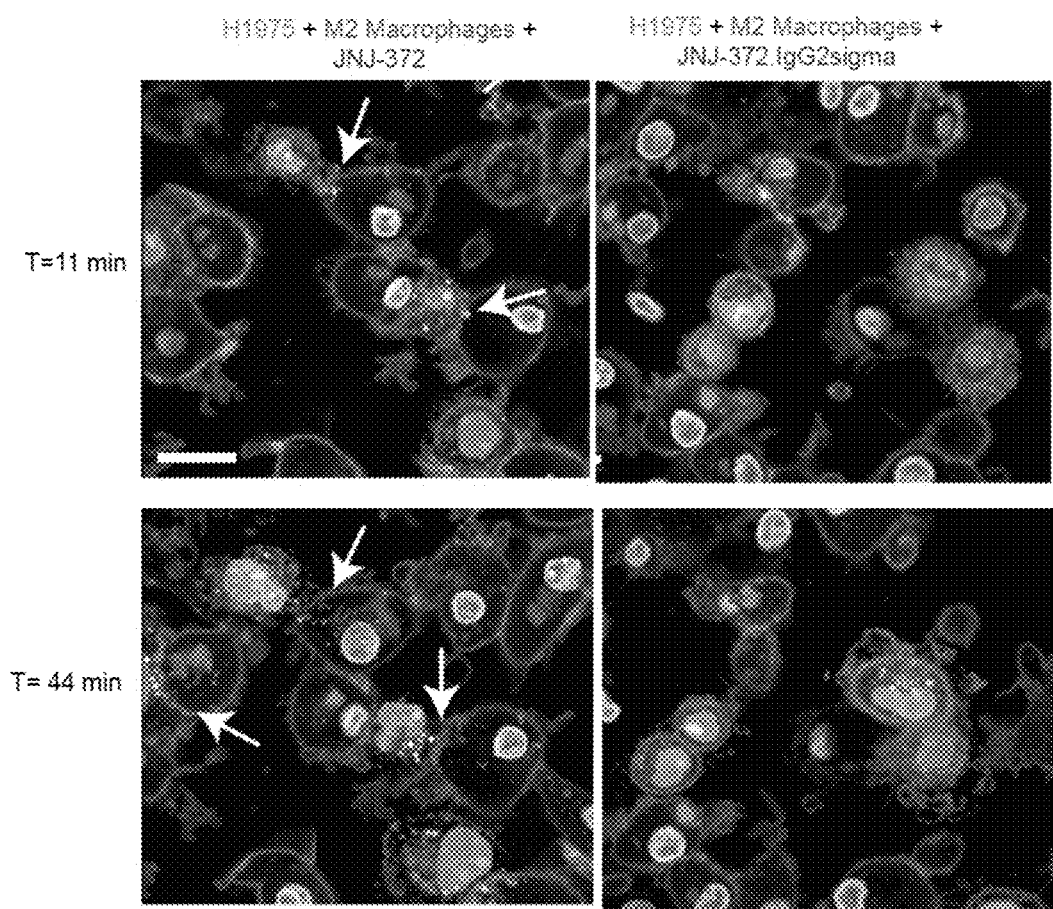
FIG. 48 shows representative images from high-content confocal microscopy showing trogocytosis of M2 macrophages labeled with FITC-CD11b (green), and Hoechst (nuclei—blue) in co-culture (E:T ratio=5:1) with H1975 NucLight Red cells opsonized with AF647-labeled JNJ-372 (purple) (top panel) or JNJ-372.IgG2sigma (purple) (bottom panel) 11 minutes (min) or 44 min post-opsonization. White arrows depict trogocytosis events measured by transfer of AF647-labeled JNJ-372 antibody from target cells to M2 macrophages. No trogocytosis was evident with JNJ-372.IgG2sigma Scale bar=20 μm. M: macrophage; T: H1975 cell.
Figure 49:
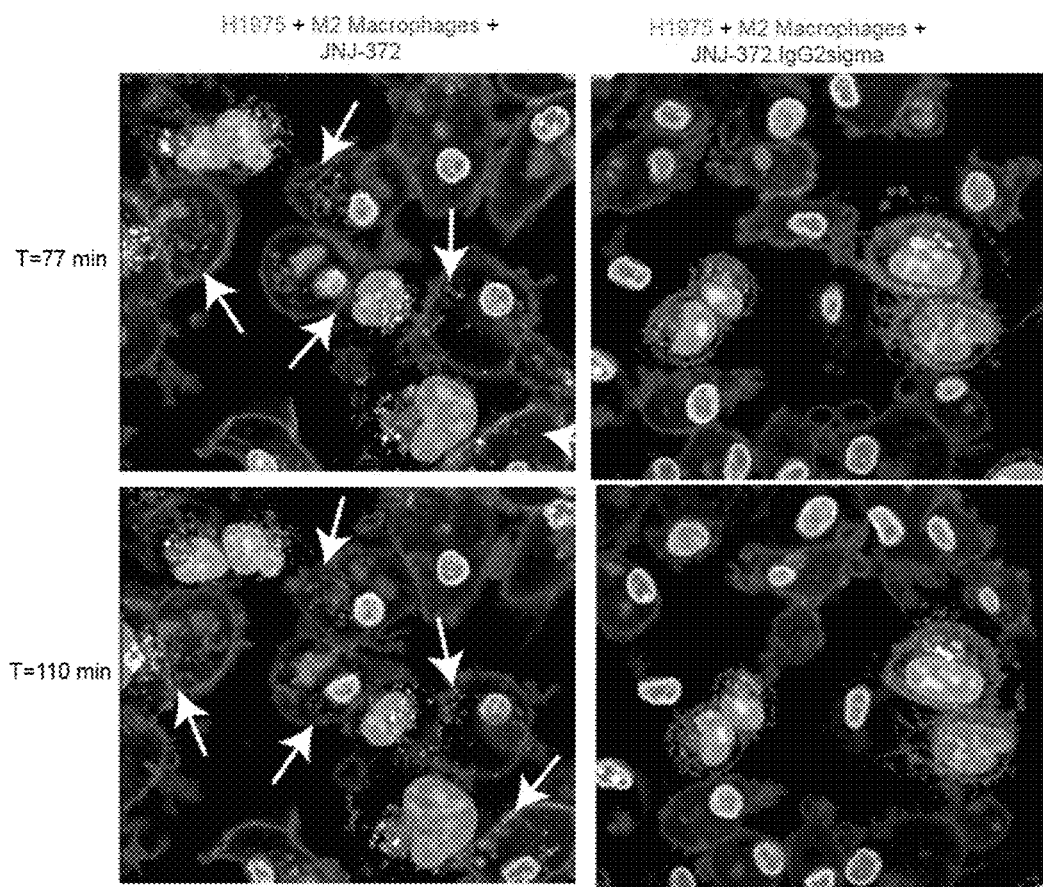
FIG. 49 shows representative images from high-content confocal microscopy showing trogocytosis of M2 macrophages labeled with FITC-CD11b (green), and Hoechst (nuclei—blue) in co-culture (E:T ratio=5:1) with H1975 NucLight Red cells opsonized with AF647-labeled JNJ-372 (purple) (top panel) or JNJ-372.IgG2sigma (purple) (bottom panel) 77 min or 110 min post-opsonization. White arrows depict trogocytosis events measured by transfer of AF647-labeled JNJ-372 antibody from target cells to M2 macrophages. No trogocytosis was evident with JNJ-372.IgG2sigma Scale bar=20 μm. M: macrophage; T: H1975 cell.

To visually confirm JNJ-372-induced macrophage trogocytosis, time-lapse microscopy was performed, where macrophages were visualized with a CD11b/CD14 antibody cocktail and Hoechst stain for nuclei and H1975 target cells were identified by their NucLight Red+nuclei. H1975 target cells were opsonized with AF647-labeled isotype, JNJ-372 or JNJ-372.IgG2sigma antibodies, co-cultured with M1 or M2c macrophages and high-content confocal images were obtained. Upon co-culture with target cells opsonized with labeled JNJ-372, a discrete accumulation of AF647+ puncta (JNJ-372) was observed within the M1 and M2 macrophages, while no accumulation was seen with the labeled isotype or JNJ-372. IgG2sigma treatment. As in the previous assay, minimal phagocytosis was observed in these assays, indicating that predominant mechanism of receptor downmodulation by JNJ-372 is trogocytosis. FIG. 48 shows representative images from high-content confocal microscopy at 11 min at 44 min of the culture. FIG. 49 shows representative images from high-content confocal microscopy at 77 min and at 110 min of the culture.

The ability of monocytes to perform trogocytosis was investigated next. Similar to macrophages, monocytes co-cultured with JNJ-372 (AF647-labeled) opsonized target cells demonstrated specific transfer of labeled JNJ-372 antibody into the monocytes (data not shown). Lastly, to simulate antibody interactions within the tumor microenvironment, a co-culture of M1 or M2c macrophages and H1975 target cells with AF647-labeled isotype were treated with JNJ-372 or JNJ-372.IgG2sigma antibodies. Under these conditions, isotype control bound only to the M1 and M2c macrophages, JNJ-372. IgG2sigma only to the target cells, whereas JNJ-372 bound to both target cells and macrophages (data not shown), thus confirming the binding specificity of each antibody. JNJ-372-mediated trogocytosis was readily observed in the co-culture conditions as well, measured by a distinct transfer of labeled JNJ-372 antibody into macrophages, but not isotype or JNJ-372.IgG2sigma antibodies.

Taken together, these findings demonstrate that JNJ-372 induces trogocytosis through its interactions with Fcγ receptors on macrophages and monocytes.

Discussion

The experiments described herein demonstrated that the EGFR/cMet bispecific antibody, JNJ-372 had multiple Fc-dependent mechanisms that contributed to its anti-tumor efficacy. In addition to inducing NK cell-mediated ADCC, the interaction of JNJ-372 with Fcγ receptors on immune cells also mediated downmodulation of the receptor tyrosine kinases EGFR and cMet and their phosphorylated forms via trogocytosis. This novel Fc function was facilitated by monocytes and macrophages, which are also required for anti-tumor efficacy in vivo.

It was demonstrated that Fc interactions of JNJ-372 with immune cells was required for the anti-proliferative and apoptotic effects in vitro and for anti-tumor efficacy in vivo. Given that the maximal anti-proliferative effect was observed at 48 hours or later and ADCC occurs early (~2 to 4 hrs (29)) in vitro, it was postulated that the contribution of ADCC to the overall tumor cell killing may be minimal While CDC activity was not observed in the cell lines evaluated, NSCLC cell lines are known to express complement inhibitory proteins, CD46, CD55, and CD59 (Varsano et al., *Clin Exp Immunol* 113: 173-82, 1998). This suggested that while JNJ-372 did not induce CDC in the cells tested, the bispecific antibody might be capable of inducing CDC activity in other cell lines or tumor types. Finally, while it has been reported previously that JNJ-372 induced ADCP in vitro (Moores et al., *Cancer Res* 76: 3942-53, 2016), under the conditions used for the flow and confocal microscopy-based trogocytosis assays in this study, minimal to no ADCP was observed. These results suggested that JNJ-372 functions through multiple mechanisms of action and that the contribution of each of these Fc effector functions may vary between patients.

It was also demonstrated that JNJ-372 induced ADCR and exploration of the functions of the cytokines upregulated by JNJ-372 revealed that most belong to the family of chemotactic cytokines called chemokines, specifically CC chemokines (Graves et al., Crit Rev Oral Biol 6: 109-18, 1995; Balkwill, Nat Rev Cancer 4: 540-50, 2004). CC chemokines are comprised of two key subfamilies, monocyte chemoattract protein (MCP) and macrophage inflammatory protein (MIP), which are known to function as chemo-attractants for innate immune cells like monocytes and macrophages (Uguccioni et al., *Eur J Immunol* 25: 64-8, 1995; Loetscher et al., *FASEB J* 8: 1055-60, 1994). The MCP family members, MCP-1 (CCL2) and MCP-3 (CCL7) have been shown to increase the recruitment of inflammatory monocytes and CD8+ T lymphocytes (Uguccioni et al., *Eur J Immunol* 25: 64-8, 1995; Loetscher et al., *FASEB J* 8: 1055-60, 1994; Jia et al., *J Immunol* 180: 6846-53, 2008). MCP-1 and MIP1β (CCL4) have also been reported to induce recruitment of monocytes and macrophages into the tumor microenvironment (TME) of NSCLC (Uguccioni et al., *Eur J Immunol* 25: 64-8, 1995; Arenberg et al., *Cancer Immunol Immunother* 49: 63-70, 2000).

While these cytokines could attract immune cells into the TME and activate them, the necessity of antibody-mediated cell-cell contact and the induction of trogocytosis suggested that the mechanism by which JNJ-372 Fc interaction mediated downmodulation of EGFR and cMet signaling was via monocyte- or macrophage-mediated trogocytosis. Several recent reports have shown that a similar transfer of Her2 receptors to immune cells like macrophages and neutrophils by trogocytosis lee to the death of therapeutic antibody opsonized tumor cells (Velmurugan et al., *Mol Cancer Ther* 15: 1879-89, 2016; Matlung et al., *Cell Rep* 23: 3946-59, 2018). This suggested that while previously trogocytosis was believed to be a mechanism of resistance for antibodies such as rituximab, it can also serve as a Fc effector function to mediate anti-tumor effects (Taylor and Lindofer, *Blood* 125: 762-6, 2015; Pham et al., *PLoS One* 6:e14498, 2011).

In conclusion, JNJ-372 was demonstrated to display multiple distinct mechanisms of actions with several Fc-dependent and Fc-independent functions contributing to its anti-tumor activity. In vitro and in vivo models demonstrated that JNJ-372 interaction with FcγRs on monocytes and macrophages were needed for EGFR/Met down-modulation and anti-tumor efficacy, suggesting that levels of these immune cells may be predictive of JNJ-372 efficacy in clinical settings.

---

We claim:

1. A method of diagnosing and treating a subject having EGFR, c-Met or EGFR and c-Met expressing cancer that is responsive to treatment with a bispecific anti-EGFR/c-Met antibody, comprising:
   (a) providing a biological sample from the subject;
   (b) measuring macrophage or monocyte levels from the biological sample;
   (c) diagnosing the subject having the EGFR, c-Met or EGFR and c-Met expressing cancer that is responsive to treatment with the bispecific anti-EGFR/c-Met antibody when the macrophage or monocyte levels from the biological sample are higher than a threshold value; and
   (d) administering the bispecific anti-EGFR/c-Met antibody to the subject diagnosed as responsive to treatment with the bispecific anti-EGFR/c-Met antibody;
   wherein the bispecific anti-EGFR/c-Met antibody comprises
   (a) a first domain that binds EGFR, wherein the first domain comprises a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6; and
   (b) a second domain that binds c-Met, wherein the second domain comprises a HCDR1 of SEQ ID NO: 7, a HCDR2 of SEQ ID NO: 8, a HCDR3 of SEQ ID NO: 9, a LCDR1 of SEQ ID NO: 10, a LCDR2 of SEQ ID NO: 11 and a LCDR3 of SEQ ID NO: 12.

2. The method of claim 1, wherein
   (a) the first domain that binds EGFR comprises a heavy chain variable region (VH) of SEQ ID NO: 13 and a light chain variable region (VL) of SEQ ID NO: 14; and
   (b) the second domain that binds c-Met comprises a VH of SEQ ID NO: 15 and a VL of SEQ ID NO: 16.

3. The method of claim 2, wherein the bispecific anti-EGFR/c-Met antibody is an IgG1 isotype.

4. The method of claim 3, wherein the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

5. The method of claim 4, wherein the threshold value is the $30^{th}$ percentile value or above of macrophages or monocytes observed in the biological sample from a population of subjects having the EGFR, c-Met or EGFR and c-Met positive cancer.

6. The method of claim 5, wherein the biological sample is a blood sample.

7. The method of claim 6, wherein the biological sample is a tumor tissue biopsy.

8. The method of claim 5, wherein the EGFR, c-Met or EGFR and c-Met expressing cancer is associated with a wild-type EGFR, an EGFR activating mutation, an EGFR gene amplification, increased levels of circulating HGF, a wild-type c-Met, a c-Met activating mutation, a c-Met gene amplification or a mutant KRAS, or any combination thereof.

9. The method of claim 8, wherein the EGFR activating mutation comprises L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between 5768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, or one or more insertions in EGFR exon 20, or any combination thereof.

10. The method of claim 9, wherein the mutant KRAS comprises a G12V, G12C or G12A substitution.

11. The method of claim 5, wherein the subject is suspected to have or has a newly diagnosed EGFR, c-Met or EGFR and c-Met expressing cancer.

12. The method of claim 5, wherein the subject is resistant or has acquired resistance to treatment with a prior anti-cancer therapy.

13. The method of claim 12, wherein the prior anti-cancer therapy is a kinase inhibitor.

14. The method of claim 13, wherein the kinase inhibitor is an inhibitor of EGFR, c-Met, HER2, HER3, HER4, VEGFR or AXL.

15. The method of claim 14, wherein the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

16. The method of claim 12, wherein the prior anti-cancer therapy is chemotherapy.

17. The method of claim 12, wherein the prior anti-cancer therapy is a targeted anti-cancer therapy.

18. The method of claim 5, wherein the EGFR, c-Met or EGFR and c-Met expressing cancer is an epithelial cell cancer, breast cancer, ovarian cancer, lung cancer, non-small cell lung cancer (NSCLC), lung adenocarcinoma, small cell lung cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC).

19. The method of claim 18, wherein the bispecific anti-EGFR/c-Met antibody is administered in combination with an agent that enhances macrophage activity in the subject.

20. The method of claim 19, wherein the agent that enhances macrophage activity in the subject is GM-CSF, a CD47 antagonist, an anti-CD47 antibody, a HDAC2 inhibitor, a PD-(L)1 axis inhibitor or a CD11b agonist.

21. The method of claim 19, further comprising administering one or more anti-cancer therapies to the subject.

22. The method of claim 21, wherein the one or more anti-cancer therapies comprise a kinase inhibitor.

23. The method of claim 22, wherein the kinase inhibitor is an inhibitor of EGFR, c-Met, HER2, HER3, HER4, VEGFR or AXL.

24. The method of claim 23, wherein the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

25. The method of claim 21, wherein the one or more anti-cancer therapies comprise chemotherapy.

26. The method of claim 21, wherein the one or more anti-cancer therapies comprise a targeted anti-cancer therapy.

27. The method of claim 5, wherein the bispecific anti-EGFR/c-Met antibody has a fucose content of about 15% or less.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: HCDR1, EGFR binding arm

<400> SEQUENCE: 1

Thr Tyr Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2, EGFR binding arm

<400> SEQUENCE: 2

Val Ile Trp Asp Asp Gly Ser Tyr Lys Tyr Tyr Gly Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: HCDR3, EGFR binding arm

<400> SEQUENCE: 3

Asp Gly Ile Thr Met Val Arg Gly Val Met Lys Asp Tyr Phe Asp Tyr
1               5                   10                  15
```

```
<210> SEQ ID NO 4
<211> LENGTH: 11
<212> TYPE: PRT
<213> ORGANISM: Artificial Sequence
<220> FEATURE:
<223> OTHER INFORMATION: LCDR1, EGFR binding arm

<400> SEQUENCE: 4

Arg Ala Ser Gln Asp Ile Ser Ser Ala Leu Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2, EGFR binding arm

<400> SEQUENCE: 5

Asp Ala Ser Ser Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3, EGFR binding arm

<400> SEQUENCE: 6

Gln Gln Phe Asn Ser Tyr Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1, c-Met binding arm

<400> SEQUENCE: 7

Ser Tyr Gly Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: HCDR2, c-Met binding arm

<400> SEQUENCE: 8

Trp Ile Ser Ala Tyr Asn Gly Tyr Thr Asn Tyr Ala Gln Lys Leu Gln
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: HCDR3, c-Met binding arm

<400> SEQUENCE: 9

Asp Leu Arg Gly Thr Asn Tyr Phe Asp Tyr
1               5                   10
```

```
<210> SEQ ID NO 10
<211> LENGTH: 11
<212> TYPE: PRT
<213> ORGANISM: Artificial Sequence
<220> FEATURE:
<223> OTHER INFORMATION: LCDR1, c-Met binding arm

<400> SEQUENCE: 10

Arg Ala Ser Gln Gly Ile Ser Asn Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LCDR2, c-Met binding arm

<400> SEQUENCE: 11

Ala Ala Ser Ser Leu Leu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3, c-Met binding arm

<400> SEQUENCE: 12

Gln Gln Ala Asn Ser Phe Pro Ile Thr
1               5

<210> SEQ ID NO 13
<211> LENGTH: 125
<212> TYPE: PRT
<213> ORGANISM: Artificial Sequence
<220> FEATURE:
<223> OTHER INFORMATION: VH, EGFR binding arm

<400> SEQUENCE: 13

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 14
<211> LENGTH: 107
<212> TYPE: PRT
<213> ORGANISM: Artificial Sequence
<220> FEATURE:
```

<223> OTHER INFORMATION: VL, EGFR binding arm

<400> SEQUENCE: 14

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 15
<211> LENGTH: 119
<212> TYPE: PRT
<213> ORGANISM: Artificial Sequence
<220> FEATURE:
<223> OTHER INFORMATION: VH, c-Met binding arm

<400> SEQUENCE: 15

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: VL, c-Met binding arm

<400> SEQUENCE: 16

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
            100                 105

<210> SEQ ID NO 17
<211> LENGTH: 455
<212> TYPE: PRT
<213> ORGANISM: Artificial Sequence
<220> FEATURE:
<223> OTHER INFORMATION: HC1

<400> SEQUENCE: 17

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Thr Tyr
                 20                  25                  30

Gly Met His Trp Val Arg Gln Ala Pro Gly Lys Gly Leu Glu Trp Val
             35                  40                  45

Ala Val Ile Trp Asp Asp Gly Ser Tyr Lys Tyr Tyr Gly Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
```

```
305                 310                 315                 320
Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 18
<211> LENGTH: 214
<212> TYPE: PRT
<213> ORGANISM: Artificial Sequence
<220> FEATURE:
<223> OTHER INFORMATION: LC1

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 19
<211> LENGTH: 449
<212> TYPE: PRT
<213> ORGANISM: Artificial Sequence
<220> FEATURE:
<223> OTHER INFORMATION: HC2

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
                    355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 20
<211> LENGTH: 214
<212> TYPE: PRT
<213> ORGANISM: Artificial Sequence
<220> FEATURE:
<223> OTHER INFORMATION: LC2

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```